US010563202B2

(12) United States Patent
Collard et al.

(10) Patent No.: US 10,563,202 B2
(45) Date of Patent: *Feb. 18, 2020

(54) TREATMENT OF SIRTUIN (SIRT) RELATED DISEASES BY INHIBITION OF NATURAL ANTISENSE TRANSCRIPT TO A SIRTUIN (SIRT)

(71) Applicant: CuRNA, Inc., Miami, FL (US)

(72) Inventors: Joseph Collard, Delray Beach, FL (US); Olga Khorkova Sherman, Tequesta, FL (US)

(73) Assignee: GuRNA, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/701,998

(22) Filed: May 1, 2015

(65) Prior Publication Data
US 2015/0267204 A1 Sep. 24, 2015

Related U.S. Application Data

(63) Continuation of application No. 13/386,057, filed as application No. PCT/US2010/043075 on Jul. 23, 2010, now abandoned, which is a continuation-in-part of application No. PCT/US2009/066445, filed on Dec. 2, 2009, and a continuation-in-part of application No. PCT/US2010/026119, filed on Mar. 3, 2010.

(60) Provisional application No. 61/228,392, filed on Jul. 24, 2009, provisional application No. 61/259,072, filed on Nov. 6, 2009.

(51) Int. Cl.
C12N 15/11 (2006.01)
C12N 15/113 (2010.01)

(52) U.S. Cl.
CPC ...... *C12N 15/1137* (2013.01); *C12N 2310/11* (2013.01); *C12N 2310/14* (2013.01); *C12N 2310/315* (2013.01); *C12N 2320/30* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,034,506 A | 7/1991 | Summerton et al. |
| 5,138,045 A | 8/1992 | Cook et al. |
| 5,218,105 A | 6/1993 | Cook et al. |
| 5,288,512 A | 2/1994 | Seiden |
| 5,288,514 A | 2/1994 | Ellman |
| 5,319,080 A | 6/1994 | Leumann |
| 5,393,878 A | 2/1995 | Leumann |
| 5,432,272 A | 7/1995 | Benner et al. |
| 5,457,189 A | 10/1995 | Crooke et al. |
| 5,459,255 A | 10/1995 | Cook et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,576,302 A | 11/1996 | Cook et al. |
| 5,593,853 A | 1/1997 | Chen et al. |
| 5,605,662 A | 2/1997 | Heller et al. |
| 5,661,134 A | 8/1997 | Cook et al. |
| 5,708,161 A | 1/1998 | Reese |
| 5,730,119 A | 4/1998 | Galli et al. |
| 5,739,311 A | 4/1998 | Lackey et al. |
| 5,756,710 A | 5/1998 | Stein et al. |
| 5,849,902 A | 12/1998 | Arrow et al. |
| 5,891,725 A | 4/1999 | Soreq et al. |
| 5,902,880 A | 5/1999 | Thompson |
| 5,908,779 A | 6/1999 | Carmichael et al. |
| 5,965,721 A | 10/1999 | Cook et al. |
| 5,985,663 A | 11/1999 | Bennett et al. |
| 6,005,095 A | 12/1999 | Capaccioli et al. |
| 6,013,639 A | 1/2000 | Peyman et al. |
| 6,013,786 A | 1/2000 | Chen et al. |
| 6,034,233 A | 3/2000 | Ecker et al. |
| 6,100,090 A | 8/2000 | Monia et al. |

(Continued)

FOREIGN PATENT DOCUMENTS

| | | | |
|---|---|---|---|
| CA | 2686933 | | 4/2008 |
| CN | 101240271 A | * | 8/2008 |

(Continued)

OTHER PUBLICATIONS

Behlke et al, Designing Antisense Oligonucleotides, 2005, Integrated DNA Technologies, pp. 1-17.*
Machine translation of CN 101240271, pp. 1-12 (Year: 2008).*
Machine translation of WO 2004/056993 A1, pp. 1-30 (Year: 2004).*
Ausubel, Current Protocols in Molecular Biology vol. 1, 1994, 6.0.1-6.4.10.
Barak, et al., "A β-Arrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience Letters 207:17-20 (1996).

(Continued)

*Primary Examiner* — Ekaterina Poliakova-Georgantas
(74) *Attorney, Agent, or Firm* — GuRNA, Inc.; Monte R. Browder

(57) ABSTRACT

The present invention relates to antisense oligonucleotides that modulate the expression of and/or function of a Sirtuin (SIRT), in particular, by targeting natural antisense polynucleotides of a Sirtuin (SIRT). The invention also relates to the identification of these antisense oligonucleotides and their use in treating diseases and disorders associated with the expression of Sirtuins (SIRT)s.

13 Claims, 10 Drawing Sheets

Specification includes a Sequence Listing.

(56) References Cited

U.S. PATENT DOCUMENTS

| | | | |
|---|---|---|---|
| 6,140,492 A | 10/2000 | Morelli et al. | |
| 6,147,200 A | 11/2000 | Manoharan et al. | |
| 6,165,712 A | 12/2000 | Foulkes et al. | |
| 6,165,990 A | 12/2000 | Singh et al. | |
| 6,175,409 B1 | 1/2001 | Nielsen et al. | |
| 6,221,587 B1 | 4/2001 | Ecker et al. | |
| 6,239,265 B1 | 5/2001 | Cook | |
| 6,242,589 B1 | 6/2001 | Cook et al. | |
| 6,268,490 B1 | 7/2001 | Imanishi et al. | |
| 6,303,374 B1 | 10/2001 | Zhang et al. | |
| 6,307,040 B1 | 10/2001 | Cook et al. | |
| 6,316,198 B1 | 11/2001 | Skouv et al. | |
| 6,335,434 B1 | 1/2002 | Guzaev et al. | |
| 6,376,541 B1 | 4/2002 | Nixon et al. | |
| 6,403,566 B1 | 6/2002 | Wang | |
| 6,444,464 B1 | 9/2002 | Wyatt | |
| 6,451,991 B1 | 9/2002 | Martin et al. | |
| 6,525,191 B1 | 2/2003 | Ramassamy | |
| 6,523,363 B1 | 3/2003 | Cook et al. | |
| 6,528,262 B1 | 3/2003 | Glad et al. | |
| 6,617,122 B1 | 9/2003 | Hayden et al. | |
| 6,617,442 B1 | 9/2003 | Crooke et al. | |
| 6,630,315 B1 | 10/2003 | Miwa et al. | |
| 6,639,059 B1 | 10/2003 | Kochkine et al. | |
| 6,656,730 B1 | 12/2003 | Manoharan | |
| 6,667,337 B2 | 12/2003 | Wilson | |
| 6,670,461 B1 | 12/2003 | Wengel et al. | |
| 6,710,174 B2 | 3/2004 | Bennett et al. | |
| 6,734,291 B2 | 5/2004 | Kochkine et al. | |
| 6,762,169 B1 * | 7/2004 | Manoharan | A61K 47/64 435/440 |
| 6,794,499 B2 | 9/2004 | Wengel et al. | |
| 6,833,361 B2 | 12/2004 | Hong et al. | |
| 6,861,514 B2 | 3/2005 | Cook et al. | |
| 6,867,294 B1 | 3/2005 | Sanghvi et al. | |
| 6,936,467 B2 | 8/2005 | Kmiec et al. | |
| 6,936,593 B1 | 8/2005 | Agrawal et al. | |
| 6,977,295 B2 | 12/2005 | Belotserkovskii et al. | |
| 6,986,988 B2 | 1/2006 | Gilad et al. | |
| 7,034,133 B2 | 4/2006 | Wengel et al. | |
| 7,034,145 B2 | 4/2006 | Shen et al. | |
| 7,053,195 B1 | 5/2006 | Goff | |
| 7,053,199 B2 | 5/2006 | Imanishi et al. | |
| 7,053,207 B2 | 5/2006 | Wengel | |
| 7,060,809 B2 | 6/2006 | Wengel et al. | |
| 7,084,125 B2 | 8/2006 | Wengel | |
| 7,087,589 B2 | 8/2006 | Jacobson et al. | |
| 7,125,982 B1 | 10/2006 | Frayne | |
| 7,144,995 B2 | 12/2006 | Wise et al. | |
| 7,144,999 B2 | 12/2006 | Ward et al. | |
| 7,148,204 B2 | 12/2006 | Bennett et al. | |
| 7,153,954 B2 | 12/2006 | Koch et al. | |
| 7,169,916 B2 | 1/2007 | Krotz et al. | |
| 7,199,107 B2 | 4/2007 | Dobie et al. | |
| 7,202,357 B2 | 4/2007 | Crooke et al. | |
| 7,217,572 B2 | 5/2007 | Ward et al. | |
| 7,220,549 B2 | 5/2007 | Buzby | |
| 7,226,785 B2 | 6/2007 | Kmiec et al. | |
| 7,229,974 B2 | 6/2007 | Peyman et al. | |
| 7,229,976 B2 | 6/2007 | Dobie et al. | |
| 7,235,534 B2 | 6/2007 | Tanguay et al. | |
| 7,235,653 B2 | 6/2007 | Bennett et al. | |
| 7,238,858 B2 | 7/2007 | Marraccini et al. | |
| 7,276,599 B2 | 10/2007 | Moore et al. | |
| 7,285,288 B1 | 10/2007 | Tormo et al. | |
| 7,297,786 B2 | 11/2007 | McCray et al. | |
| 7,314,923 B2 | 1/2008 | Kaneko et al. | |
| 7,320,965 B2 | 1/2008 | Sah et al. | |
| 7,321,828 B2 | 1/2008 | Cowsert et al. | |
| 7,335,764 B2 | 2/2008 | Crooke et al. | |
| 7,335,765 B2 | 2/2008 | Kaneko et al. | |
| 7,339,051 B2 | 3/2008 | Crooke et al. | |
| 7,371,833 B1 | 5/2008 | Weiss | |
| 7,399,845 B2 | 7/2008 | Seth et al. | |
| 7,402,434 B2 | 7/2008 | Newman et al. | |
| 7,402,574 B2 | 7/2008 | Iversen et al. | |
| 7,420,050 B2 | 9/2008 | Patt et al. | |
| 7,423,142 B2 | 9/2008 | Vornlocher | |
| 7,425,545 B2 | 9/2008 | Crooke et al. | |
| 7,427,675 B2 | 9/2008 | Capaldi et al. | |
| 7,456,154 B2 | 11/2008 | Soreq et al. | |
| 7,462,642 B2 | 12/2008 | Wang et al. | |
| 7,468,431 B2 | 12/2008 | Bhanot et al. | |
| 7,510,830 B2 | 3/2009 | Baguley et al. | |
| 7,541,344 B2 | 6/2009 | Bhat et al. | |
| 7,547,684 B2 | 6/2009 | Seth et al. | |
| 7,569,575 B2 | 8/2009 | Sorensen et al. | |
| 7,569,686 B1 | 8/2009 | Bhat et al. | |
| 7,572,582 B2 | 8/2009 | Wengel et al. | |
| 7,582,745 B2 | 9/2009 | Sah et al. | |
| 7,585,893 B2 | 9/2009 | Baguley et al. | |
| 7,589,190 B2 | 9/2009 | Westerpard et al. | |
| 7,598,227 B2 | 10/2009 | Crooke et al. | |
| 7,605,251 B2 | 10/2009 | Tan et al. | |
| 7,622,453 B2 | 11/2009 | Frieden et al. | |
| 7,662,948 B2 | 2/2010 | Kurreck et al. | |
| 7,666,854 B2 | 2/2010 | Seth et al. | |
| 7,674,895 B2 | 3/2010 | Reich et al. | |
| 7,687,617 B2 | 3/2010 | Thrue et al. | |
| 7,691,995 B2 | 4/2010 | Zamore et al. | |
| 7,695,902 B2 | 4/2010 | Crooke | |
| 7,696,345 B2 | 4/2010 | Mersin et al. | |
| 7,709,456 B2 | 5/2010 | Corey et al. | |
| 7,709,630 B2 | 5/2010 | Gaarde et al. | |
| 7,713,738 B2 | 5/2010 | Hansen et al. | |
| 7,718,629 B2 | 5/2010 | Bumcrot et al. | |
| 7,723,508 B2 | 5/2010 | Crooke et al. | |
| 7,732,422 B2 | 6/2010 | Gleave et al. | |
| 7,732,590 B2 | 6/2010 | Bhanot et al. | |
| 7,737,264 B2 | 6/2010 | Thrue et al. | |
| 7,737,265 B2 | 6/2010 | Akinc et al. | |
| 7,741,305 B2 | 6/2010 | Crooke et al. | |
| 7,741,309 B2 | 6/2010 | Hansen et al. | |
| 7,741,457 B2 | 6/2010 | Seth et al. | |
| 7,745,609 B2 | 6/2010 | Bennett et al. | |
| 7,749,978 B2 | 7/2010 | Sah et al. | |
| 2003/0139359 A1 | 7/2003 | Dobie | |
| 2003/0186920 A1 | 10/2003 | Sirois | |
| 2003/0191075 A1 | 10/2003 | Cook et al. | |
| 2003/0213670 A1 | 12/2003 | Edgerton et al. | |
| 2003/0228618 A1 | 12/2003 | Levanon et al. | |
| 2004/0006031 A1 | 1/2004 | Dean et al. | |
| 2004/0033480 A1 | 2/2004 | Wong | |
| 2004/0101858 A1 | 5/2004 | Ward et al. | |
| 2004/0137423 A1 | 7/2004 | Hayden et al. | |
| 2004/0138155 A1 | 7/2004 | Baird et al. | |
| 2004/0175803 A1 | 9/2004 | Meritet et al. | |
| 2004/0180336 A1 | 9/2004 | Gilad et al. | |
| 2004/0254137 A1 | 12/2004 | Ackermann et al. | |
| 2005/0009771 A1 | 1/2005 | Levanon et al. | |
| 2005/0026160 A1 | 2/2005 | Allerson et al. | |
| 2005/0100885 A1 * | 5/2005 | Crooke | C07K 16/10 435/5 |
| 2005/0113326 A1 | 5/2005 | Siwkowski et al. | |
| 2005/0143333 A1 * | 6/2005 | Richards | A61K 49/0008 514/44 A |
| 2005/0143357 A1 | 6/2005 | Pousette et al. | |
| 2005/0153286 A1 | 7/2005 | Clements | |
| 2005/0196781 A1 * | 9/2005 | Robin | C07H 21/02 435/6.11 |
| 2005/0215504 A1 | 9/2005 | Bennett et al. | |
| 2005/0222029 A1 | 10/2005 | Bartel et al. | |
| 2005/0246794 A1 * | 11/2005 | Khvorova | A61K 31/713 800/286 |
| 2005/0266409 A1 * | 12/2005 | Brown | C12Q 1/6886 435/6.14 |
| 2006/0009410 A1 | 1/2006 | Crooke et al. | |
| 2006/0142196 A1 | 6/2006 | Klein et al. | |
| 2006/0178333 A1 | 8/2006 | Soreq et al. | |
| 2007/0042982 A1 * | 2/2007 | Bentwich | C12Q 1/689 514/44 A |
| 2007/0082848 A1 | 4/2007 | Alitalo et al. | |
| 2007/0197459 A1 | 8/2007 | Milner | |
| 2007/0213274 A1 | 9/2007 | Salonen | |

(56) References Cited

U.S. PATENT DOCUMENTS

| | | |
|---|---|---|
| 2007/0213292 A1 | 9/2007 | Stoffel et al. |
| 2007/0231816 A1 | 10/2007 | Chaussabel et al. |
| 2007/0248590 A1 | 10/2007 | Milne et al. |
| 2008/0124301 A1* | 5/2008 | Schlingensiepen .... A61K 45/06 424/85.2 |
| 2008/0146788 A1 | 6/2008 | Bhat et al. |
| 2008/0221051 A1 | 9/2008 | Becker et al. |
| 2008/0293142 A1 | 11/2008 | Liu et al. |
| 2009/0149403 A1* | 6/2009 | MacLachlan ........ C12N 15/113 514/44 R |
| 2009/0191263 A1 | 7/2009 | Reich et al. |
| 2009/0192106 A1 | 7/2009 | Dobie et al. |
| 2009/0208479 A1 | 8/2009 | Jaye et al. |
| 2009/0258925 A1 | 10/2009 | Wahlestedt |
| 2009/0318536 A1 | 12/2009 | Freier et al. |
| 2009/0326041 A1 | 12/2009 | Bhanot et al. |
| 2010/0105760 A1 | 4/2010 | Collard et al. |

FOREIGN PATENT DOCUMENTS

| | | | |
|---|---|---|---|
| EP | 335451 A3 | 3/1988 | |
| EP | 335451 A2 | 10/1989 | |
| WO | WO-1984103564 | 9/1984 | |
| WO | WO-1991/19735 | 12/1991 | |
| WO | WO-1992/00091 | 1/1992 | |
| WO | WO-1992/08796 | 5/1992 | |
| WO | WO-1993/20242 | 10/1993 | |
| WO | WO-1994/026887 A1 | 11/1994 | |
| WO | WO-1994/28143 | 12/1994 | |
| WO | WO-1995/015373 A2 | 6/1995 | |
| WO | WO-1995/22618 | 8/1995 | |
| WO | WO-1995/25116 | 10/1995 | |
| WO | WO-1995/35505 | 12/1995 | |
| WO | WO-9624380 A1 * | 8/1996 | ......... C12N 15/1138 |
| WO | WO-1996-027663 A2 | 9/1996 | |
| WO | WO-1997-039120 A1 | 10/1997 | |
| WO | WO-1999-014226 A1 | 3/1999 | |
| WO | WO-9913886 A1 * | 3/1999 | ............ A61K 31/00 |
| WO | WO-1999-039352 A1 | 8/1999 | |
| WO | WO-2000-057837 A1 | 10/2000 | |
| WO | WO-2000-061770 A2 | 10/2000 | |
| WO | WO-0078341 A1 * | 12/2000 | ........... C12N 15/113 |
| WO | WO-2001-000669 A2 | 1/2001 | |
| WO | WO-2001-21631 A2 | 3/2001 | |
| WO | WO-2001-025488 A2 | 4/2001 | |
| WO | WO-2001-051630 A1 | 7/2001 | |
| WO | WO-2002-062840 A1 | 8/2002 | |
| WO | WO-2002-068688 A1 | 9/2002 | |
| WO | WO 03022227 A2 * | 3/2003 | ......... C12N 15/1138 |
| WO | WO-2004-016255 A1 | 2/2004 | |
| WO | WO-2004-024079 A2 | 3/2004 | |
| WO | WO-2004-030750 A1 | 3/2004 | |
| WO | WO-2004-041838 A1 | 5/2004 | |
| WO | WO-2004056993 A1 * | 7/2004 | ............ C07K 14/415 |
| WO | WO 2004092383 A2 * | 10/2004 | ......... C12N 15/1131 |
| WO | WO-2004-104161 A2 | 12/2004 | |
| WO | 2005004814 A2 | 1/2005 | |
| WO | 2005007106 A2 | 1/2005 | |
| WO | WO-2005-045034 A2 | 5/2005 | |
| WO | WO-2005-070136 A2 | 8/2005 | |
| WO | 2005090996 A1 | 9/2005 | |
| WO | WO-2005-079862 A1 | 9/2005 | |
| WO | WO-2005097993 A2 * | 10/2005 | ............ A61K 39/39 |
| WO | 2005110464 A2 | 11/2005 | |
| WO | 2005110464 A3 | 11/2005 | |
| WO | WO-2006063152 A2 * | 6/2006 | ............ A61K 39/39 |
| WO | WO-2007-028065 A2 | 3/2007 | |
| WO | WO-2007-071182 A1 | 6/2007 | |
| WO | WO-2007-087113 A2 | 8/2007 | |
| WO | WO-2007-138023 A1 | 12/2007 | |
| WO | WO-2008025160 A1 * | 3/2008 | ............ C07H 19/06 |
| WO | WO-2008-057556 A2 | 5/2008 | |
| WO | WO-2008-066672 A2 | 6/2008 | |
| WO | WO-2008-087561 A2 | 7/2008 | |
| WO | WO-2009083790 A2 * | 7/2009 | ........... C12N 15/111 |
| WO | WO-2010-002984 A1 | 1/2010 | |
| WO | WO-2010-040571 A2 | 4/2010 | |
| WO | WO-2010-054364 A1 | 5/2010 | |
| WO | WO-2010-058227 A2 | 5/2010 | |
| WO | 2010102058 A2 | 9/2010 | |
| WO | 2011011700 A2 | 1/2011 | |
| WO | 2011139387 A1 | 11/2011 | |

OTHER PUBLICATIONS

Baum, "Solid-phase synthesis of benzodiazepines," C&EN News, Jan. 18, p. 33-34 (1993).

Bernstein, E., et al., "Role for a Bidentate Ribonuclease in the Initiation of Step of RNA Interference," Nature 409:363-366 (2001).

Boutla, A., et al., "Short 5'-phosphorylated double-stranded RNAs induce RNA interference in *Drosophila*," Curr. Biol. 11:1776-1780 (2001).

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

Brazma & Vilo, "Gene expression data analysis," FEBS Lett., 480:17-24 (2000).

Bright, et al., "Chapter 6, Fluorescence Ratio Imaging Microscopy," Methods in Cell Biology vol. 30, Taylor and Wang (eds) p. 157-192 (1989).

Bright, et al., "Delivery of Macromolecules Into Adherent Cells via Electroporation for Use in Fluorescence Spectroscopic Imaging and Metabolic Studies," Cytometry 24:226-233 (1996).

Bright, et al., "Fluorescence Ratio Imaging Microscopy: Temporal and Spatial Measurements of Cytoplasmic pH," J. Cell Biology 104:1019-1033 (1987).

Campbell, et al., "Phosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).

Carninci, et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al., "Gene expression profiling: monitoring transcription and translation products using DNA microarrays and proteomics," FEBS Lett., 480:2-16 (2000).

Chabala, J.C., "Solid-phase combinatorial chemistry and novel tagging methods for identifying leads," Curr Opin Biomtechnol. 6:632-639 (1995).

Cech, J., "Ribozymes and Their Medical Implications," American. Med Assoc. 260:3030-3035 (1988).

Chen, et al., "Expression of ssDNA in Mammalian Cells," BioTechniques 34:167-171 (2003).

Chen, et al., "Analogous Organic Synthesis of Small-Compound Libraries: Validation of Combinatorial Chemistry in Small-Molecule Synthesis," J. Amer. Chem. Soc. 116:2661-2662 (1994).

Cheng, J. et al., "Transcriptional maps of 10 human chromosomes at 5-nucleotide resolution," Science 308:5725:1149-1154 (2005).

Cho, et al., "An Unnatural Biopolymer," Science 261:1303-1305 (1993).

Christiensen, N.K. et al., "A Novel Class of Oligonucleotide Analogues Containing 2'-O,3'-C-Linked [3.2.0] Bicycloarabinonucleoside Monomers: Synthesis, Thermal Affinity Studies, and Molecular Modeling," J. Am. Chem. Soc., 120:5458-5463 (1998).

Cubitt, et al. , "Understanding, improving and using green fluorescent proteins," Trends in Biochemical Science 20:448-455 (1995).

Curiel, D. T. et al., "Adenovirus Enhancement of Transferrin-Polylysine-Mediated Gene Delivery," PNAS 88:8850-8854 (1991).

Dai et al., "SIRT1 Interacts With p73 and Suppresses p73-Dependent Transcriptional Activity," J Cell Physiol 210(1):161-165 (2007).

Davidson, et al., "A model system for in vivo gene transfer into the central nervous system using an adenoviral vector," Nat. Genet 3:219-223 (1993).

(56) References Cited

OTHER PUBLICATIONS

Davis, et al., "Direct Gene Transfer into Skeletal Muscle in Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng et al., "Small Interfering RNA Targeting the PINK 1 Induces Apoptosis in Dopaminergic Cells SH-SY5Y", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).
Eguchi, et al., "Antisense RNA." Annu. Rev. Biochem. 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt, C., "RNA interference is not involved in natural antisense mediated regulation of gene expression in mammals," Genome Biol (2005), p. 1-9.
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simple virus type 1 vector," PNAS U.S.A. :90:7603-7607 (1993).
Geller, A.I., et al., "Infection of cultured central nervous system neurons with a defective herpes simplex virus 1 vector results in stable expression of Escherichia coli β-galactosidase," PNAS USA 87:1149-1153 (1990).
GenBank Accession No. NM_000559, Homo sapiens Hemoglobin, Gamma A (HBG1), mRNA, (2008), p. 1-4.
Giuliano, et al., "Fluorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21, pp. 9724-9733, (2005).
Heller, et al., "Discovery and Analysis of Inflammatory Disease-Related Genes Using cDNA Microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem., Soc., 114:9217-9218 (1992).
Hobbs-DeWitt, et al., "Diversomers: An approach to nonpeptide, nonoligomeric chemical diversity," Proc. Nat. Acad. Sci. USA 90:6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome." Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification or enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, pp. 75-77, (1980).
Larson, et al., "Rapid DNA Fingerprinting of Pathogens by Flow Cytometry," Cytometry, 2000, 41:203-208 (2000).
Larsson, et al., "High-Throughput Protein Expression of cDNA Products as a Tool in Functional Genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, Properties, and Activity as Inhibitors of Replication of Human Immunodeficiency Virus in Cell Culture," PNAS 86:6553-6556 (1989).
Li et al., "Control of APP processing and Aβ generation level by BACE1 enzymatic activity and transcription," Faseb J 20; 285-292 (2006).
Li, et al., J. Neurochem 89 1308-1312 (2004).
Liang, et al., "Parallel Synthesis and Screening of a Solid Phase Carbohydrate Library," Science 274:1520-1522 (1996).

(56) References Cited

OTHER PUBLICATIONS

Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense of oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Morelli et al., "The antisense bcl-2-IgH transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:238-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):1104-1108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S., in Crooke, S.T. and Lebleu, B., eds., Antisense Research and Applications, CRC Press, Boca Raton, 1993, p. 276-278.

Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-olipdeoxynucleotide conjugates," Nucl. Acids Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindoeyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The various aggregation states off β-amyloid 1-42 mediate different effects on oxidative stress, neurodegeneration, and BACE-1 expression," Free Radic Biol Med 41:202-212 (2006).
Thakker., D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero. "Do natural antisense transcripts make sense in eukaryotes?" Gene 211:1-9 (1998).

(56) References Cited

OTHER PUBLICATIONS

Vaughn, et al., "Human Antibodies with Sub-nanomolar Affinities Isolated from a Large Non-immunized Phage Display Library," Nature Biotechnology, 14:3:309-314 (1996).

Velculescu, et al., "Serial Analysis of Gene Expression," Science 270:484-487 (1995).

Wahlestedt, "Natural antisense and noncoding RNA transcripts as potential drug targets," Drug Discovery Today 11 (11/12):503-508 (2006).

Wahlestedt, C., "Antisense oligonucleotide strategies in neuropharmacology," Trends Pharmacol Sci 15:2:42-46 (1994).

Walsh, et al., The role of cell-derived oligomers of Aβ in Alzheimer's disease and avenues for therapeutic intervention, Biochem Soc Trans 33: 1087-1090 (2005).

Wang, B.B. et al., "Identification of a nuclear-specific cyclophilin which interacts with the proteinase inhibitor eglin c," Biochem J. 314 (Pt 1) 313-319 (1996).

Wiesenhofer, et al., "Glial cell line-derived neurotrophic factor (GDNP) is a proliferation factor for rat C6 glioma cells: evidence from antisense experiments," Antisense & Nucleic Acid Drug Development 10(5):311-321 (2000).

Xue, et al., "Hypoxia and reoxygenation increased BACE1 mRNA and protein levels in human neuroblastoma SH-SY5Y cells," Neurosci Lett 405,231-235 (2006).

Yamada, et al., "Endothelial Nitric-Oxide Synthase Antisense (NOS3AS) Gene Encodes an Autophagy-Related Protein (APG9-like2) Highly Expressed in Trophoblast" (2005), p. 18283-18290.

Yang, et al., "Cellular and Humoral Immune Responses to Viral Antigens Create Barriers to Lung-Directed Gene Therapy with Recombinant Adenoviruses," J. Virol 69:2004-2015 (1995).

Yoshigai, et al., "Characterization of Natural Antisense Transcripts Expressed from Interleukin 1β-inducible Genes in Rat Hepatocytes," HOAJ Biology; 1-10 (2012).

EP Application No. 06850393.7 Examination Report dated Oct. 18, 2011.

International Search Report and Written Opinion for PCT Application No. PCT/US2010/033078 dated Jun. 29, 2011.

PCT/US2010/026119 Search Report and Written Opinion dated Feb. 7, 2011.

PCT/US2010/024079 Search Report and Written Opinion dated Jan. 31, 2011.

PCT/US2010/027394 Search Report and Written Opinion dated Nov. 5, 2010.

PCT/US96/10287 (WO97/000271) The Regents of the University of California Jan. 3, 1997.

Donmez, G., "The Effects of SIRT1 on Alzheimer's Disease Models," International Journal of Alzheimer's Disease, vol. 2012, Article ID 509529, pp. 1-3 (2012).

Ming, M., et al., "Loss Sirtuin 1 (SIRT1) Disrupts Skin Barrier Integrity and Sensitizes Mice to Epicutaneous Allergen Challenge," J Allergy Clin Immunol, vol. 135, No. 4, pp. 936-945, (2015).

Wahlestedt, C., "Natural Antisense and Non-Coding RNA Transcripts as Drug Targets", JP2009521934 (A), Espacenet, (2009). Abstract.

GenBank Accession No. NM_133475.1, "*Homo sapiens* Ankyrin Repeat Domain 24 (ANKRD24), mRNA", (2007).

GenBank Accession No. BF772662.1, "CM4-IT0042-131200-611-h08 IT0042 *Homo sapiens* cDNA, mRNA Sequence.", (2001).

Saunders, L., et al., "Sirtuins: Critical Regulators at the Crossroads Between Cancer and Aging", Oncogene, vol. 26, pp. 5489-5504, (2007).

Kuehbacher, A., et al., "Abstract 5443: MicroRNA 92a Controls Vessel Growth and Functional Recovery After Ischemia", Circulation, vol. 118, S_550, (2008).

Mostoslavsky, R., et al., "Genomic Instability and Aging-like Phenotype in the Absence of Mammalian SIRT6", Cell, vol. 124, No. 2, pp. 315-329, (2006).

Sun, Y., et al., "Down Syndrome Candidate Region 1 Increases the Stability of the IkBx Protein", The Journal of Biological Chemistry, vol. 281, No. 51, pp. 39051-39061, (2006).

GenBank Accession No. DQ_576648, "*Homo sapiens* piRNA-44760 Complete Sequence.", (2006).

GenBank Accession No. AJU_95541, "Human BCR Target Sequence SEQ ID No. 5051.", (2007).

GenBank Accession No. AXA_68544, "Human Genome Sequence PCR Primer Sequence ID No. 74973.", (2009).

GenBank Accession No. AED81100, "Inhibitors of Human Plasmin Derived from the Kunitz Domains." (2011).

Yamamoto, H., et al., "Sirtuin Functions in Health and Disease", Molecular Endocrinology, vol. 21, No. 8, pp. 1745-1755, (2007).

\* cited by examiner

TREATMENT OF SIRTUIN (SIRT) RELATED DISEASES BY INHIBITION OF NATURAL ANTISENSE TRANSCRIPT TO A SIRTUIN (SIRT)

The present application is a Continuation of U.S. Ser. No. 13/386,057 filed on Jan. 20, 2012, which is a National Phase filing of PCT/US2010/043075 filed on Jul. 23, 2010, which is a Continuation-in-part of application No. PCT/US2009066445 filed on Dec. 2, 2009, which is a Continuation-in-part of application No. PCT/US2010/026119 filed Mar. 3, 2010, which claims priority to U.S. Provisional No. 61/259,072 filed on Nov. 6, 2009 and U.S. Provisional No. 61/228,392 filed on Jul. 24, 2009, which are all incorporated herein by reference in their entireties.

FIELD OF THE INVENTION

Embodiments of the invention comprise oligonucleotides modulating expression and/or function of a Sirtuin (SIRT) and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

In one embodiment, the invention provides methods for inhibiting the action of a natural antisense transcript by using antisense oligonucleotides(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of a Sirtuin (SIRT) polynucleotides in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within the nucleotides 1 to 1028 of SEQ ID NO: 5 or nucleotides 1 to 429 of SEQ ID NO: 6, or nucleotides 1 to 156 of SEQ ID NO: 7 or nucleotides 1 to 593 of SEQ ID NOs:8, 1 to 373 of SEQ ID NO: 9, 1 to 1713 of SEQ ID NO: 10, 1 to 660 of SEQ ID NO: 11, 1 to 589 of SEQ ID NO: 12, 1 to 428 of SEQ ID NO: 13 and 1 to 4041 of SEQ ID NO: 14 thereby modulating function and/or expression of the Sirtuin (SIRT) polynucleotide in patient cells or tissues in vivo or in vitro.

In another embodiment, an oligonucleotide targets a natural antisense sequence of a Sirtuin (SIRT) polynucleotide, for example, nucleotides set forth in SEQ ID NO: 5 to 14, and any variants, alleles, homologs, mutants, derivatives, fragments and complementary sequences thereto. Examples of antisense oligonucleotides are set forth as SEQ ID NOS: 15 to 94.

Another embodiment provides a method of modulating function and/or expression of a Sirtuin (SIRT) polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the Sirtuin (SIR) polynucleotide: thereby modulating function and/or expression of the Sirtuin (SIRT) polynucleotide in patient cells or tissues in vivo or in vitro.

Another embodiment provides a method of modulating function and/or expression of a Sirtuin (SIRT) polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to a Sirtuin (SIRT) antisense polynuceotide; thereby modulating function and/or expression of the Sirtuin (SIRT) polynucleotide in patient cells or tissues in vivo or in vitro.

In one embodiment, a composition comprises one or more antisense oligonucleotides which bind to sense and/or antisense Sirtuin (SIRT) polynucleotides.

In another embodiment, the oligonucleotides comprise one or more modified or substituted nucleotides.

In another embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another embodiment, the oligonucleotides are administered to a patient subcutaneously, intramuscularly, intravenously or intraperitoneally.

In another embodiment, the oligonucleotides are administered in pharmaceutical composition. A treatment regimen comprises administering the antisense compounds at least once to patient; however, this treatment can be modified to include multiple doses over a period of time. The treatment can be combined with one or more other types of therapies.

In another embodiment, the oligonucleotides are encapsulated in a liposome or attached to a carrier molecule (e.g. cholesterol, TAT peptide).

Other aspects are described infra.

SEQUENCE LISTING DESCRIPTION

Figure 1:
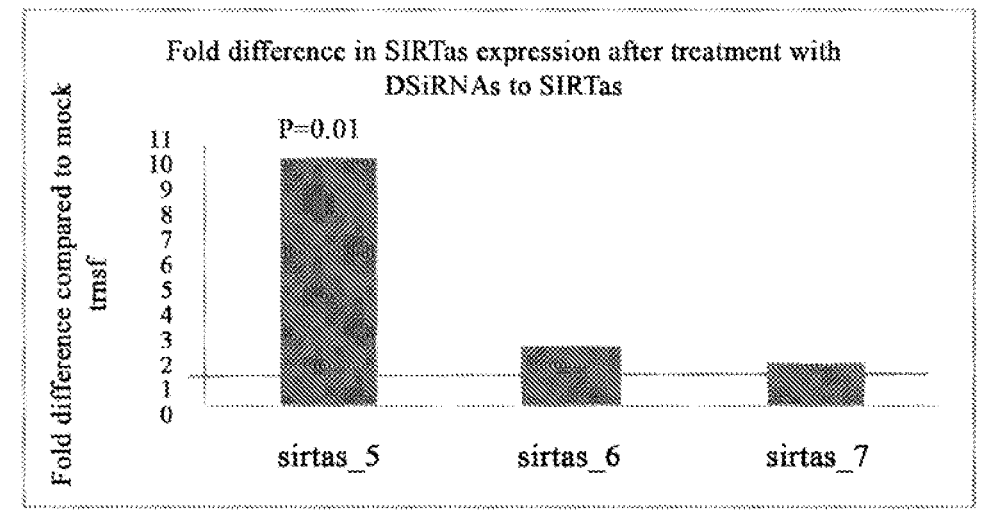
FIGS. 1 and 2 show Real time PCR results of oligonucleotides designed to SIRT antisense CV396200. The results show that the levels of the SIRT1 mRNA in HepG2 cells are significantly increased 48 h after treatment with one of the siRNAs designed to sirtas (sirtas_5, P=0.01). In the same samples the levels of sirtas RNA were significantly decreased after treatment with sirtas_5, but unchanged after treatment with sirtas_6 and sirtas_7, which also had no effect on the SIRT1 mRNA levels (FIG. 2), sirtas_5, sirtas_6 and sirtas_7 correspond to SEQ ID NOs: 38, 39 and 40 respectively.

SEQ ID NO: 1: Homo sapiens sirtuin (silent mating type information regulation 2 homolog) 1 (*S. cerevisiae*) (SIRT1), mRNA (NCBI Accession Number: NM_012238.3)

SEQ ID NO: 2: Mus musculus sirtuin 1 (silent mating type information regulation 2, homolog) 1 (*S. cerevisiae*) (SIRT1) mRNA (NCBI Accession Number: NM_001159589)

SEQ ID NO: 3: Homo sapiens sirtuin (silent tracing type information regulation 2 homolog) 3 (*S. cerevisiae*) (SIRT3), transcript variant 1, mRNA (NCBI Accession No.: NM_012239.5).

SEQ ID NO: 4: Homo sapiens sirtuin 6 (SIRT6), transcript variant 1, mRNA (NCBI Accession No.: NM_016539).

SEQ ID NO: 5: Expanded natural antisense sequence (CV396200—expanded)

SEQ ID NO: 6: Natural Antisense sequence (CV428275)

SEQ ID NO: 7: Natural Antisense Sequence (BE717453)

SEQ ID NO: 8: Natural Antisense Sequence (AV7188812)

SEQ ID NO: 9: Natural SIRT1 antisense sequence (AW169958)

SEQ ID NO: 10 Natural SIRT1 mouse antisense sequence (AK044604)

SEQ ID NO: 11: Natural SIRT3 antisense sequence (Hs.683117)

SEQ ID NO: 12: Natural SIRT3 antisense sequence (DA645474)

SEQ ID NO: 13: Natural SIRT6 antisense sequence (BF772662)

SEQ ID NO: 14: Natural SIRT6 antisense sequence (ANKRD24)

SEQ ID NOs: 15 to 94: Antisense oligonucleotides. * indicates phosphothioate bond, +indicates LNA and m indicates 2'O Me.

SEQ ID NO: 95 to 98-SEQ ID NO: 95 correspond to the exon 4 of the SIRT1 natural antisense CV396200, SEQ ID NO: 96, 97 and 98 correspond to the forward primer sequence, reverse primer sequence and the reporter sequence respectively.

SEQ ID NO: 99 corresponds to CUR 962, * indicates phosphothioate bond and +indicates LNA.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognise that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In embodiments, the genes or nucleic acid sequences are human.

Definitions

The terminology used herein is for the purpose of describing particular embodiments only and is not intended to be limiting of the invention. As used herein, the singular forma "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can means an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleotides and/or oligonucleotide analogs as described above.

The oligonucleotide can be composed of regions that can be linked in "register" that is, when the monomers are linked consecutively, as in native DNA, or linked via spacers. The spacers are intended to constitute a covalent "bridge" between the regions and have is cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "Sirtuins (SIRT)s" are inclusive of all family members, mutants, alleles, fragments, species, coding and noncoding sequences, sense and antisense polynucleotide strands, etc.

As used herein, the words Sirtuin1, SIRT1, sirtuin, silent mating type information regulation 2 homolog 1, hSIR2, hSIRT1, NAD-dependent deacetylase sirtuin-1, SIR2L1, SIR2-like protein 1, are considered the same in the literature and are used interchangeable in the present application.

As used herein, the words 'Sirtuin 3', Sirtuin3, Sirtuin-3, SIRT3, SIRT-3, hSIRT3, NAD-dependent deacetylase sirtuin-3, mitochondrial, SIR2L3, SIR2-like protein 3 are used interchangeable in the present application.

As used herein, the words 'Sirtuin6', Sirtuin6, Sirtuin-6, SIRT6, SIRT-6, NAD-dependent deacetylase sirtuin-6, SIR2L6, SIR2-like protein 6 are considered the same in the literature and are used interchangeable in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interfers with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments of the present invention, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a object to be controlled and a lower degree of complementarity to corresponding nucleic acid sequences in other species. One skilled in the art will realise that there is considerable latitude in selecting appropriate regions of genes for use in the present invention.

By "enzymatic RNA" is meant as RNA molecule with enzymatic activity. Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognises and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA. This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphomates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynyleytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in U.S. Pat. No. 5,432,272. The term "nucleotide" is intended to cover every and all of these examples as well as analogues and (tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties. Such analogs include synthetic nucleotides designed to enhance binding properties, e.g. duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vivo assays.

As used herein, the phrase "stringent hybridization conditions" or "stringent conditions" refers to conditions under which a compound of the invention will hybridise to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (>0.15M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridise over one or more segments such that intervening or adjacent segments are not involved in the hybridization event (e.g., a loop structure, mismatch or hairpin structure). The oligomeric compounds of the present invention comprise at least about 70%, or at least about 75% or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art. Percent homology, sequence identity or complementarity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilising agents such as formamide.

As used herein, "modulation" means either an increase (stimulation) or a decrease (inhibition) in the expression of a gene.

The term "variant," what used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic add sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, mix, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, "cancer" refers to all types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Neurological disease or disorder" refers to any disease or disorder of the nervous system and/or visual system, "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasma, neuroopthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegicetasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral anterisclerosis; cerebral atrophy; cerebral gigantism; cerebral palsy; Charcot-Marie-Tooth disease; chemotherapy-induced neuropathy and neuropathic pain; Chiani malformation; chorea; chronic inflammatory demyelinating polyneuropathy; chronic pain; chronic regional pain syndrome; Coffin Lowry syndrome; coma, including persistent vegetative state; cogenital facial diplegia; corticobasal degeneration; cranial arteritis; craniosynostosis; Creutazfeldt-Jakob disease; cumulative trauma disorders; Cushing's syndrome; cytomegalic inclusion body disease: cytomegalovirus infection; dancing eyes-dancing feet syndrome; Dandy Walker syndrome; Dawson disease; De Morsier's syndrome; Dejerine-Klumke palsy; dementia; dermatomyositis; diabetic neuropathy; diffuse sclerosis; dysantonomia; dysgraphia; dyslexia; dystonias; early infantile epileptic encephalopathy; empty sella syndrome; encephalitis, encephaloccles; encephalotrigeminal angiomatosis; epilepsy; Erb's palsy; essential tremor; Fabry's disease; Fahr's syndrome; fainting, familial spastic paralysis; febrile seizures, Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myclopathy; Hallervorden-Spatz disease; head injury; headache; hemifacial spasm; hereditary spastic paraplegia; herodopathia atactic a polyneuritiformis; herpes zoster oticus; herpes zoster; Hirayama syndrome; HIV associated dementia and neuropathy (also neurological manifestations of AIDS); holoprosencephaly; Huntington's disease and other polyglutamine repeat diseases; hydranencelphaly; hydrocephalus; hypercortisolism; hypoxia, immune-mediated encephalomyelitis; inclusion body myositis; incontinentia pigmenti; infantile phytanic acid storage disease; infantile refsum disease, infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kunr; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease, (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Meineres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse selerosis; myoclonic encephalopathy of infants; myoclonus; myopathy; myotonia congenital; narcolepsy; neurofibromatosis; neuroleptic malignant syndrome; neurological manifestations of AIDS; neurological sequelae oflupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtarhara syndrome; olivopontocerebellar atrophy; opsoclouus myoclonus; optic neuritis, orthostatic hypotension, overuse syndrome; paresthia; Neurodegenerative disease or disorder (Parkinson's disease, Huntington's disease, Alzheimer's disease, amyotrophic lateral scelerosis (ALS), dementia multiple scelerosis and other diseases and disorders associated with neuronal cell death); paramyotonia congenital; paraneoplastic diseases, paroxysmal attacks; Parry Romberg syndrome; Pelizacus-Merzbacher disease; periodic paralyses; peripheral neuropathy; painful neuropathy and neuropathic pain: persistent vegetative state; pervasive developmental disorders; photic sneeze reflex; phytanic acid storage disease; Pick's disease: pinched nerve: pituitary tumors; polymyositis polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocallcukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomson disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Wallenberg's syndrome; Werdnig-Hoffman disease; West syndrome; whiplash; Williams syndrome; Wildon's disease; and Zellweger syndrome.

"Metabolic disease" refers to a wide range of diseases and disorders of the endocrine system including, for example, insulin resistance, diabetes, obesity, impaired glucose tolerance, high blood cholesterol, hyperglycemia, dyslipidemia and hyperlipidemia.

An "Inflammation" refers to systemic inflammatory conditions and additions associated locally with migration and attraction of monocytes, leukocytes and/or neutrophils. Examples of inflammation include, but are not limited to. Inflammation resulting from infection with pathogenic organisms (including gram-positive bacteria, gram-negative bacteria, viruses, fungi, and parasites, such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction. Allergic reactions include allergic asthma, chronic bronchitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques. Inflammation includes, but is not limited to, Non-Hodgkin's lymphoma, Wegener's granulomatosis, Hashimoto's thyroiditis, hepatocellular carcinoma, thymus atrophy, chronic pancreatitis, rheumatoid arthritis, reactive lymphoid hyperplasia, osteoarthritis, ulcerative colitis, papillary carcinoma, Crohn's disease, ulcerative colitis, acute cholecystitis, chronic cholecystitis, cirrhosis, chronic sialadentis, peritonitis, acute pancreatitis, chronic pancreatitis, chronic Gastritis, adenomyosis, endometriosis, acute cervicitis, chronic cervicitis, lymphoid hyperplasia, multiple sclerosis, hypertrophy secondary to idiopathic thrombocytopenic purpura, primary IgA nephropathy, systemic lupus erythematosus, psoriasis, pulmonary emphysema, chronic pyclonephritis, and chronic cystitis.

A cardiovascular disease or disorder includes those disorders that can either cause ischemia or are caused by reperfusion of the heart. Examples include, but are not limited to, atheroscerosis, coronary artery disease, granulomatous myocarditis, chronic myocarditis (non-granulomatous), primary hypertrophic cardiomyopathy, peripheral artery disease (PAD), stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to Sirtuin3 activation, CVS diseases include, but are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

Polynucleotide and Oligonucleotide Compositions and Molecules

Targets

In one embodiment, the targets comprise nucleic acid sequences of a Sirtuin (SIRT), including without limitation sense and/or antisense noncoding and/or coding sequences associated with a Sirtuin (SIRT).

In one embodiment, the targets comprise nucleic acid sequences of SIRT1, including without limitation sense and/or antisense noncoding and/or coding sequences associated with SIRT1 gene.

In one embodiment, the targets comprise nucleic acid, sequences of SIRT3, including without limitation sense and/or antisense noncoding and/or coding sequences associated with SIRT3 gene.

In one embodiment, the targets comprise nucleic acid sequences of SIRT6, including without limitation sense and/or antisense noncoding and/or coding sequences associated with SIRT6 gene.

"SIRT1 protein" refers to a member of the sir2 family of sirtuin deacetylases. In one embodiment, a SIRT1 protein includes yeast Sir2 (GenBank Accession No. P53685). C. elegans Sir-2.1 (GenBank Accession No. NP.sub.-501912), human SIRT1 (GenBank Accession No. NM.sub.-012238 and NP.sub.-036370 (or AF083106))

SIRT1 "Sirtuins" are proteins that include a SIR2 domain, a domain defined as amino acids sequences that are scored as hits in the Pfam family "SIR2"-PF02146 (attached to the Appendix). This family is referenced in the INTERPRO database as INTERPRO description (entry IFR003000). To identify the presence of a "SIR2" domain in a protein sequence, and make the determination that a polypeptide or protein of interest has a particular profile, the amino acid sequence of the protein can be searched against the Pfam database of HMMs (e.g., the Pfam database, release 9) using the default parameters (http://www.sanger.ac.uk/Software/Pfam/HMM_search). The SIR2 domain is indexed in Pfam as PF02146 and in INTERPRO as INTERPRO description (entry IPR003000). A description of the Pfam database can be found in "The Pfam Protein Families Database" Bateman A et al. (2002) Nucleic Acids Research 30(1):276-280 and Sonhammer et al. (1997) Proteins 28(3):405-420 and a detailed description of HMMs can be found, for example, in Gribskov et al. (1990) Meth. Enzymol. 183:146-159; Gribskov et al. (1987) Proc Natl. Acad. Sci. USA 84:4355-4358; Krogh et al. (1994) J. Mol. Biol. 235:1501-1531; and Stultz et al. (1993) Protein Sci. 2:306-314.

Among the mitochondrial sirtuins, SIRT3 possesses the most robust deacetylase activity. Indeed, significantly higher levels of mitochondrial protein acetylation were detected in the livers of SIRT3-null mice, compared to those of SIRT4 or SIRT5 knockout animals. However, little is known about the physiological role of SIRT3 despite the fact that a number of SIRT3 substrates and co-precipitating proteins have been identified; acetyl-CoA synthetase 2, Kn70, FOXO3a, subunit 9 of mitochondrial Complex 1 (NDUFA9), glutamate dehydrogenase and isocitrate dehydrogenase 2.

SIRT3 is a major mitochondrial deacetylase. Mitochondrial proteins show hyperacetylation in SIRT3 knockout mice, but not in SIRT4 or SIRT5 knockout mice. Acetyl-CoA synthetase 2 (AceCS2), a mitochondrial enzyme that converts acetate into acetyl-CoA, was the first mitochondrial substrate of SIRT3 identified. Deacetylation of AceCS2 at lysine 642 by SIRT3 activates acetyl-CoA synthetase activity, providing increased acetyl-CoA to feed into the tricarboxylic acid cycle. Glutamate dehydrogenase (GDH), another mitochondrial protein involved in energy production, is deacetylated by SIRT3, GDH can also be ADP-ribosylated by SIRT4 in turn to decrease its enzyme activity. This indicates that SIRT3 could play an important role in cell metabolism. SIRT3 has also been shown to be involved in selective apoptosis pathways and cell growth control. SIRT3 and SIRT4, but not SIRT5, have been implicated in the NAD+ salvage pathway that regulates the NAD+ level relating to cell survival. In addition, variability in the hSIRT3 gene has been linked to human longevity.

The Silent Information Regulator-2 gene (Sir2) encodes an NAD-dependent histone deacetylase that links regulation of chromatin, genomic stability, and life span in *S. cerevisiae*. By promoting chromatin silencing, Sir2 inhibits transcription at several genetic loci and represses recombination at ribosomal DNA (rDNA) repeats. Yeast with mutations in Sir2 have increased genomic instability is the context of rDNA recombination, which in turn shortens replicative life span—a marker of reproductive aging in this organism. Conversely, extracopies of Sir2 that suppress rDNA recombination increase replicative life span. These effects of Sir2 suggest paradigms in which genes that promote genome stabilization through chromatin modulation may be important contributors to regulation of organismal life span, aging, and age-related pathology.

Consistent with a conserved role for Sir2 factors in life span regulation, increased activity of Sir2 proteins in the multicellular organisms *C. elegans* and *D. melanogaster* also increases life span. However, these Sir2 factors may operate through mechanisms that are independent of genome stabilization, and their physiologic molecular substrates are still unclear. In mammals, there are seven Sir2 family members, SIRT1-SIRT7. The SIRTs have been of great interest as candidate regulators of mammalian life span and aging-related processes. In this context, several mammalian SIRTs have functions that impact on aging-associated molecular pathways and disease. However, initial studies of mammalian SIRTs linked these enzymes to biochemical targets and cellular functions that are distinct from those of *S. cerevisiae* Sir2.

The generation of mice deficient for the mammalian SIRT6 gene revealed a potential role tor SIRT6 in linking regulation of life span, chromatin, and genomic stability. In this context SIRT6 deficiency in mice leads to dramatically shortened life span and acute degenerative phenotypes that overlap with pathologies of premature aging. Moreover, SIRT6 knockout mouse cells have genomic instability and DNA damage hypersensitivity. In biochemical fractionation assays. SIRT6 protein associates preferentially with a chromatin-enriched cellular fraction. Together, these observations suggested that SIRT6 might couple chromatin regulation with DNA repair. However, a physiologic role for SIRT6 in such a process has not yet been demonstrated.

In some embodiments, antisense oligonucleotides are used to prevent or treat diseases or disorders associated with Sirtuin (SIRT) family members. Exemplary Sirtuin (SIRT) mediated diseases and disorders which can be treated with cell/tissues regenerated from stem cells obtained using the antisense compounds comprise: cancer (e.g., breast cancer, colorectal cancer, CCL, CML, prostate cancer), a neurodegenerative disease or disorder (e.g., Alzheimers Disease (AD), Huntington's disease, Parkinson's disease. Amyotrophic Lateral Sclerosis (ALS), Multiple Sclerosis, and disorders caused by polyglutamine aggregation); skeletal muscle disease (e.g., Duchene muscular dystrophy, skeletal muscle atrophy, Becker's dystrophy, or myotonic dystrophy); a metabolic disease or disorder (e.g., insulin resistance, diabetes, type 2 diabetes, obesity, impaired glucose tolerance, metabolic syndrome, adult-onset diabetes, diabetic nephropathy, hyperglycemia, diabetic nephropathy, Hypercholesterolemia, dyslipidemia hyperlipidemia and an age-related metabolic disease etc.), a disease or disorder associated with impaired regulation of insulin level, neuropathy e.g., sensory neuropathy, autonomic neuropathy, motor neuropathy, retinopathy), a disease or disorder associated with a ketogenic condition, a disease or disorder associated with impaired energy homeostasis, a disease or disorder associated with impaired Acetyl-CoA synthetase 2 activity, a disease or disorder associated with metabolic homeostasis, a lipid metabolism disease or disorder, a disease or disorder associated with impaired thermogenesis, a disease or disorder associated with mitochondrial dysfunction, neuropathy (e.g., sensory neuropathy, autonomic neuropathy, motor neuropathy, retinopathy), a liver disease (e.g., due to alcohol abuse or hepatitis, fatty liver disease etc.); age-related macular degeneration, bone disease (e.g., osteoporosis), a blood disease (e.g., a leukemia); liver disease (e.g., due to alcohol abuse or hepatitis); obesity; bone resorption, age-related macular degeneration, AIDS related dementia, ALS, Bell's Palsy, atherosclerosis, a cardiac disease (e.g., cardiac dysrhymias, chronic congestive heart failure, ischemic stroke, coronary artery disease and cardiomyopathy), chronically degenerative disease (e.g., cardiac muscle disease), chronic renal failure, type 2 diabetes, ulcerations, cataract, presbiopia, glomerulenephritis, Guillan-Barre syndrome, hemorrhagic stroke, rheumatoid arthritis, inflammatory bowel disease, SLE, Crohn's disease, osteoarthritis, osteoporosis, Chronic Obstructive Pulmonary Disease (COPD), pneumonia, skin aging, urinary incontinence, a disease or disorder associated with mitochondrial dysfunction (e.g., mitochondrial myopathy, encephalopathy, Leber's disease, Leigh encephalopathia, Pearson's disease, lactic acidosis, 'mitochondrial encephalopathy, lactic acidosis and stroke like symptoms' (MELAS) etc.) and a disease or disorder associated with neuronal cell death, degenerative syndrome, aging, a disease or disorder associated with telomere dysfunction, a disease or disorder associated with impaired chromatin regulation, a disease or disorder associated with premature cellular senescence, a disease or disorder associated with impared SIRT6 mediated DNA repair and a condition characterized by unwanted cell loss.

In another embodiment, the antisense oligonucleotides modulate the normal expression and/or normal function of a Sirtuin (SIRT) in patients suffering from or at risk of developing diseases or disorders associated with Sirtuin (SIRT).

In embodiments of the present invention, therapeutic and/or cosmetic regimes and related tailored treatments are provided to subjects requiring skin treatments or at risk of developing conditions for which they would require skin treatments. Diagnosis can be made e.g., based on the subject's SIRT status. A patient's SIRT expression levels in a given tissue such as skin can be determined by methods known to those of skill in the art and described elsewhere herein, e.g., by analysing tissue using PCR or antibody-based detection methods.

A preferred embodiment of the present invention provides a composition for skin treatment and/or a cosmetic application comprising SIRT antisense oligonucleotides, e.g., to upregulate expression of SIRT in the skin. Examples of antisense oligonucleotides are set forth as SEQ ID NOS: 4 to 16. U.S. Pat. No. 7,544,497, "Compositions for manipulating the lifespan and stress response of cells and organisms," incorporated herein by reference, describes potential cosmetic use for agents that modulate Sirtuin activity by reducing the $K_m$ of the Sirtuin protein for its substrate. In embodiments, cells are treated in vivo with the oligonucleotides of the present invention, to increase cell lifespan or prevent apoptesis. For example, skin can be protected from aging, e.g., developing wrinkles, by treating skin, e.g., epithelial cells, as described herein. In an exemplary embodiment, skin is contacted with a pharmaceutical or cosmetic composition comprising a SIRT antisense compound as described herein. Exemplary skin afflictions or skin conditions include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, skin cancer and the effects of natural aging.

Sirtuin has been reported to interfere with dihydrotestosterone-induced androgen receptor signaling. (See, e.g., Fu, et al., 2006, "Hormonal Control of Androgen Receptor Function through SIRT1," Molecular and Cellular Biology 26(21): 8122-8135, incorporated herein by reference.) In embodiments of the present invention, a composition comprising SIRT antisense oligonucleotides, e.g., to upregulate expression of SIRT in the scalp and inhibit androgen receptor signaling, thereby preventing androgenetic alopecia (hair loss). In embodiments, a patient suffering from alopecia is administered either a topical or systemic formulation.

In an embodiment, an antisense oligonucleotide described herein is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable to the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, sarabens, waxes, and the like. Formulations may be colorless, odorless ointments, lotions, creams, microemulsions and gels.

Antisense oligonucleotides of the invention, may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's Pharmaceutical Sciences (Mack Pub. Co.), ointment bases may be grouped into four classes: oleagineous bases; emulsifiable bases; emulsion bases; and water-soluble bases. Oleaginous ointment bases include, for example, vegetable oils, fats obtained from animals, and semisolid hydrocarbon obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight (see, e.g., Remington's, supra).

Antisense oligonucleotides of the invention may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localising and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor.sup™ from Beiersdorf, Inc. (Norwalk, Conn.).

Antisense oligonucleotides of the invention may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Antisense oligonucleotides of the invention may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolyglycerides. The water phase includes not only water but also, typically, buffers, glucose, propylene glycol polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Antisense oligonucleotides of the invention may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5% sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g. topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilisers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer senses to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoside (C.sub.10 MSO) and tetradecylmethyl sulfoxide; pyrrolidones such as 2-pyrrolidone, N-methyl-2-pyrrolidone and N-(-hydroxyethyl)pyrrolidone; urea; N,N-diethyl-m-toluamide; C.sub.2-C.sub.6 alkanediols; miscellaneous solvents such as dimethyl formamide (DMF), N,N-dimethylacetamide (DMA) and tetrahydrofurfuryl alcohol; and the 1-substituted azcycloheptan-2-ones, particularly 1-n-dodecylecyclazacycloheptan-2-one (laurocapram; available under the trademark Azone.sup™ from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol.sup™) and diethylene glycol monoethyl ether oleate (available commercially as Soficutol.sup™); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 500, and polyethylene glycol derivatives such as PEG-8 caprylic/capric glycerides (available commercially as Labrasol.sup™); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g.; other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In one embodiment, the oligonucleotides are specific for polynucleotides of a Sirtuin (SIRT), which includes, without limitation noncoding regions. The Sirtuin (SIRT) targets comprise variants of a Sirtuin (SIRT); mutants of a Sirtuin (SIRT), including SNPs; noncoding sequences of a Sirtuin (SIRT); alleles, fragments and the like. Preferably the oligonucleotide is an antisense RNA molecule.

In accordance with embodiments of the invention, the target nucleic acid molecule is not limited to a Sirtuin (SIRT) polynucleotides alone but extends to any of the isoforms, receptors, homologs, non-coding regions and the like of a Sirtuin (SIRT).

In another embodiment, an oligonucleotide targets a natural antisense sequence (natural antisense to the coding and non-coding regions) of a Sirtuin (SIRT) targets, including, without limitation, variants, alleles, homologs, mutants, derivatives, fragments and complementary sequences thereto. Preferably the oligonucleotide is an antisense RNA or DNA molecule.

In another embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound.

In some embodiments, homology, sequence identity or complementarity; between the antisense compound and target is from about 50% to about 60%. In some embodiments, homology, sequence identity or complementarity, is from about 60% to about 79%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to a target sequences under conditions in which specific binding is desired, i.e., under physiological conditions in the case of in vivo assays or therapeutic treatment, and in the case of in vitro assays, under conditions in which the assays are performed.

In another embodiment, targeting of a Sirtuin (SIRT) including without limitation, antisense sequences which are identified and expanded, using for example, PCR, hybridization etc., one or more of the sequences set forth as SEQ ID NO: 5 to 14, and the like, modulate the expression or function of a Sirtuin (SIRT). In one embodiment, expression or function is up-regulated as compared to a control. In another embodiment, expression or function is down-regulated as compared to a control.

In another embodiment, oligonucleotides comprise nucleic acid sequences set forth as SEQ ID NOS: 15 to 94 including antisense sequences which are identified and expanded, using for example, PCR, hybridization etc. These oligonucleotides can comprise one or more modified nucleotides, shorten or longer fragments, modified, bonds and the like. Examples of modified bonds or internucleotide linkages comprise phosphorothioate, phosphorodithioate or the like. In another embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes a Sirtuin (SIRT).

The targeting process usually also includes determination of at least one target region, segment or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In one embodiment, the antisense oligonucleotides bind to the natural antisense sequences of a Sirtuin (SIRT) and modulate the expression and/or function of a Sirtuin (SIRT) (SEQ ID NO: 1 to 3). Examples of antisense sequences include SEQ ID NOS: 4 to 29.

In another embodiment, the antisense oligonucleotides bind to one or more segments of a Sirtuin (SIRT) polynucleotide and modulate the expression and/or function of a Sirtuin (SIRT). The segments comprise at least five consecutive nucleotides of a Sirtuin (SIRT) sense or antisense polynucleotides.

In another embodiment, the antisense oligonucleotides are specific for natural antisense sequences of a Sirtuin (SIRT) wherein binding of the oligonucleotides to the natural antisense sequences of a Sirtuin (SIRT) modulate expression and/or function of a Sirtuin (SIRT).

In another embodiment, oligonucleotide compounds comprise sequences set forth as SEQ ID NOS: 15 to 94, antisense sequences which are identified and expanded, using for example, PCR, hybridization etc These oligonucleotides can comprise one or more modified nucleotides, shorter or longer fragments, modified bonds and the like. Examples of modified bonds or internucleotide linkages comprise phosphorothioate, phosphorodithioate or the like. In another embodiment, the nucleotides comprise a phosphorus derivative. The phosphorus derivative (or modified phosphate group) which may be attached to the sugar or sugar analog moiety in the modified oligonucleotides of the present invention, may be a monophosphate, diphosphate, triphosphate; alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known its the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilised, for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a Sirtuin (SIRT), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation, termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codes, and thus including nucleotides between the 5' cap site and the translation initiation codon of an mRNA (or corresponding nucleotides on the gene). Still another target region includes the 3'-untranslated region (3'UTR), known in the art to refer to the portion of an mRNA in the 3' direction from the translation termination codon, and thus including nucleotides between the translation termination codes and 3' end of an mRNA (or corresponding nucleotides on the gene). The 5' cap site of an mRNA comprises an N7-methylated guanosine residue joined to the 5'-most residue of the mRNA via a 5'-5'triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another embodiment, the antisense oligonucleotides bind to coding and/or non-coding regions of a target polynucleotide and modulate the expression and/or function of the target molecule.

In another embodiment, the antisense oligonucleotides bind to natural antisense polynucleotides and modulate the expression and/or fraction of the target molecule.

In another embodiment, the antisense oligonucleotides bind to sense polynucleotides and modulate the expression and/or function of the target molecule.

Alternative RNA transcripts, can be produced from the same genomic region of DNA. These alternative transcripts are generally known as "variants". More specifically, "pre-mRNA variants" are transcripts produced from the same genomic DNA that differ from other transcript produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more to one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative target segments are considered to be suitable for targeting as well.

Target segments can include DNA or RNA sequences that comprise at least the 5 consecutive nucleotides from the 5'-terminus of one of the illustrative target segments (the remaining nucleotides being a consecutive stretch of the same DNA or RNA beginning immediately upstream of the 5'-terminus of the target segment and continuing until the DNA or RNA contains about 5 to about 100 nucleotides). Similarly target segments are represented by DNA or RNA sequences that comprise at least the 5 consecutive nucleotides from the 3'-terminus of one of the illustrative target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further target segments.

Once one or more target regions, segments or sites have been identified, antisense compounds are chosen which are sufficiently complementary to the target, i.e., hybridise sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, specific nucleic acids are targeted by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise micro-RNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused, on polyadenylated mRNAs that are processed and exported to the cytoplasm. Recently, it was shown to the set of non-polyadenylated nuclear RNAs may be very large, and that many such transcripts arise from intergenic regions. The mechanism by which ncRNAs may regulate gene expression is by base pairing with target transcripts. The RNAs that function by base pairing can be grouped into (1) cis encoded RNAs to are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting to its knockdown or sequestration. Coding as well as non-coding antisense can be targeted in an identical manner and to either category is capable of regulating the corresponding sense transcripts—either in a concordant or disconcordant manner. The strategies that are employed in identifying new nucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If for example, an antisense oligonucleotide is used to achieve knockdown, then this strategy can be used to apply one antisense oligonucleotide targeted to the sense transcript and corner antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DMA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids including oligonucleotides) may be described as "DNA-like" (i.e., generally having one or more 2'-deoxy sugars and generally, T rather than U bases) or "RNA-like" (i.e., generally having one or more 2'-hydroxyl or 2'-modified sugars and generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (siRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoter induce potent transcription activation of associated genes. RNAa was demonstrated in human cells using synthetic dsRNAs, termed "small activating RNAs" (saRNAs).

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing. However, in instances described in detail in the examples section which follows, oligonucleotides are shown to increase the expression and/or function, of the Sirtuin (SIRT) polynucleotides and encoded products thereof dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "target segments" identified herein may be employed in a screen for additional compounds that modulate the expression of a Sirtuin (SIRT) polynucleotide. "Modulators" are those compounds that decrease or increase the expression of a nucleic acid molecule encoding a Sirtuin (SIRT) and which comprise at least a nucleotide portion that is complementary to a target segment. The screening method comprises the steps of contacting a target segment of a nucleic acid molecule encoding sense or natural antisense polynucleotides of a Sirtuin (SIRT) with one or more candidate modulators, and selecting for one or more candidate modulate which decrease or increase the expression of a nucleic acid molecule encoding a Sirtuin (SIRT) polynucleotide, e.g. SEQ ID NOS: 15 to 94. Once it is shown that the candidate modulator or modulators are capable of modulating (e.g. either decreasing or increasing) the expression of a nucleic acid molecule encoding a Sirtuin (SIRT) polynucleotide, the modulator may then be employed in further investigative studies of the function, of a Sirtuin (SIRT) polynucleotide, or for use as a research, diagnostic, or therapeutic agent in accordance with the present invention.

Targeting the natural antisense sequence modulates the function of the target gene. For example, the Sirtuin (SIRT) (e.g. accession numbers NM_012238.3, NM_001159589, NM_012239, NM_016539). In a embodiment, the target is an antisense polynucleotide of the Sirtuin (SIRT). In a embodiment, an antisense oligonucleotide targets sense and/or natural antisense sequences of a Sirtuin (SIRT) polynucleotide (e.g. accession, numbers NM_012238.3, NM_0011-59589, NM_012239, NM_016539), variants, alleles, isoforms, homologs, mutants, derivatives, fragments and complementary sequences thereto. Preferably the oligonucleotide is an antisense molecule and the targets include coding and noncoding regions of antisense and/or sense Sirtuin (SIRT) polynucleotides.

The target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications. For example, such double-stranded moieties have been shown to inhibit the target by the classical hybridization of antisense strand of the duplex to the target, thereby triggering enzymatic degradation of the target.

In a embodiment, an antisense oligonucleotide targets Sirtuin (SIRT) polynucleotides (e.g. accession numbers NM_012238.3, NM_001159589, NM_012239, NM_016539), variants, alleles, isoforms, homologs, mutants, derivatives, fragments and complementary sequences thereto. Preferably the oligonucleotide is an antisense molecule.

In accordance with embodiments of the invention, the target nucleic molecule is not limited to Sirtuin (SIRT) alone but extends to any of the isoforms, receptors, homologs and the like of a Sirtuin (SIRT) molecule.

In another embodiment, an oligonucleotides targets a natural antisense sequence of a Sirtuin (SIRT) polynucleotide, for example, polynucleotides set forth as SEQ ID NO: 5 to 14, and any variants, alleles, homologs, mutants, derivatives, fragments and complementary sequences thereto. Examples of antisense oligonucleotides are set forth as SEQ ID NOS: 15 to 94.

In one embodiment, the oligonucleotides are complementary to or bind to nucleic acid sequences of a Sirtuin (SIRT) antisense, including without limitation noncoding sense and/or antisense sequences associated with a Sirtuin (SIRT) polynucleotide and modular expression and/or function of a Sirtuin (SIRT) molecule.

In another embodiment, the oligonucleotides are complementary to or bind to nucleic acid sequences of a Sirtuin (SIRT) natural antisense, set forth as SEQ ID NO: 5 to 14 and modulate expression and/or function of a Sirtuin (SIRT) molecule.

In a embodiment, oligonucleotides comprise sequences of at least 5 consecutive nucleotides of SEQ ID NOS: 15 to 94 and modulate expression and/or junction of a Sirtuin (SIRT) molecule.

The polynucleotide targets comprise Sirtuin (SIRT), including family members thereof, variants of a Sirtuin (SIRT); mutants of a Sirtuin (SIRT) including SNPs; non-coding sequences of a Sirtuin (SIRT); alleles of a Sirtuin (SIRT); species variants, fragments and the like. Preferably the oligonucleotide is an antisense molecule.

In another embodiment, the oligonucleotide targeting Sirtuin (SIRT) polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another embodiment, targeting of a Sirtuin (SIRT) polynucleotide, e.g. SEQ ID NO: 5 to 14 modulate the expression or function of these targets. In one embodiment, expression or function is up-regulated as compared to a control. In another embodiment, expression or function is down-regulated as compared to a control.

In another embodiment, antisense compounds comprise sequences set forth as SEQ ID NOS: 15 to 94. These oligonucleotides can comprise one or more modified nucleotides, shorter or longer fragments, modified bonds and the like.

In another embodiment, SEQ ID NOS: 15 to 94 comprise one or more LNA nucleotides.

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalysing one or more of a variety of reactions, including the ability to repeatedly cleave other separate nucleic acid molecules its a nucleotide base sequence-specific manner. Such enzymatic nucleic acid molecules can be used, for example, to target virtually any RNA transcript.

Because of their sequence-specificity, trans-cleaving nucleic acid molecules show promise as therapeutic agents for human disease. Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognises and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies have been used to evolve new nucleic acid catalysts capable of catalysing a variety of reactions, such as cleavage and ligation of phosphodiestor linkages and amide linkages.

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min−1 in the presence of saturating (10 mM) concentrations of Mg2+ cofactor. An artificial "RNA ligase" ribozyme has been shown to catalyze the corresponding self-modification reaction with a rate of about 100 min−1. In addition, it is known that certain modified hammerhead ribozymes that have substrate binding arms made of DNA catalyse RNA cleavage with multiple turn-over rates that approach 100 min−1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987. The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalyse RNA to maintain necessary base pairing with the target sequences. This has allowed use of the catalytic RNA to cleave specific target sequences and indicates that catalytic RNAs designed according to the "hammerhead" model may possibly cleave specific substrate RNAs in vivo.

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In one embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" includes antisense oligonucleotides (e.g. RNA, DNA, mimetic, chimera, analog or homolog thereof), ribozymes, external guide sequence (EGS) oligonucleotides, siRNA compounds, single- or double-sided RNA interference (RNAi) compounds such as siRNA compounds, saRNA, aRNA, and other oligomeric compounds which hybridize to at least a portion of the target nucleic acid and modulate its reaction. As such, they may be DNA, RNA, DNA-like, RNA-like, or mixtures thereof, or may be mimetics of one or more of these. These compounds may be single-stranded, double-stranded circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiment, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound, in other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides at length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another embodiment, the oligomeric compounds of the present invention also include variants in which a different base is present at one or more of the nucleotide positions in the compound. For example, if the first nucleotide is an adenosine, variants may be produced which attain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another embodiment, the antisense oligonucleotides, such as for example, nucleic acid molecules set forth in SEQ ID NOS: 4 to 29 comprise one or more substitutions or modifications. In one embodiment, the nucleotides are substituted with locked nucleic acids (LNA).

In another embodiment, the oligonucleotides target one or more regions of the nucleic acid molecules sense and/or antisense of coding and/or non-coding sequences associated with Sirtuin (SIRT) and the sequences set forth its SEQ ID NOS: 1 to 14. Use oligonucleotides are also targeted to overlapping regions of SEQ ID NOS: 1 to 14.

Certain oligonucleotides of this invention are chimeric oligonucleotides, "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one embodiment, a chimeric oligonucleotide comprises at least one region modified to increase target binding affinity, and usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775, 5,366,878; 5,403,711; 5,491,133; 5,565,350; 5,623,065; 5,652,355; 5,652,356; and 5,700,922, each of which is herein incorporated by reference.

In another embodiment, the region of the oligonucleotide which is modified comprises at least one nucleotide modified at the 2' position of the sugar, most preferably a 2'-O-alkyl, 2'-O-alkyl-O-alkyl or 2'-fluoro-modified modified nucleotide. In other embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another embodiment the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. (1995) *Acc. Chem. Res.*, 28:366-374.

Specific examples of some oligonucleotides envisioned for this invention include those comprising modified backbones, for example, phosphosothioates, phosphotriesters, methyl phosphonates, short chain alkyl or cycloalkyl intersugar linkages or short chain heteroatomic or heterocyclic intersugar linkages. Most are oligonucleotides with phosphorothioate backbones and those with heteroatom backbones, particularly $CH_2$-NH—O—$CH_2$, CH, —N($CH_3$)—O—$CH_2$ [known as a methylene(methylimino) or MMI backbone], $CH_2$-O—N($CH_3$)—$CH_2$, $CH_2$-N($CH_3$)—N($CH_3$)—$CH_2$ and O—N($CH_3$)—$CH_2$-$CH_2$ backbones, wherein the native phosphodiester backbone is represented as O—P—O—CH.). The amide backbones disclosed by De Mesmacker et al. (1995) *Acc. Chem. Res.* 28:366-374 are also preferred. Also are oligonucleotides having morpholino backbone structures (Summerton and Weller, U.S. Pat. No. 5,034,506). In other embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties, oligonucleotides compose one of the following at the 2' position: OH, SH, $SCH_3$, F, OCN, $OCH_3$ $OCH_3$, $OCH_3O(CH_2)n$ $CH_3$, $O(CH_2)n$ $NH_2$ or $O(CH_2)n$ $CH_3$ where n is from 1 to about 10; C1 to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A modification includes 2'-methoxyethoxy [2'-O—$CH_2$ CH2 OCH3, also known as 2'-O-(2-methoxyethyl)]. Other modifications include 2'-methoxy (2'-O—C3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Mc pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, a thioether, e.g., hexyl-S-trithylthiol, a thiocholesterol, an aliphatic chain, e.g., dodecandiol or undecyl residues, a phospholipid, e.g., di-hexandecyl-rac-glycerol or triethylammonium 1,2-di-O-hexadecyl-rac-glycero-3-H-phosphonate, a polyamine or a polyethylene glycol chain, or adamantane acetic acid. Oligonucleotides comprising lipophilic moieties, and methods for preparing such oligonucleotides are known in the art, for example, U.S. Pat. Nos. 5,138,045, 5,218,105 and 5,459, 255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyester, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to these similar techniques to prepare other oligonucleotides such as the phosphorothioates and alkylated derivatives. It is also well known to use similar techniques and commercially available modified amidities and controlled-pore glass (CPG) products such as biotin, fluorescein, acridine or psoralen-modified amidities and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc. This can be achieved by substituting some of the monomers in the current oligonucleotides by LNA monomers. The LNA modified oligonucleotide may have a size similar to the parent compound or may be larger or preferably smaller. It is that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Modified oligonucleotide backbones comprise, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionalkylphosphonates, thionalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,809; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are limited to, U.S. Pat. Nos. 5,034,506; 5,166,315; 5,185,444; 5,214,134; 5,216,141; 5,235,033; 5,264,562, 5,264,564;

5,405,938; 5,434,257; 5,466,677; 5,470,967; 5,489,677; 5,541,307; 5,561,225, 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331, and 5,719, 262, each of which is herein incorporated by reference. Further teaching of PNA compounds can be found in Nielsen, et al (1991) Science 254, 1497-1500.

In another embodiment of the invention the oligonucleotides with phosphorothioate backbones and oligonucleosides with heteroatom backbones, and in particular —CH2-NH—O—CH2-, —CH2-N(CH3)—O—CH2-known as a methylene (methylimino) or MMI backbone, —CH2-O—N(CH3)—C2-, —CH2N(CH3-N(CH3)CH2- and —O—N(CH3)—CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also are oligonucleotides having morpholino backbone structures of the above-referenced U.S. Pat. No. 5,034,506.

Modified oligonucleotides may also contain one or more substituted sugar moieties, oligonucleotides comprise one of the following at the 2' position; OH; F; O-, S-, or N-alkyl; O-, S-, or N-alkenyl; O-, S- or N-alkynyl; or O alkyl-O-alkyl wherein the alkyl, alkenyl and alkynyl may be substituted or unsubstituted C to CO alkyl or C2 to CO alkenyl and alkynyl. Particularly are O (CH2)n OmCH3, O(CH2)n, OCH3, O(CH2)nNH2, O(CH2)nCH3, O(CH2)nONH2, and O(CH2nON(CH2)nCH3)2 where n and m can be from 1 to about 10. Other oligonucleotides comprise one of the following at the 2' position; C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkyaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A modification comprises 2'-methoxyethoxy (2'-O—CH2CH2OCH3, also known as 2'-O-(2-methoxyethyl) or 2'-MOE) i.e., an alkoxyalkoxy group. A further modification comprises 2'-dimethylaminooxyethoxy, i.e., a O(CH2)2ON(CH3)2 group, also known as 2'-DMAOE, as described in examples herein, below, and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other modifications comprise 2'-methoxy (2'-OCH3), 2'-aminopropoxy (2'-OCH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structure comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,656,265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S. Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and O-6 substituted purines, comprising 2-aminopropyladenine, 5-propynyluracil and 5-propynylcytosine, 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently base substitutions, even more particularly when combined with 2'-Omethoxyethyl sugar modifications.

Representative United States patents that teach the preparation of the above noted modified nucleotides as well as other modified nucleotides comprise but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-t oxycholesterol moiety.

Representative United States patents that teach the preparation of such oligonucleotides conjugates comprise, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,028,830; 5,112,063; 5,214,130; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,367,810; 5,574,142; 5,585,481; 5,587,371; 5,595,726; 5,507,696; 5,590,923; 5,599,928 and 5,688,941, each of which is herein incorporated by reference.

Drug discover: The compounds of the present invention can also be applied in the areas of drug discovery and target validation. The present invention comprehends the use of the compounds and target segments identified herein in drug discovery efforts to elucidate relationships that exist between a Sirtuin (SIRT) polynucleotide and a disease state, phenotype, or condition. These methods include detecting or modulating a Sirtuin (SIRT) polynucleotide comprising contacting a sample, tissue, cell, or organism with the compounds of the present invention, measuring the nucleic acid or protein level of a Sirtuin (SIRT) polynucleotide and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-regulation or Inhibition of Gene Expression

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysts. For instance, mRNA produced from an exogenous nucleic acid can be detected and quantified using a Northern blot and reverse transition PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, printers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), *luciferase* (Luc), nopaline synthase (NOS), octopine synthase (OCS), and derivatives thereof. Multiple selectable markets are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy. Fluorescence Activated Cell Sorting (FACS), fluorescence microscopy), antibiotic resistance determination.

SIRT1, SIRT3 and SIRT6 proteins and mRNA expression can be assayed using methods known to those of skill in the art and described elsewhere herein. For example, immunoassays such as the ELISA can be used to measure protein levels. Sirtuin (SIRT) antibodies for ELISAs are available commercially, e.g., from R&D Systems (Minneapolis, Minn.), Abcam, Cambridge, Mass.).

In embodiments, SIRT1, SIRT3 and SIRT6 expression (e.g., mRNA or protein) in a sample (e.g., cells or tissues in vivo or in vitro) treated using an antisense oligonucleotide of the invention is evaluated by comparison with Sirtuin (SIRT) expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the Sirtuin (SIRT) protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of a Sirtuin (SIRT) mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of a Sirtuin (SIRT) mRNA or protein is increased or decreased by at least about 1.25-fold, at least about 1.3-fold, at least about 1.4-fold, at least, about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilised for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Sirtuin (SIRT). These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analysed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) *FEBS Lett.*, 480, 17-24; Celis, et al., (2000) *FEBS Lett.*, 480, 2-16), SAGE (serial analysis of gene expression) (Madden, et al., (2000) Drug Discov. Today, 5, 415-425), READS, (restriction enzyme amplification of digested cDNAs) (Prashar and Weissman, (1999) *Methods Enzymol.*, 303, 258-72), TOGA (total gene expression analysis) (Sutcliffe, et al., (2000) *Proc. Natl. Acad. Sci, U.S.A.*, 97, 1976-81), protein arrays and proteomics (Celis, et al., (2000) *FEBS Letter.*, 480, 2-16; Jungblut, et al., Electrophoresis, 1999, 20, 2100-10), expressed sequence tag (EST) sequencing (Celis, et al., FEBS Letter., 2000, 480, 2-16; Larsson, et al., J. Biotechnol., 2000, 80, 143-57), subtractive RNA fingerprinting (SuRF) (Fuchs, et al., (2000) Anal. Biochem. 286, 91-98; Larson, et al., (2000) *Cytometry* 51, 203-208), subtractive cloning, differential display (DD) (Jurecic and Belmont, (2000) *Curr. Opin. Microbiol.* 3, 316-21), comparative genomic hybridization (Carulli, et al., (1998) *J. Cell Biochem. Suppl.*, 31, 286-96), FISH (fluorescent in situ hybridization) techniques (Going and Gusterson, (1999) *Eur. J. Cancer*, 3, 1895-94) and mass spectrometry methods (To, Comb. (200) *Chem. High Throughput Screen*, 3, 235-41).

The compounds of the invention are useful for research and diagnostics, because these compounds hybridize to nucleic acids encoding a Sirtuin (SIRT). For example, oligonucleotides that hybridise with such efficiency and under such conditions as disclosed herein as to be effective Sirtuin (SIRT) modulators are effective primers or probes under conditions flavoring gene amplification or detection, respectively. These primers and probes are useful in methods requiring the specific detection of nucleic acid molecules encoding a Sirtuin (SIRT) and in the amplification of said nucleic acid molecules for detection or for use in further studies of a Sirtuin (SIRT). Hybridization of the antisense oligonucleotides, particularly the primers and probes, of the invention with a nucleic acid encoding a Sirtuin (SIRT) can be detected by means known in the art. Such means may include conjugation of an enzyme to the oligonucleotide, radiolabeling of the oligonucleotide, or any other suitable detection means. Kits using such detection means for detecting the level of a Sirtuin (SIRT) in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of a Sirtuin (SIRT) polynucleotide is treated by administering antisense compounds in accordance with this invention. For example, in one non-limiting embodiment, the methods comprise the step of administering to the animal in need of treatment, a therapeutically effective amount of a Sirtuin (SIRT) modulator. The Sirtuin (SIRT) modulators of the present invention effectively modulate the activity of a Sirtuin (SIRT) or modulate the expression of a Sirtuin (SIRT) protein. In one embodiment, the activity or expression of a Sirtuin (SIRT) in an animal is inhibited by about 10% as compared to a control. Preferably, the activity or expression of a Sirtuin (SIRT) in an animal is inhibited by about 30%. More preferably the activity or expression or a Sirtuin (SIRT) in an animal is inhibited by 50% or more. Thus, the oligomeric compounds modulate expression of a Sirtuin (SIRT) mRNA by at least 10%, by at least 50%, by at least 25%, by at least 30%, by at least 40%, by at least 50%, by as least 60%, by at least 70%, by at least 75%, by at least 80%, by at least 85%, by at least 90%, by at least 95%, by at least 90%, by at least 99%, or by 100% as compared to a control.

In one embodiment, the activity or expression of a Sirtuin (SIRT) and/or in an animal is increased by about 10% as compared to a control. Preferably, the activity or expression of a Sirtuin (SIRT) in an animal is increased by about 30%. More preferably, the activity or expression of a Sirtuin (SIRT) in an animal is increased by 50% or more. Thus, the oligomeric compounds modulate expression of a Sirtuin (SIRT) mRNA by at least 10%, by at least 50%, by at least 25%, by at least 30%, by at least 40%, by at least 50%, by at least 60%, by at least 70%, by at least 25%, by at least 80%, by at least 85% by at least 90%, by at least 95%, by at least $8%, by at least 99%, or by 100% as compared to a control.

For example, the reduction of the expression of a Sirtuin (SIRT) may be measured in serum, blood, adipose tissue, liver or any other body fluid, tissue or organ of the animal. Preferably, the cells contained within said fluids, tissues or organs being analysed contain a nucleic acid molecule encoding Sirtuin (SIRT) peptides and/or the Sirtuin (SIRT) protein itself.

The compounds of the invention can be utilised in pharmaceutical compositions by adding an effective amount of a compound to a suitable pharmaceutically acceptable diluent or carrier. Use of the compounds and methods of the invention may also be useful prophylactically.

Conjugates: Another modification of the oligonucleotides of the invention involve chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations: The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528, 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function embodiments of the invention relates to expression vector constructs for the expression of antisense oligonucleotides, comprising promoters, hybrid promoter gene sequences and possess a strong constitutive promoter activity, or a promotes activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 15 to 94) or in combination with a suitable protein, polysaccharide or lipid formulation.

Additionally suitable nucleic acid delivery systems include vital vector, typically sequence from at least one of an adenovirus, adenovirus-associated virus (AAV), helper-dependent adenovirus, retrovirus, or hemagglutination virus of Japan-liposome (HVJ) complex. Preferably, the vital vector comprises a strong eukaryotic promoter operably linked to the polynucleotide e.g., a cytomegalovirus (CMV) promoter.

Additionally vectors include viral vectors, fusion proteins and chemical conjugates. Retroviral vectors include Moloney murine leukemia viruses and HIV-based viruses. One HIV-based vital vector comprises at least two vectors wherein the gag and pol genes are from an HIV genome and the env gene is from another virus. DNA vital vectors are preferred. These vectors include pox vectors such as orthopox or avipox vectors, herpesvirus vectors such as a herpes simplex I virus (HSV) vector, Adenovirus Vectors and Adeno-associated Virus Vectors).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal, and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in it entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g. infusion of sugars including, but not limited to, meso erythritol, xylitol, D(+) galactose, D(+) lactose, D(+) xylose, dulcitol, myoinositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parental delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextrin. The suspension may also contain stabilisers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 µm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287, 860.

Formulations of the present invention include liposomal modulations. As used in the present invention, the term "liposome" means a vesicle composed of amphiphilic lipids arrange in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognise that formulations are routinely designed according to their intended use, i.e. route of administration.

formulations for topical administration include those in which the oligonucleotides of the invention are in admixture with a topical delivery agent such as lipids, liposomes, fatty acids, fatty acid esters, steroids, chelating agents and surfactants, lipids and liposomes include neutral (e.g. dioleoylphosphatidyl DOPE ethanolamine, dimyristoylphosphatyl choline DMPC, distearolyphosphatidyl choline) negative (e.g. dimyristoylphosphatidyl glycerol DMPG) and cationic (e.g. diolcoyltetramethylaminopropyl DOTAP and dioleoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be completed to lipids, in particular to cationic lipids, fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable, oral formulations are those in which oligonucleotides of the invention, are administered in conjunction with one or more penetration enhancers surfactants and chelators, surfactants include fatty acids and/or esters or salts thereof, bile acids and/or salts thereof. bile acids/salts and fatty acids and their uses are further described in U.S. Pat. No. 6,287,860, which is incorporated herein by reference. Also are combinations of penetration enhancers, for example, fatty acids/salts in combination with bile acids/salts. A particularly contention is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticle. Oligonucleotide complexity agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomysin, mafosfamide, ifosfamide, cytosine arabinoside, bischloroethyl-nitrosurea, busulfan, mitomysin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxy-cyclo-phosphoramide, 5-fluorouracil (5-FU) 5-fluorodeoxyuridine (5-FUdR), methotrexate (MTX), colchicine, taxol, vincristine, vinblastine, etoposide (VP-16), trimetrexate, irinotecan, topotecan, germcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of a Sirtuin (SIRT), and the second target may be a region from another nucleotide sequence. Alternatively, compositions of the invention may contain two or more antisense compounds targeted to different regions of the same Sirtuin (SIRT) nucleic acid target. Numerous examples of antisense compounds are illustrated herein and others may be selected from among suitable compounds known to the art. Two or more combined compounds may be used together or sequentially.

Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least shout 35, at least about 40, at least about 45, at least about 50, at least about 60, at least about 70, at least about 50, at least about 90, or at least about 100 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Design of Antisense Oligonucleotides Specific for a Nucleic Acid Molecule Antisense to a Sirtuin (SIRT) and/or a Sense Strand of a Sirtuin (SIRT) Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display as appropriate degree of identity between species. In the case of genes that have not been sequenced, Southern blots are performed to allow a determination of the degree of identity between genes in target species and other species. By performing Southern blots at varying degrees, of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc., MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes; then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or LightTyper instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2: Modulation of SIRT Polynucleotides

Treatment of HepG2 Cells with Antisense Oligonucleotides

HepG2 cells from ATCC (cat #HB-8065) were grown in growth media (MEM/EBSS (Hyclone cat #SH30024, or Mediatech cat #MT-10-010-CV) +10% FBS (Mediatech cat #MT35-011-CV)+ penicillin/streptomycin (Mediatech cat #MT30-002-CI)) at 37° C. and 5% $CO_2$. One day before the experiment the cells were replaced at the density of 1.5× $10^5$/ml into 6 well plates and incubated at 37° C. and 5% $CO_3$. On the day of the experiment the media in the 6 well plates was changed to fresh growth media. All antisense oligonucleotides were diluted to the concentration of 20 μM. Two μl of this solution was incubated with 400 μl of Opti-MEM media. (Gibco cat #31985-070) and 4 μl of Lipofectamine 2000 (Invitrogen cat #11668019) at room temperature for 20 min and applied to each well of the 6 well plates with HepG2 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit Qiagen (cat #74181) following the manufacturers' instructions. 600 ng of RNA was added to the reverse transcription reaction performed using Verso c-DNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_m1, Hs00202030_m1 and Hs002130306_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Results

Figure 3:
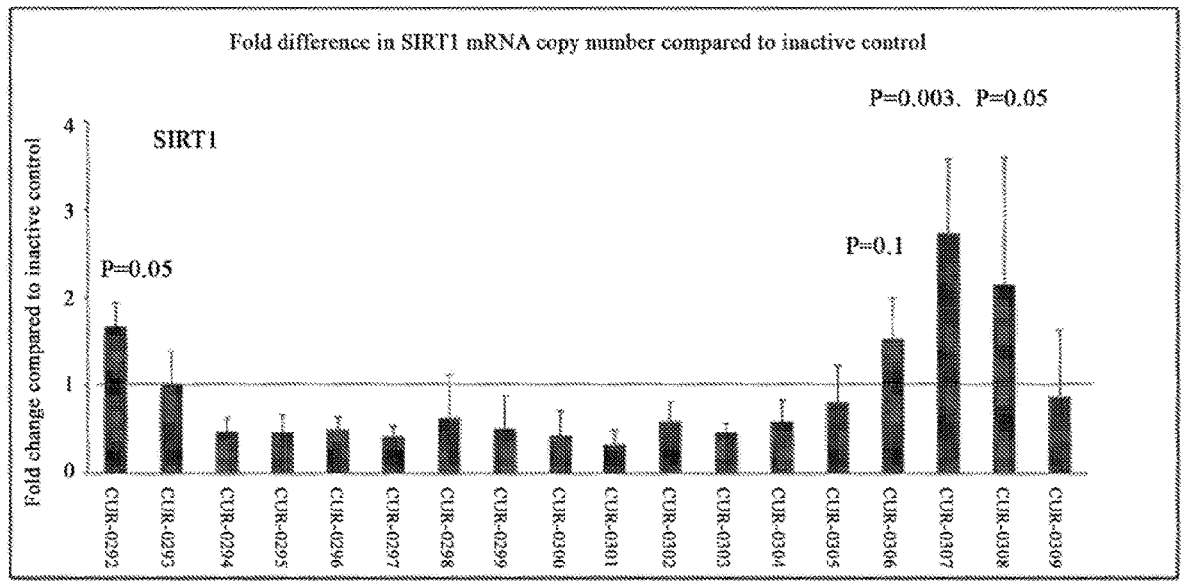
FIG. 3 shows results for the oligonucleotide walk across the SIRT antisense. Real time PCT results show that the levels of the SIRT1 mRNA HepG2 cells are significantly increased 48 h after treatment with three of the antisense oligonucleotides designed to sirtas. CUR-0292 to CUR-0309 correspond to SEQ ID NOs: 15 to 32 respectively.
Figure 4:
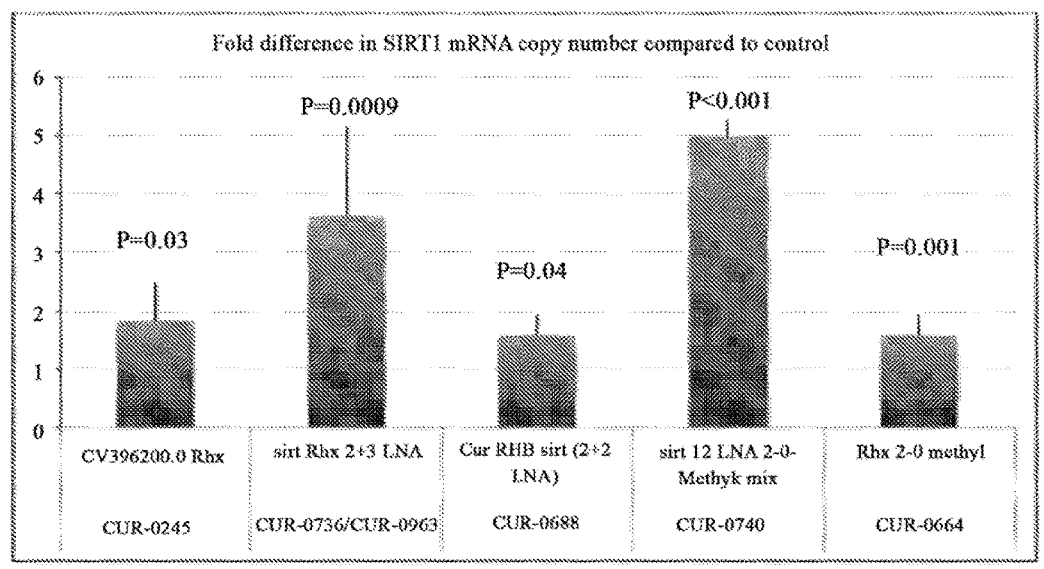
FIGS. 4 and 5 show results for PS, LNA and 2'O Me Modified oligonucleotides in HepG2 (FIG. 4) and Vero76 (FIG. 5) cells. Real time PCR results show that the levels of the SIRT1 mRNA in HepG2 cells are significantly increased 48 h after treatment with PS, LNA, 2'O Me and 2'O Me mixmer designed antisense oligonucleotides to SIRT1 antisense. Levels of SIRT1 mRNA in Vero cells also increased 48 hours after treatment with PS and LNA modified antisense oligonucleotides to SIRT1 antisense. Bars denoted as CUR-0245, CUR-0736, CUR 0688, CUR-0740 and CUR-0664 correspond to SEQ ID NOs: 33 to 37 respectively.

Real time PCR results show that the levels of the SIRT1 mRNA in HepG2 cells significantly increased 48 h after treatment with some antisense oligonucleotides to SIRT1 antisense CV396200 (FIG. 3, 4).

Figure 8:
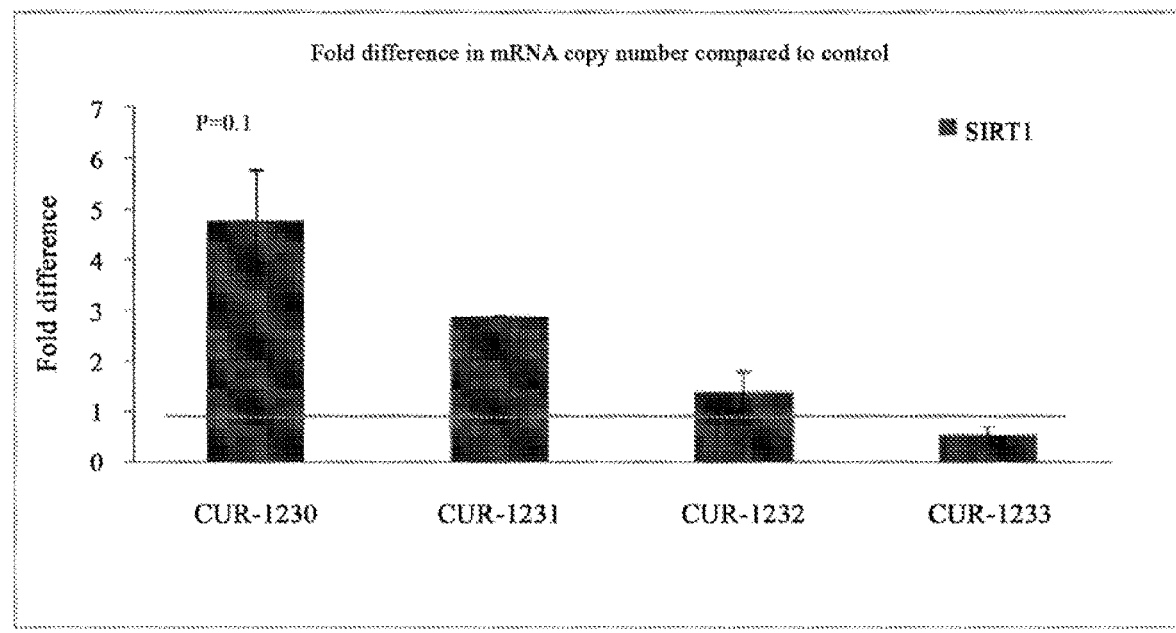
FIG. 8 shows results for oligonucleotides designed to SIRT antisense CV396200. Real Time PCR results shown that levels of SIRT1 mRNA in HepG2 cells are significantly increased in one of the oligonucleotides designed to SIRT1 antisense CV396200. The bars denoted as CUR-1230, CUR-1231, CUR-1232 and CUR-1233 correspond to SEQ ID NOs: 41 to 44.

Real Time PCR results show that levels of SIRT1 mRNA in HepG2 cells are significantly increased in one of the oligonucleotides designed to SIRT1 antisense CV396200 (FIG. 8).

Figure 9:
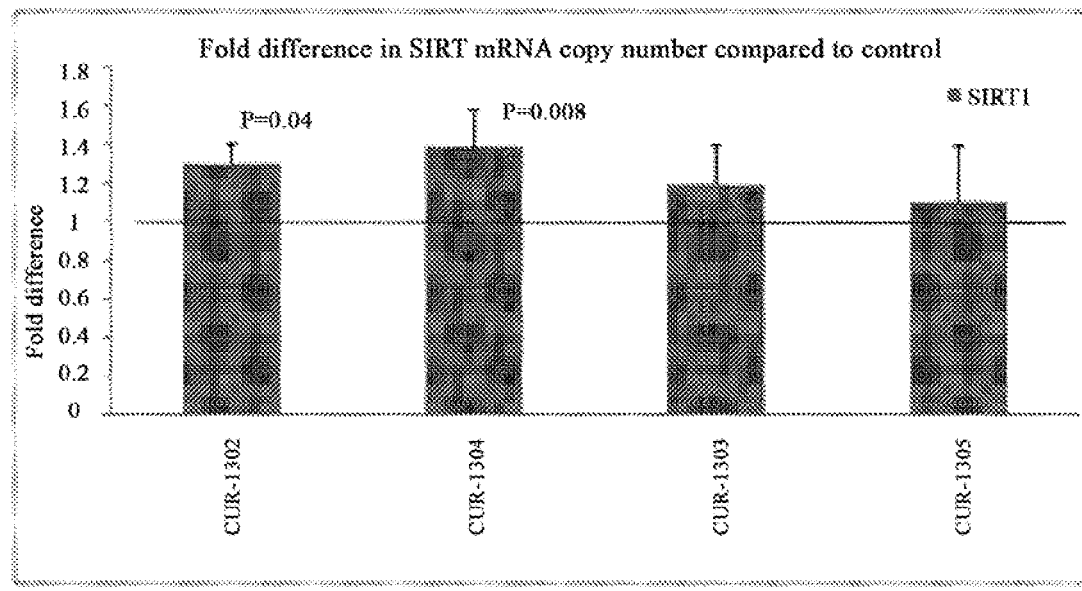
FIG. 9 shows results for oligonucleotides designed to SIRT antisense CV428275. Real Time PCR results show that levels of SIRT1 mRNA in HepG2 cells are significantly increased in two of the oligonucleotides designed to SIRT1 antisense CV428275. The bars denoted as CUR-1302, CUR-1304, CUR-1303 and CUR-1305 correspond to SEQ ID NOs: 45 to 48.

Real Time PCR results show that levels of SIRT1 mRNA in HepG2 cells are significantly increased in two of the oligonucleotides designed to SIRT1 antisense CV428275 (FIG. 9).

Figure 10:
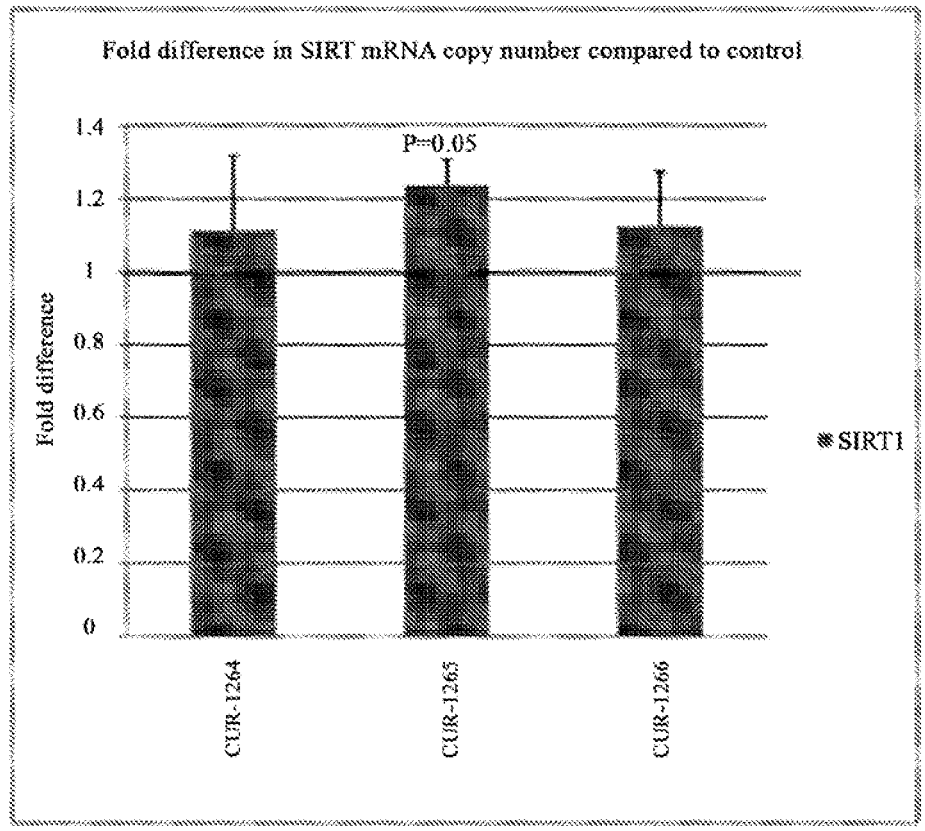
FIG. 10 shows Real time PCR results. The results show that a significant increase in SIRT1 mRNA levels in HepG2 cells 48 hours after treatment with one of the oligonucleotides designed to SIRT antisense BE717453. The bars denoted as CUR-1264, CUR1265 and CUR-1266 correspond to SEQ ID NOs: 49 to 51 respectively.

The results show that a significant increase in SIRT1 mRNA levels in HepG2 cells 48 hours after treatment with one of the oligonucleotides designed to SIRT antisense BE717453. (FIG. 10).

Figure 11:
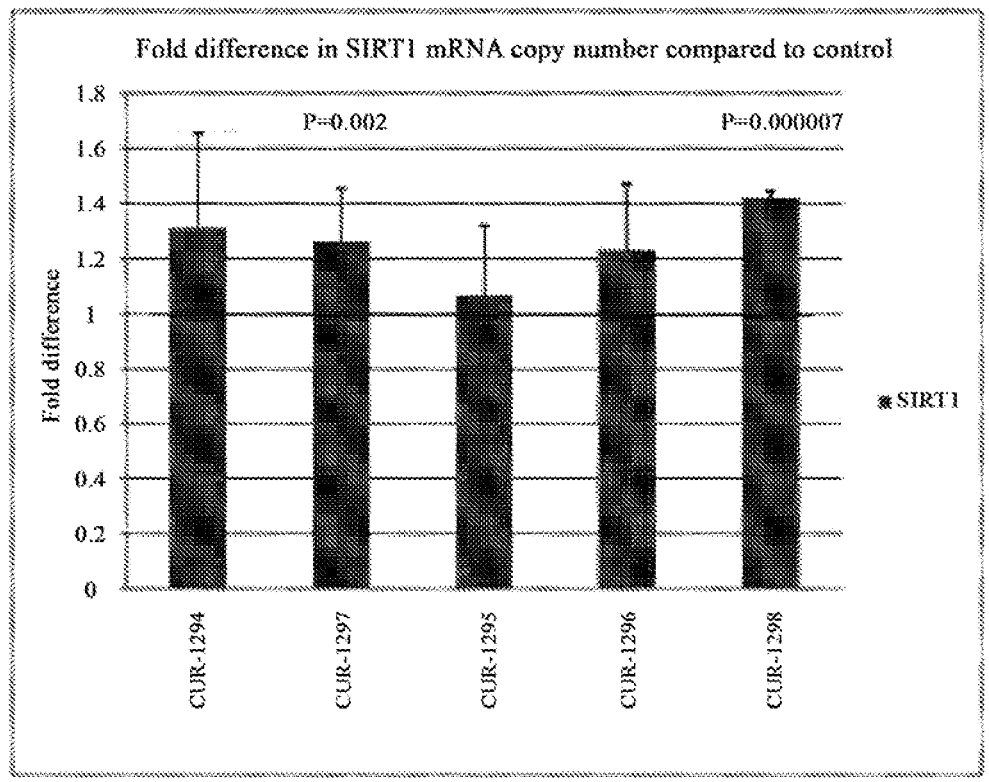
FIG. 11 shows Real time PCR results. The results show that show that the levels of the SIRT1 mRNA in HepG2 cells are significantly increased 48 h after treatment with three of the oligonucleotides designed to SIRT1 antisense. AV718812. The bars denoted as CUR-1294, CUR-1297, CUR-1295, CUR-1296 and CUR-1298 correspond to SEQ ID NOs; 52 to 56 respectively.

The results show that show that the levels of the SIRT1 mRNA to HepG2 cells are significantly increased 48 h after treatment with three of the oligonucleotides designed to SIRT1 antisense AV718812 respectively (FIG. 11).

Figure 12:
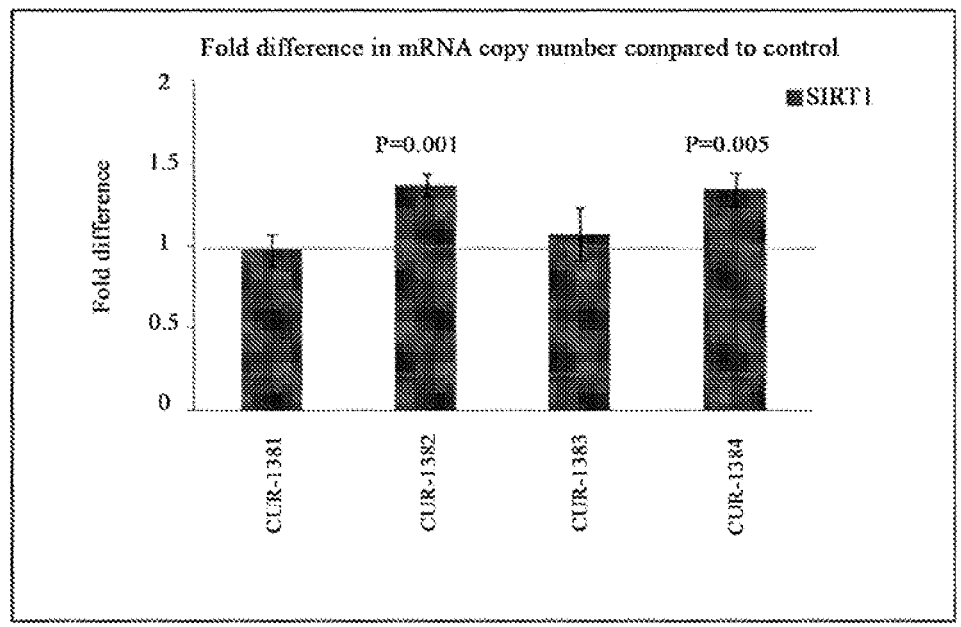
FIG. 12 is a graph of real time PCR results showing the fold change+standard deviation in SIRT1 mRNA after treatment of HepG2 cells with phosphorothioate oligonucleotides introduced using Lipofectamine 2000, as compared to control. Real time PCR results show that the levels of SIRT1 mRNA are significantly increased in HepG2 cells 48 h after treatment with two of the oligos designed to SIRT1 antisense AW169958. Bars denoted as CUR-1381, CUR-1382, CUR-1383 and CUR-1384 correspond to samples treated with SEQ ID NOS: 57 to 60 respectively.

Real time PCR results show that the levels of SIRT1 mRNA in HepG2 cells are significantly increased 48 h after treatment with two of the oligos designed to SIRT1 antisense AW169958 (FIG. 12).

Figure 17:
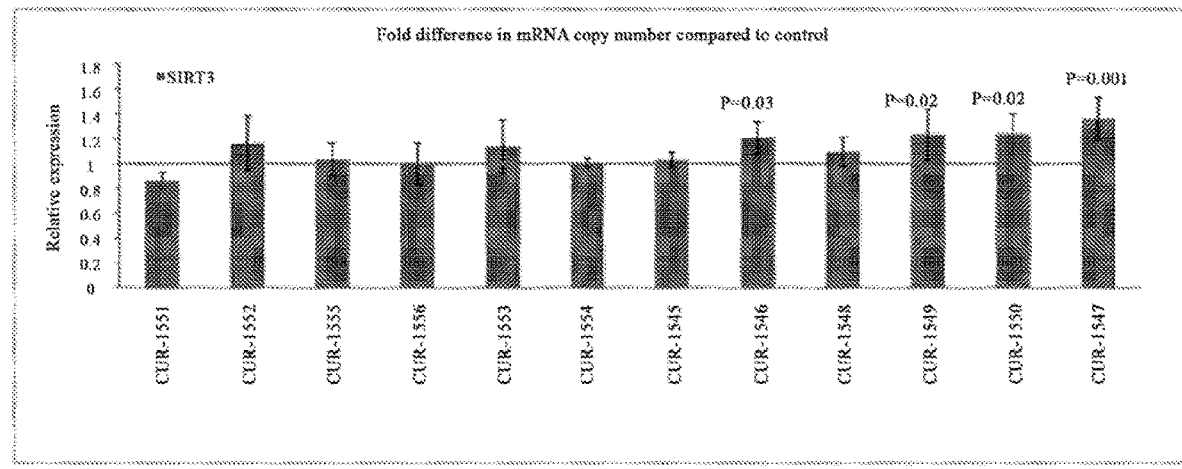
FIG. 17 is a graph of real time PCR results showing the fold change+standard deviation in Sirtuin3 mRNA after treatment of HepG2 cells with phosphorothioate oligonucleotides introduced using Lipofectamine 2000, as compared to control. RT PCR results show that sirt3 levels in HepG2 cells are increased 48 hours after treatment with phosphorothioate antisense oligonucleotides designed to sirt3 antisense Hs683117 (CUR-1545-1550). Bars denoted as CUR-0551, CUR-1552, CUR-1555, CUR-1556, CUR-1553, CUR-1554, CUR-1545, CUR-1546, CUR-1548, CUR-1549, CUR-1550 and CUR-1547, correspond to samples treated with SEQ ID NOS: 73 to 84 respectively.

RT PCR results show that sirt3 levels is HepG2 cells are increased 48 hours after treatment with phosphorothioate antisense oligonucleotides designed to sirt3 antisense Hs.683117 (CUR-1545-1550) (FIG. 17).

Figure 18:
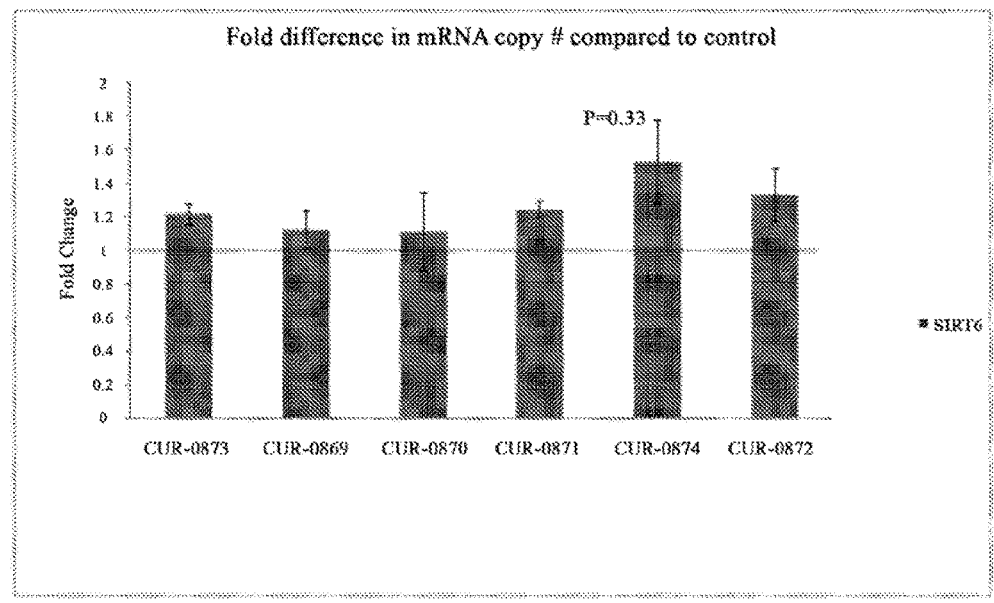
FIG. 18 is a graph of real time PCR results showing the fold change+standard deviation in SIRT6 mRNA after treatment of HepG2 cells with phosphorothioate oligonucleotides introduced using Lipofectamine 2000, as compared to control. Real time PCR results show that the levels of SIRT6 mRNA in HepG2 cells are significantly increased 48 h after treatment with one of the oliogs designed to SIRT6 antisense NM_133475. Bars denoted as CUR-0873, CUR-0869 to CUR-0871, CUR-0874 and CUR-0972, correspond to samples treated with SEQ ID NOS: 85 to 90 respectively.

Real time PCR results show that the levels of SIRT6 mRNA in HepG2 cells are significantly increased 48 h after treatment with one of the oliogs designed to SIRT6 antisense NM_133475 (FIG. 18).

Figure 19:
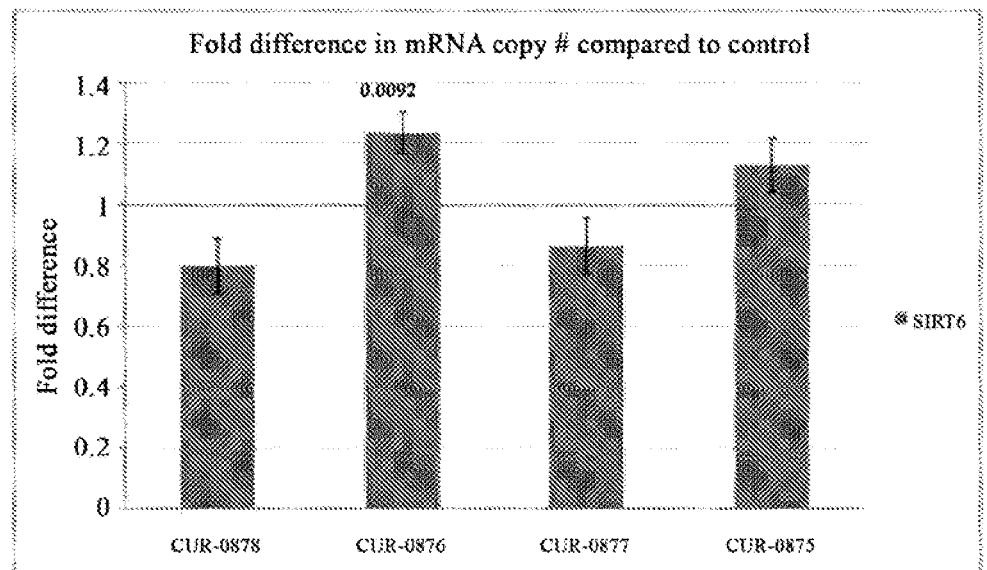
FIG. 19 is a graph of real time PCR results showing the fold change+standard deviation in SIRT6 mRNA after treatment of HepG2 cells with phosphorothioate oligonucleotides introduced using Lipofectamine 2000, as compared to control. Real time PCR results show that the levels of SIRT6 mRNA in HepG2 cells are significantly increased 48 h after treatment with one of the olioigs designed to SIRT6 antisense bf772662. Bars denoted as CUR-0878, CUR-0876 to CUR-0877, CUR-0875, correspond to samples treated with SEQ ID NOS: 91 to 94 respectively.

Real time PCR results show that the levels of SIRT6 mRNA in HepG2 cells are significantly increased 48 h after treatment with one of the oliogs designed to SIRT6 antisense bf772662 (FIG. 19)

Treatment of 3T3 Cells with Antisense Oligonucleotides

3T3 cells from ATCC (cat #CRL-1658) were grown in growth media (MEM/EBSS (Hyclone cat #SH30024, or Mediatech cat #MT-10-010-CV) +10% FBS (Mediatech cat #MT35-011-CV)+ penicillin/streptomycin (Mediatech cat #MT30-010-CI)) at 37° C. and 5% $CO_3$. One day before the experiment the cells were replated at the density of 1.5× $10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31984-070) and 4 μl of Lipofectamine 2000 (Invitrogen cat #11668019) at room temperature for 20 min and applied to each well of the 6 well plates with 3T3 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturer's instructions, 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_ml by Applied Biosystems Inc. Foster City Calif.). The following PCR cycle was used: 50° C. for 2 min, 95° C. for 10 in, 40 cycles of (95° C. for 15 seconds, 60° C. for 1 min) using StepOne Plus Real Time PCR Machine (Applied Biosystems).

Fold change to gene expression after treatment with antisense oligonucleotides was calculated based on the difference in 18S-normalized dCt values between treated and mock-transfected samples.

Results

Figure 13:
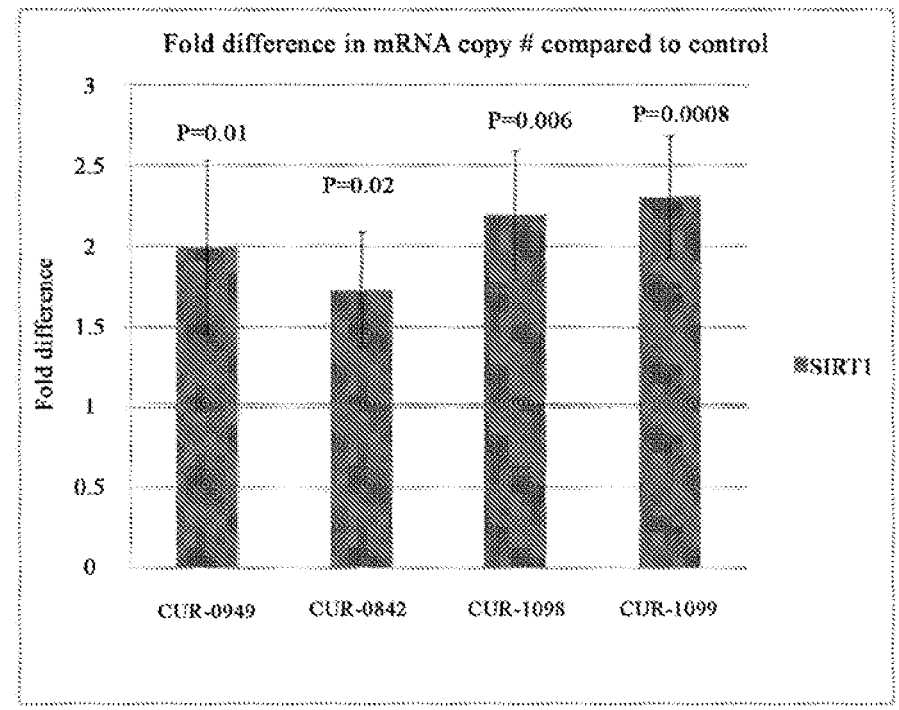
FIG. 13 is a graph of real time PCR results showing the fold change+standard deviation in SIRT1 mRNA after treatment of 3T3 cells with phosphorothioate oligonucleotides introduced using Lipofectamine 2000, as compared to control. Real time PCR results show that the levels of SIRT1 mRNA are significantly increased in 3T3 cells 48 h after treatment with three of the oligonucleotides designed to SIRT1 mouse antisense AK044604. Bars denoted as CUR-0949, CUR-0842, CUR-1098 and CUR-1099 correspond to samples treatment with SEQ ID NOS: 67, 61, 71 and 72 respectively.

Real time PCR results show that the levels of SIRT1 mRNA are significantly increased in 3T3 cells 48 h after treatment with three of the oligonucleotides designed to SIRT1 mouse antisense AK044604 (FIG. 13).

Figure 14:
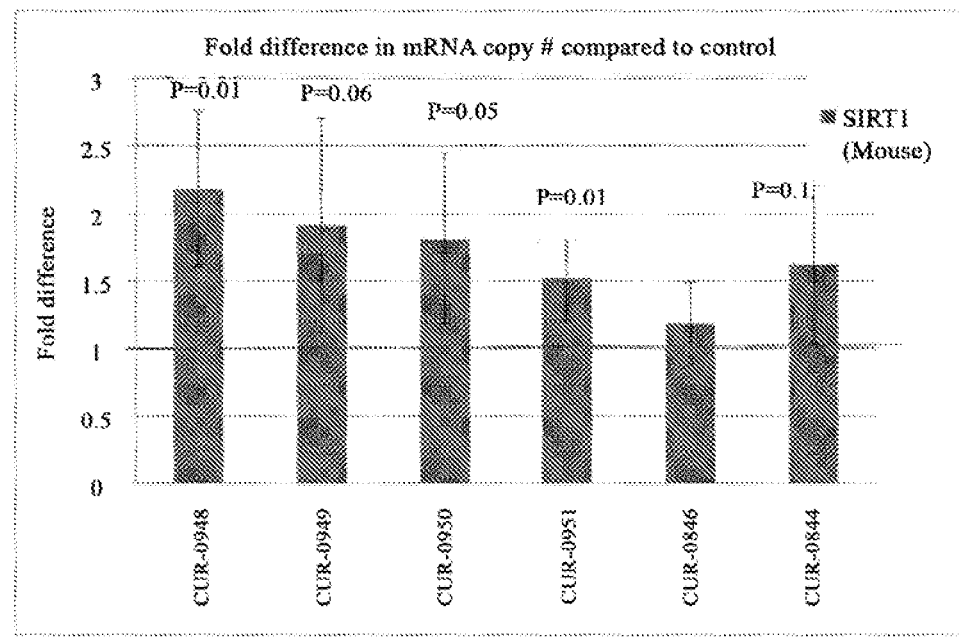
FIG. 14 is a graph of real time PCR results showing the fold change+standard deviation in SIRT1 mRNA after treatment of 3T3 cells with phosphorothioate oligonucleotides introduced using Lipofectamine 2000, as compared to control. Real time PCR results show that the levels of SIRT1 mRNA are significantly increased in 3T3 cells 48 h after treatment with five of the oligonucleotides designed to SIRT1 mouse antisense AK044604. Bars denoted as CUR-0948, CUR-0949, CUR-0950, CUR-0951, CUR-0846, and CUR-0844 correspond to samples treatment with SEQ ID NOS: 66 to 69, 65 and 63 respectively.

Real time PCR results show that the levels of SIRT1 mRNA are significantly increased in 3T3 cells 48 h after treatment with five of the oligonucleotides designed to SIRT1 mouse antisense AK044604 (FIG. 14).

Figure 15:
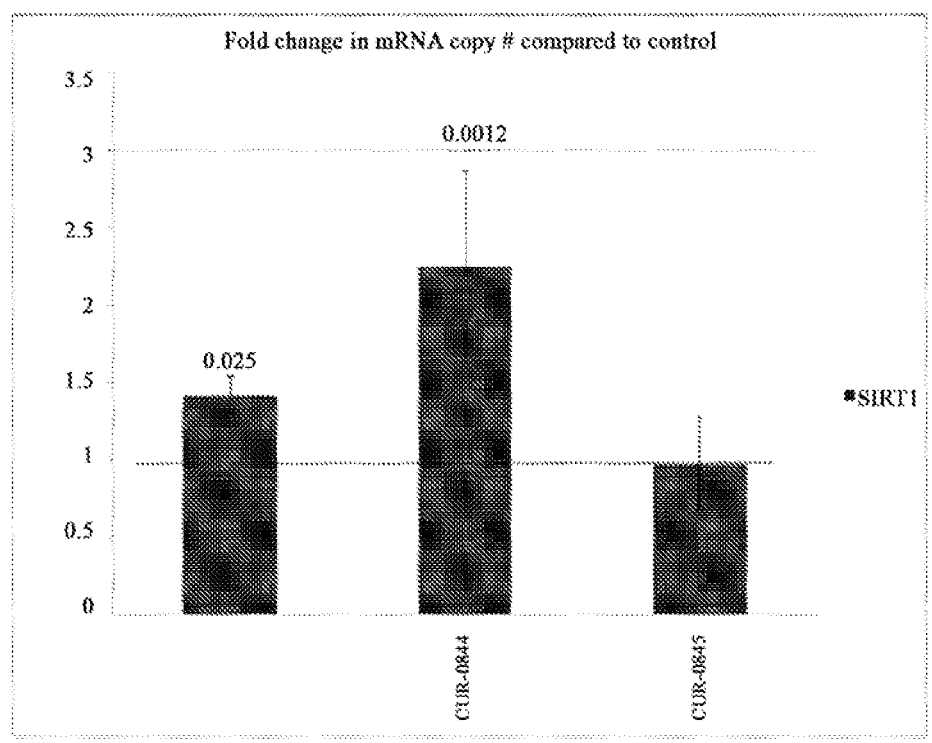
FIG. 15 is a graph of real time PCR results showing the fold change+standard deviation in SIRT1 mRNA after treatment of 3T3 cells with phosphorothioate oligonucleotides introduced using Lipofectamine 2000, as compared to control. Real time PCR results show that the levels of SIRT1 mRNA are significantly increased in HepG2 cells 48 h after treatment with two of the oligonucleotides designed to SIRT1 mouse antisense AK044604. Bars denoted as CUR-0842, CUR-0844, and CUR-0845 correspond to samples treated with SEQ ID NOS: 61, 63 and 64 respectively.

Real time PCR results show that the levels of SIRT1 mRNA are significantly increased in 3T3 cells 48 h after treatment with two of the oligonucleotides designed to SIRT1 mouse antisense AK044604 (FIG. 15).

Figure 16:
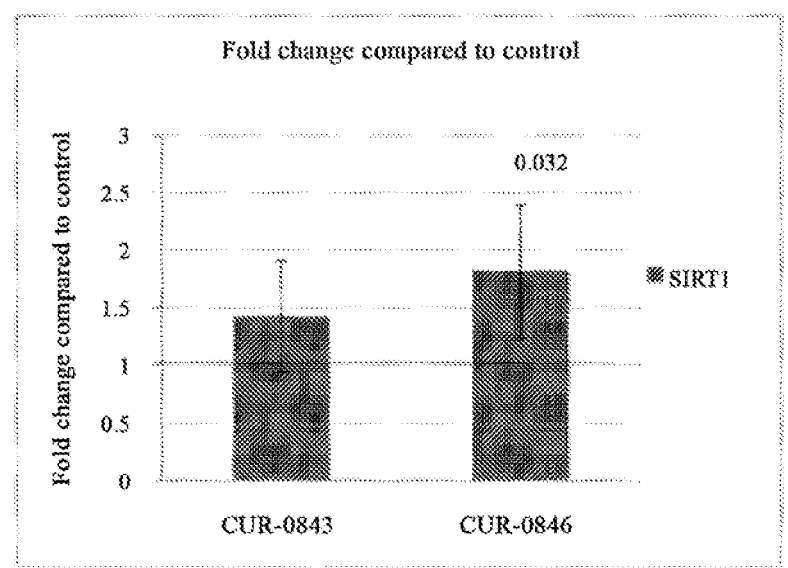
FIG. 16 is a graph of real time PCR results showing the fold change+standard deviation in SIRT1 mRNA after treatment 3T3 cells with phosphorothioate oligonucleotides introduced using Lipofectamine 2000, as compared to control. Real time PCR results show that the levels of SIRT1 mRNA are significantly increased in HepG2 cells 48 h after treatment with two of the oligonucleotides designed to SIRT1 mouse antisense AK044604. Bars denoted as CUR-0843, CUR-0846 correspond to samples treated with SEQ ID NOS: 62 and 65 respectively.

Real time PCR results show that the levels of SIRT1 mRNA are significantly increased in 3T3 cells 48 h after treatment with two of the oligonucleotides designed to SIRT1 mouse antisense AK044604 (FIG. 16).

Treatment of Vero76 Cells with Antisense Oligonucleotides

Vero76 cells from ATCC (cat #CRL-1587) were grown in growth media (MEM/EBSS (Hyclone cat #SH30024, or Mediatech cat #MT-10-010-CV) +10% FBS (Mediatech cat #MT35-011-CV)+ penicillin/streptomycin (Mediatech cat #MT30002-CI)) at 37° C. and 5% CO2. One day before the experiment the cells were replated at the density of $1.5 \times 10^5$/ml into 6 well plates and incubated at 37° C. and 5% CO2. On the day of the experiment the media in the 6 well plates was changed to fresh growth media. All antisense oligonucleotides were diluted in water to the concentration of 20 µM. 2 µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with Vero76 cells. Similar mixture including 2 µl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA isolation System from Promega (cat #Z3105) or RNeasy Total RNA Isolation kit from Qiagen (cat #74181), following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Figure 5:
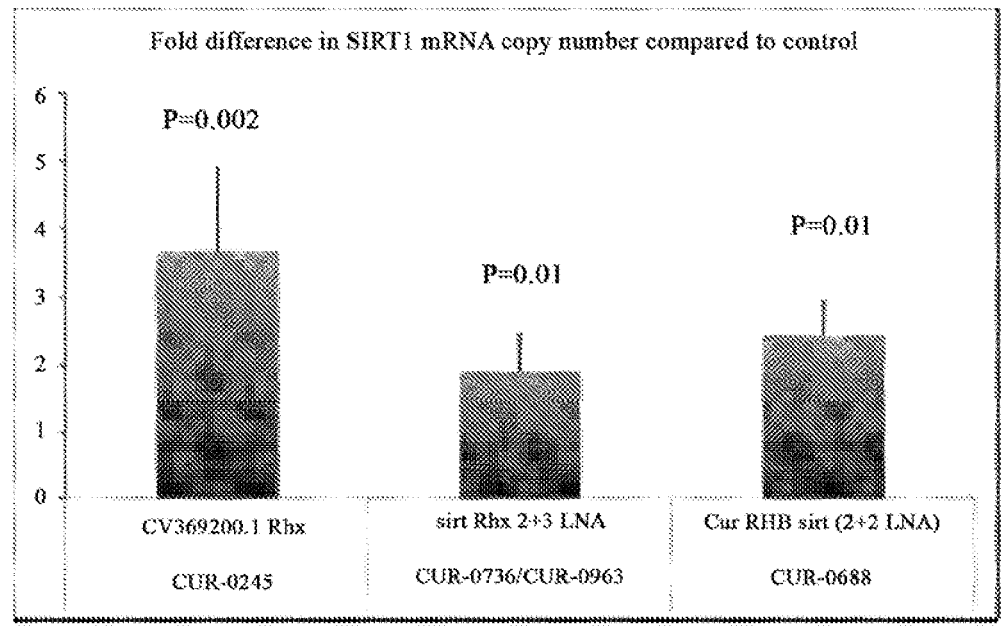

Results: Real time PCT results show that the levels of the SIRT1 mRNA in Vero cells significantly increased 48 h after treatment with antisense oligonucleotides to SIRT1 antisense CV396200 (FIG. 5).

Treatment of DBS Cells with Antisense Oligonucleotides

DBS cells from ATCC (cat #CCL-161) were grown in growth media (MEM/EBSS (Hyclone cat #SH30024, or Mediatech cat #MT-10-010-CV) +10% FBS (Mediatech cat #MT35-011-CV)+ penicillin/streptomycin (Mediatech cat #MT30-002-CI)) at 37° C. and 5% $CO_2$. One day before the experiment the cells were replied at the density of $1.5 \times 10^5$/ml into 6 well plates and incubated at 37° C. and 5% $CO_2$. On the day of the experiment the media in the 6 well plates was changed to fresh growth media. All antisense oligonucleotides were diluted to the concentration of 20 µM. Two µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with 3T3 cells. A Similar mixture including 2 µl of water instead of the oligonucleotide solution was used for the mock-transacted controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00213036_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 20:
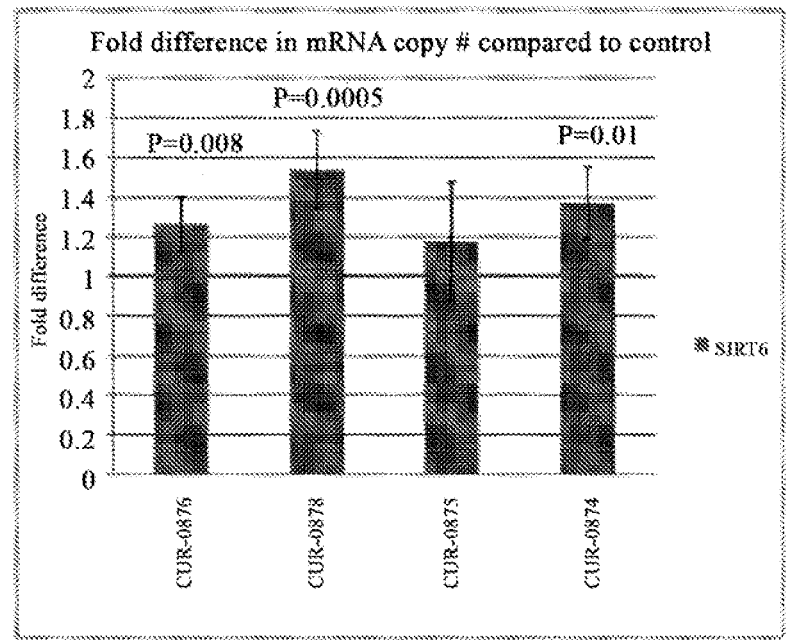
FIG. 20 is a graph of real time PCR results showing the fold change+standard deviation in SIRT6 mRNA after treatment of DBS-FCL-1 with phosphorothioate oligonucleotides introduced using Lipofectamine 2000, as compared to control. Real time PCR results show that the levels of SIRT6 mRNA in DBS-FCL-1 cells are significantly increased after 48 h after treatment with two of the olioigs designed to SIRT6 antisense bf772662 and one oligo designed to NM_133475. Bars denoted as CUR-0876, CUR-0878, to CUR-0875, CUR-0874, correspond to samples treated with SEQ ID NOS: 92, 91, 94 to 89 respectively.

Results: Real time PCR results show that the levels of SIRT6 mRNA in DBS cells are significantly increased 48 h after treatment with two of the oliogs designed to SIRT6 antisense bf772662 and one oligo designed to NM_133475 (FIG. 20).

Example 3: Modulation of SIRT Gene Expression

Material and Methods

Treatment of HepG2 Cells With Naked Antisense Oligonucleotides

HepG2 cells from ATCC (cat #HB-8065) were grown in growth media (MEM/EBSS (Hyclone cat #SH30024, or Mediatech cat #MT-10-010-CV) +10% FBS (Mediatech cat #MT35-011-CV)+ penicillin/streptomycin (Mediatech cat #MT30-002-CI)) at 37° C. and 5% CO2. One day before the experiment the cells were replated at the density of 0.5× $10^5$/ml into 6 well plates and incubated at 37° C. and 5% CO2. On the day of the experiment the media in the 6 well plates was replaced with 1.5 ml/well of fresh growth media. All antisense oligonucleotides were diluted in water to the concentration of 20 μM. 2 μl of this solution was incubated with 400 μl of Opti-MEM media (Gibco cat #31985-070) and 4 ul of Lipofectamine 2000 (Invitrogen cat #11668019) at room temperature for 20 min and applied to each well of the 6 well plates with HepG2 cells. Similar mixture including 2 μl of water instead of the oligonucleotide solution was used for the mock-transfected controls. After 3-18 h of incubation at 37° C. and 5% CO2 the media was changed to fresh growth media. 72 h after addition of antisense oligonucleotides the cell were redosed as described in above. 48 h after the second dosing of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_m1, Hs00202030_m1 and Hs00213036_m1 by Applied Biosystems Inc., Foster City Calif.). The fallowing PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Primers and probe for the custom designed Taqman assay for exon 4: AACTGGAGCTGGGGTGTCTGTTTCA (SEQ ID NO: 95) the SIRT1 natural antisense CV396200.

Forward Primer Seq.
(SEQ ID NO: 96)
CCATCAGACGACATCCCTTAACAAA

Reverse Primer Seq.
(SEQ ID NO: 97)
ACATTATATCATAGCTCCTAAAGGAGATGCA

-continued
Reporter Seq.
(SEQ ID NO: 98)
CAGAGTTTCAATTCCC

Results

Figure 2:
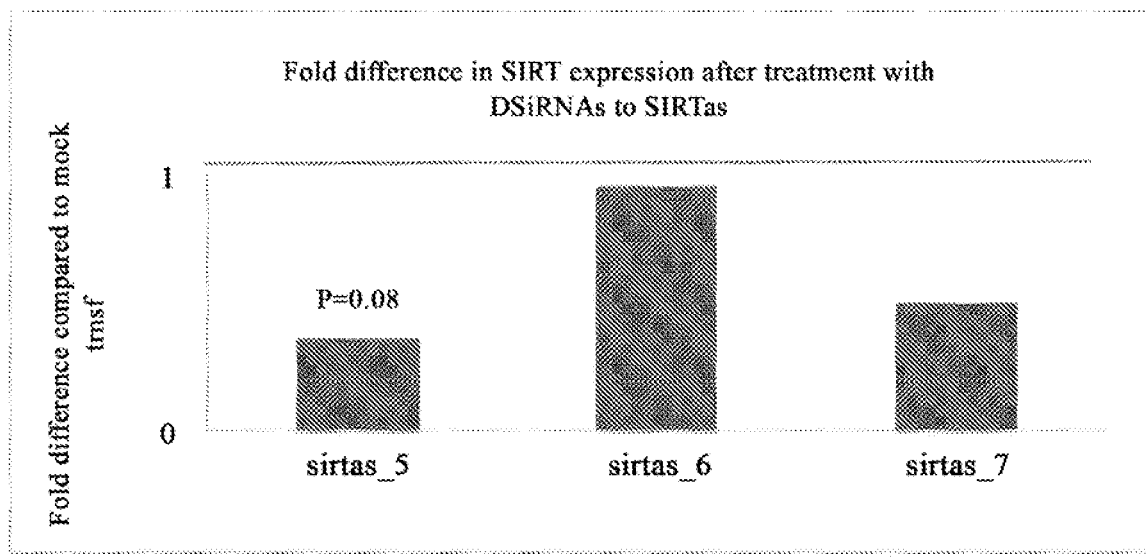

The results show that the levels of the SIRT1 mRNA in HepG2 cells are significantly increased 48 h after treatment with one of the siRNAs designed to sirtas (sirtas_5, P=0.01). In the same samples the levels of sirtas RNA were significantly decreased after treatment with sirtas_5, but unchanged after treatment with sirtas_6 and sirtas_7, which also had no effect on the SIRT1 mRNA levels (FIG. 2), sirtas_5, sirtas_6 and sirtas_7 correspond to SEQ ID NO: 38, 39 and 40 respectively.

Treatment of Primary Monkey Hepatocytes

Primary monkey hepatocytes were introduced into culture by RxGen Inc. and plated in 6 well plates. They were treated with oligonucleotides as follows. The media in the 6 well plates was changed to fresh growth media consisting of William's Medium E (Sigma cat #W4128) supplemented with 5% PBS, 50 U/ml penicillin and 50 ug/ml streptomycin, 4 ug/ml insulin, 1 uM dexamethasone, 10 ug/ml Fungin (InVivogen, San Diego Calif.). All antisense oligonucleotides were diluted to the concentration of 20 μM, 2 μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with cells. Similar mixture including 2 μl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions, 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_m1, Hs00202030_m1 and Hs00213036_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using Mx4000 thermal cycler (Stratagene). Fold change in gene expression after treatment with antisense oligonucleotides was calculated based on the difference in 18S-normalized dCt values between treated and mock-transfected samples.

Figure 7:
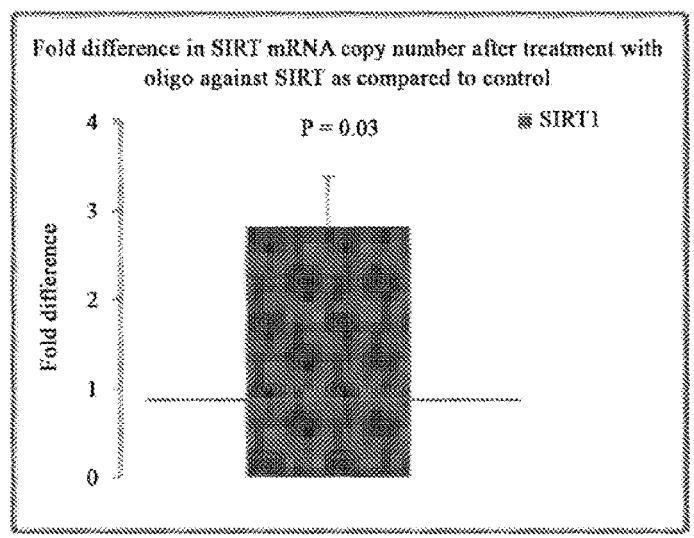
FIG. 7 shows PCR results of primary monkey liver hepatocytes. Real time PCR results show an increase in SIRT1 mRNA levels after treatment with an oligonucleotide against SIRT1 antisense. Bar denoted as CUR-0245 corresponds to SEQ ID NO: 33.

Results: The results are shown in FIG. 7. Real time PCR results show an increase in SIRT1 mRNA levels after treatment with an oligonucleotide against SIRT1 antisense.

Example 4: Efficacy and Duration of Action Study of CUR 963 in the African Green Monkey The objective of this study was to assess and compare the effect of antisense knockdown of the discordant noncoding antisense sequences that regulate the SIRT1 genes following intravenous administration in a nonhuman primate model. The antisense oligonucleotide test articles designed to inhibit the SIRT1 regulatory Sequences were designated as CUR 963.

```
CUR 963:
                                      (SEQ ID NO: 34)
+G*+T*C*T*G*A*T*G*G*+A*+G*+A.

CUR 962 (control):
                                      (SEQ ID NO: 99)
+G*+C*T*A*G*T*C*T*G*+T*+T*+G.
```

Regulatory Test Guidelines

This study was designed in accordance with accepted toxicological principles and to comply with International Conference of Harmonization (ICH) Harmonized Tripartite Guidelines (Non-Clinical Safety Studies for the Conduct of Human Clinical Trials for Pharmaceuticals ICH M3(m), 2000 Nov. 9), and generally accepted procedures for the testing of therapeutic agents.

Test and Control Articles

Test Article Identity and Preparation

The test article, CUR-963, is a chemically stabilised antisense oligonucleotide. The vehicle for intravenous delivery is phosphate-buffered saline (PBS).

Vehicle Characterization

For the PBS vehicle, the composition, batch number, expiry date and storage conditions (temperature and light/dark) was obtained from the supplier.

Test Article Storage and Handling

The test substance and vehicle were stored according to the received storage conditions supplied by the Sponsor and manufacturer, accordingly.

Analysis of the Test Article Formulations

Samples of the test article formulation will be cryopreserved for analysis of the concentration, stability and homogeneity of the test substance formulations.

Test System Rationale

The primate is a suitable non rodent species, acceptable to regulatory authorities as an indicator of potential hazards, and for which extensive background data are available. The African green monkey specifically is a highly clinically relevant model of multiple human physiologic and disease states.

The intravenous route of administration corresponds to a possible human therapeutic route. The dose of the test articles was based on the results of the dose finding studies of analogous compounds previously performed in the African green monkey.

African green monkeys were chosen as the primate of choice as the test substances' target sequences are conserved across species with 100% homology in primates. Additionally, the test substance is a synthetic oligonucleotide. Consequently, dosing in primates allows for a superior assessment of the efficacy of these compounds that would be more reflective of the uptake likely to be seen in humans than in any other species.

Animals

Species: *Chlorocebus sabaeus*, non-human primate
Breed: African, green monkey indigenous to St. Kitts,
Source: RxGen, Lower Bourryeau, St. Kitts, West Indies.
Expected Age: The test animals ware adults.
Expected Body Weight: monkeys weigh approximately 3-4 kg. The actual range may vary but will be documented in the data.
Sex: The test animals were adult females.
Number of Animals: Ten animals were screened to ensure identification of 8 animals appropriate for enrollment in the study.
Number on Study: Females 8
Justification for Number on Study: This study was designed to use the fewest number of animals possible, consistent with the primary objective of evaluating the therapeutic efficacy of the test article in the African green monkey and prior studies of the systemic administration of this type of oligonucleotide in this species.
Animal Specification: Ten adult African Green monkeys in the weight range of 3 to 4 kg, were employed in the study. The monkeys were drug-naïve adult animals humanely trapped from the feral population that inhabits the island. Trapped monkeys were treated with antihelminthics to eliminate any possible intestinal parasite burden and were observed in quarantine for a minimum of 4 weeks prior to screening for study enrollment. The age of trapped monkeys were estimated by size and dentation, with the exclusion of older animals from the study. Prior to study enrollment, a clinical exam was performed on each monkey, including evaluation of locomotion and dexterity. Blood samples were taken and sent to Antech Diagnostics (Memphis, Tenn.) for comprehensive clinical chemistries and a complete blood count and lipid profiles (see sections 9.2 and 319567928 for specifications). Monkeys with abnormal lab values, as determined by comparison to the established normal range for monkeys in the St. Kitts colony, were excluded from the study. In order to identify 8 monkeys that satisfy this criterion, 10 monkeys were screened, with the screening of additional animals as needed. Before study initiation, the selected monkeys will be transferred to individual cages to acclimate to individual housing for a one-week period. Only animals deemed suitable for experimentation will be enrolled in the study. The actual (or estimated) age and weight ranges at the start of the study will be detailed in the raw data and final report.
Animal Health and Welfare: The highest standards of animal welfare were followed and adhered to guidelines stipulated by the St. Kitts Department of Agriculture and the U.S. Department of Health and Human Services. All studies will be conducted in accordance with these requirements and all applicable codes of practice for the care and housing of laboratory animals. All applicable standards for veterinary care, operation, and review as contained in the NIH Guide for the Care and Use of Animals. The St. Kitts facility maintains an animal research committee that reviews the protocols and inspects the facilities as required by the Guide. The Foundation has an approved assurance filed with the Office of Laboratory Animal Welfare, as required by the Guide, #A4384-01 (Axion Research Foundation/St. Kitts Biomedical Foundation). There are no special nonhuman primate veterinary care issues and biohazard issues raised by the research specified in this study.

Housing and Environment: To allow detection of any treatment-related clinical signs, the animals were housed individually prior to surgery and postoperatively until sacrifice. The primate building in which the individual cages were situated were illuminated entirely by ambient light, which at 17 degrees north latitude, approximates a 12 hr:12 hr light-dark cycle as recommended in the U.S. D.H.H.S guidelines. The RxGen primate building was completely ventilated to the outside. Additional air movement was assured by ceiling fans to maintain a constant target temperature of 23-35° C., as is typical of St. Kitts throughout the year. Twenty-four hour extremes of temperature and relative humidity (which also will not be controlled) were measured daily. During the study, the cages were cleaned at regular intervals.

Diet and Water: Each animal was offered approximately 90 grams per day of a standard monkey chow diet (TekLad, Madison, Wis.). The specific nutritional composition of the diet was recorded. The water was periodically analyzed for microbiological purity. The criteria for acceptable levels of contaminants in stock diet and water supply were within the analytical specifications established by the diet manufacturer and the periodic facility water evaluations, respectively. The water met all criteria necessary for certification as acceptable for human consumption.

Experimental Design

Animal Identification and Randomization: Allocation was done by means of a stratified randomization procedure based an bodyweight and plasma cholesterol profiles. Prior to and after allocation to a group, each animal was identified by a tattoo on the abdomen. Tattoos are placed on all colony animals as a means of identification in the course of routine health inspections. A cage plan was drawn up to identify the individuals housed within, and individual monkeys were further identified by a labeled tag attached to their respective cage.

Group sizes, doses and identification numbers: The animals were assigned to 2 treatment groups, comprised of 4 monkeys in each group. Specific animal identification numbers were provided to each monkey according to the facility numbering system. This system uniquely identifies each monkey by a letter followed by a three digit number, e.g., Y032.

Route and Frequency of Administration: Animals were dosed once daily on Days 1, 3, and 5 delivered intravenously by manual infusion over ~10 min. The infusion rate will be 24 mL/kg/h. The animals were selected with ketamine and xylazine prior to and during the dosing procedure. A venous catheter (Terumo mini vein infusion set, 20 gauge needle, or similar appropriate infusion set) was inserted into the saphenous vein. Dosing took place in each monkey between 8:00 and 10:00 a.m. shortly after the animals wake and prior to feeding. A blood sample to assess plasma cholesterol and other lipid levels as described in Blood Chemistry section below, was collected just prior to each infusion. Blood collection preceded feeding at both sampling intervals to minimize dietary effects on cholesterol measurements.

Clinical Observations: All visible signs of reaction to treatment were recorded on each day of dosing. In addition, the animals were examined at least once each week for physical attributes such as appearance and general condition.

Body Weights: Body weights were recorded at weekly intervals during the treatment and post-treatment periods.

Food Consumption: Individual food consumption was not quantified. Feeding patterns were however monitored and a note made of any major changes.

Mortality and Morbidity: Mortality and morbidity will be recorded. Any decision regarding premature sacrifice will be made after consultation with the Study Director and with the Sponsor's Monitoring Scientist, if possible. Animals that are found dead or killed prematurely will be subjected to necropsy with collection of liver, kidney, heart and spleen lung tissues for histopathology. In the event of premature sacrifice a blood sample will also be taken (if possible) and the parameters determined. Animals that are found dead after regular working hours will be refrigerated overnight and necropsies performed at the start of the next working day. If the condition of an animal requires premature sacrifice, it will be euthanized by intravenous overdose of sodium pentobarbital. All research is governed by the Principles for Use of Animals. RxGen is repaired by law to comply with the U.S. Department of Health and Human Services standards for primate facility, which dictates the levels of severity that the procedures within this study, specified as mild, must abide.

Clinical Laboratory Studies

Fat Biopsies: A subcutaneous fat biopsy was performed an all study monkeys except Y77S on study days 26 by tissue extraction through a 1 cm midline incision inferior to the umbilicus. Biopsies were immediately immersed is a labeled cryotube containing 2 mls of RNAlater (Qiagen) and incubated at 4° C. overnight; after which the RNAlater was aspirated and the single tube flash frozen in liquid nitrogen. Following transportation in liquid nitrogen total RNA was isolated for real-time qPCR of target genes.

Figure 6:
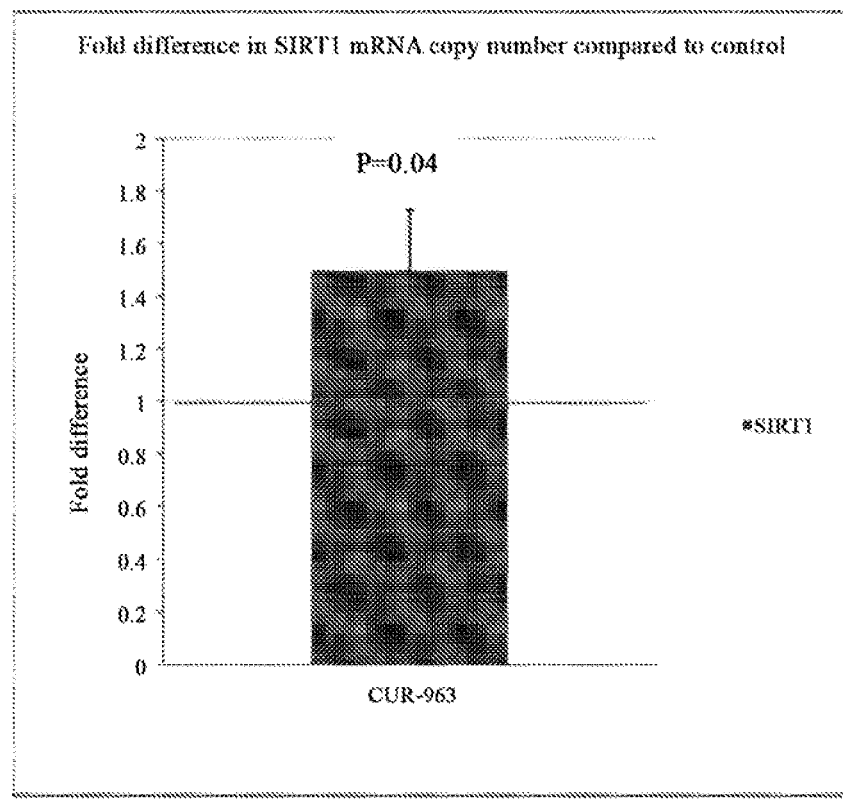
FIG. 6 shows PCR results of Monkey Fat Biopsies. Real time PCR results show an increase in SIRT1 mRNA levels in fat biopsies from monkeys dosed with CUR-963, an oligonucleotide designed to SIRT1 antisense CV396200.1. CUR-963 corresponds to SEQ ID NO:34.

Real time PCR results show an increase in SIRT1 mRNA levels in fat biopsies from monkeys dosed with CUR-963, an oligonucleotide designed to SIRT1 antisense CV396200.1, compared to monkeys dosed with CUR-962 (SEQ ID NO.: 99), an oligonucleotide which had no effect on SIRT1 expression in vitro (designed to ApoA1 antisense DA327409, data not shown). mRNA levels were determined by real time PCR (FIG. 6).

Example 5: In Vivo Modulation of Sirtuin (SIRT) by Antisense DNA Oligonucleotides Treatment with Antisense DNA Oligonucleotides (ASO); Antisense oligonucleotides (ASO) specific for SIRT1 AS are administered to C57B1/6J mice which are fed a high fat diet for 12 weeks to induce obesity and diabetes. (Purushotham A. et al., (2009) Cell Metabolism 9, p. 237-338,). The treatment of the mice with ASO will start at the time of the implementation of the high fat diet. Mice are injected IP once a week with ASO prepared in normal saline, at a concentration of 5 mg/kg.

Measurements of body weight and food intake: Body weight and food intake of mice are measured twice per week, prior to IP injection of the ASO.

Blood glucose measurements: Fed and fasted blood glucose concentrations are measured each week by taking a sample of blood from the tail vein.

Glucose Tolerance Tests (GTT): The GTT will be done totally twice per mouse, halfway through the diet (at week 4) and near the end (at week 10) of the high fat diet. The GTT will inform us about the glucose tolerance of the mice that is the capacity to rapidly clear a glucose bolus front the blood stream. This is a measure for diabetes. Mice are fasted overnight for 16 hours. Mice are injected IP glucose 2 g/kg. This translates into a final volume of 0.2 ml 30% (w/v) glucose solution for a mouse of 30 g weight. Glucose measurements are taken prior to glucose injection and at 5, 15, 30, 60, 90 and 120 min post-injection. Glucose is measured by cutting the tail tip 1 mm from the end of the tail under isoflurane anesthesia prior to IP glucose injection. The blood droplet is aspirated into a strip and glucose concentration is measured with a glucometer. The GTT will be done totally twice per mouse, halfway through the diet (at week 4) and near the end (at week 10) of the high fat diet. The GTT will inform us about the glucose tolerance of the mice that is the capacity to rapidly clear a glucose bolus from the blood stream. This is a measure for diabetes.

Insulin Tolerance Test (ITT): Mice are fasted for 6 hours from 9 am till 3 pm. Mice are then injected IP 0.5-1 U Insulin/kg. The insulin concentration will be adjusted such that the final injected volume is 0.1-0.15 ml. Blood glucose measurements are taken prior to injection and at 5, 15, 30, 45, and 60 minutes post-injection. Blood is collected exactly as described under GTT. In addition to monitoring (the glucose levels, the behavior of the mice is constantly observed during the ITT. Hypoglycemia can manifest as a change in behavior with the animals becoming very quiet and showing discomfort. To prevent hypoglycemia, glucose (1 g/kg) is injected IP in a final volume of 0.1-0.15 ml as soon as the blood glucose concentration falls below 50 mg/ml or signs of discomfort are observed.

Blood Collection by Facial Vein Puncture: Mice are restrained by the scruff of the neck and base of the tail, slightly compressing the blood vessels of the neck through the tautness of the grip on the neck skin. The sampling site is on the jaw slightly in front of the angle of the mandible. The skin at the sampling site is punctured with an 18 G needle or a lancet at a 90° angle until the tip of the needle/lancet just passes through the skin. Blood samples are collected using microhematocrit tubes. After blood has been collected, the grip on the neck is loosened and pressure is applied at the insertion site with a gauze sponge to ensure hemostatis. 0.05-0.2 ml of blood will be collected by this method. This procedure will be performed only once in week 5 of the high fat diet and eventually in week 12 if the intracardiac puncture is not working (see below). Blood hormones which regulate the metabolism of glucose and lipids (such as insulin, adiponectin and leptin) are measured using commercially available ELISA kits, (e.g., R&D Systems, Minneapolis, Minn., Assay Pro St. Charles, Mo., Mabtech, Mariemont, Ohio)

Intracardiac Puncture: At the end of the 12 week high fat diet, mice will be anesthetized by continuous isoflurane inhalation. Anesthesia is induced by placing the mice in an induction box, which is supplied with isoflurane and oxygen. Mice will be restrained on their back. The heart is punctured with a 27 G needle. Following exsanguineation, the head is decapitated to ensure death. Tissues (liver, pancreas, white and brown adipose tissue, and skeletal muscle) are collected for further investigations (RNA and protein measurements and histology). Around 0.5-1 ml of blood will be obtained and used to determine several critical parameters of glucose and lipid metabolism (glucose, insulin, cholesterol, triglycerides, free fatty acids, leptin, adipokines, corticosteroids, thyroid hormones). If difficulties occur in this method, we will collect blood by facial vein puncture under isoflurane anesthesia instead (see above).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

TABLE 1

Shows Exemplary Antisense Oligonucleotides

| SEQ ID NO: | SEQ NAME | SEQUENCE |
| --- | --- | --- |
| 15 | CUR-0292 | T*T*G*G*T*A*T*T*A*C*A*A*G |
| 16 | CUR-0293 | A*A*A*C*T*G*G*A*A*A*C*C*T*A |
| 17 | CUR-0294 | G*A*T*C*T*T*T*A*T*G*A*G*A*A |
| 18 | CUR-0295 | G*A*T*G*G*A*G*A*A*A*T*T*G*G |
| 19 | CUR-0296 | A*G*T*C*T*G*A*T*G*G*A*G*A*A |
| 20 | CUR-0297 | T*G*T*T*A*A*G*G*G*A*T*G*T*C |
| 21 | CUR-0298 | A*A*T*C*T*G*C*T*T*T*T*G*G*T*T |
| 22 | CUR-0299 | A*G*G*G*A*A*T*T*G*A*A*A*T*C |
| 23 | CUR-0300 | T*A*A*G*G*C*A*A*G*A*T*T*T*C |
| 24 | CUR-0301 | T*A*A*A*T*G*G*A*G*T*T*A*A*G |
| 25 | CUR-0302 | T*T*A*T*T*T*A*T*A*G*C*A*C*A |
| 26 | CUR-0303 | T*T*G*C*T*TC*T*G*C*T*T*A*T |

TABLE 1-continued

Shows Exemplary Antisense Oligonucleotides

| SEQ ID NO: | SEQ NAME | SEQUENCE |
|---|---|---|
| 27 | CUR-0304 | A*A*A*A*A*A*T*A*T*T*T*G*C |
| 28 | CUR-0305 | C*A*G*C*C*T*T*A*A*A*A*A*A |
| 29 | CUR-0306 | T*T*T*T*A*A*A*C*C*T*C*T*C |
| 30 | CUR-0307 | T*A*G*T*T*C*A*G*A*T*T*T*T |
| 31 | CUR-0308 | A*G*C*A*G*T*T*G*C*T*A*A*T |
| 32 | CUR-0309 | C*T*G*A*G*T*C*C*A*G*C*A*G*C |
| 33 | CUR-0245 | G*T*C*T*G*A*T*G*G*A*G*A |
| 34 | CUR-0736/<br>CUR-0963 | +G*+T*C*T*G*A*T*G*+A*+G*+A |
| 35 | CUR-0688 | +G*+T*C*T*G*A*T*G*A*+G*+A |
| 36 | CUR-0740 | +G*MU*MC\*T*MG*MA*+T*MG*MG*MA*MG*MA |
| 37 | CUR-0644 | MG*MU*MC*MU*MG*MA*MU*MG*MG*MA*MG*MA |
| 38 | SIRTAS_5 | ACTGACACCTAATTGTATTCACATGAA |
| 39 | SIRTAS_6 | TGAGCAGCAGTTGCTAAATTAGTTCA |
| 40 | SIRTAS_7 | TCTACCTACATTATATCATAGCTCCTA |
| 41 | CUR-1230 | T*T*G*G*T*A*T*T*C*A*C*A*A*G*T*G*A*A*A |
| 42 | CUR-1231 | T*T*G*C*T*A*A*A*T*T*A*G*T*T*C*A*G*A*T |
| 43 | CUR-1232 | G*C*A*G*C*A*G*C*A*G*T*T*G*C*T*A*A*A*T |
| 44 | CUR-1233 | G*C*A*G*T*T*G*C*T*A*A*A*T*T*A*G*T*T*C |
| 45 | CUR-1302 | G*C*C*A*T*G*T*T*G*C*C*C*A*G*T*C*A*G*T |
| 46 | CUR-1304 | G*G*G*C*T*C*T*G*C*T*A*C*T*T*A*C*T*T*G*T |
| 47 | CUR-1303 | C*C*C*A*G*T*C*T*T*C*A*G*C*C*T*T*G*T*C*T |
| 48 | CUR-1305 | G*G*G*T*C*T*T*C*T*G*T*C*A*T*A*T*G*C*T*C*T*T |
| 49 | CUR-1264 | T*T*C*C*T*A*C*C*T*T*C*C*C*T*C*C*A*T*A |
| 50 | CUR-1265 | A*T*C*C*T*A*C*C*T*T*C*C*C*T*C*A*T |
| 51 | CUR-1266 | C*C*T*T*A*G*G*G*T*T*G*C*A*G*C*T*A*A*T*T |
| 52 | CUR-1294 | A*T*C*C*C*A*G*C*T*A*C*T*C*A*G*G*A*G*G*C |
| 53 | CUR-1297 | T*C*T*G*G*C*T*G*A*G*T*G*C*A*G*T*G*G*C*T |
| 54 | CUR-1795 | C*C*T*G*G*G*G*A*G*T*T*G*G*A*G*G*T*T*G*C*A |
| 55 | CUR-1296 | C*A*G*A*T*C*C*C*A*T*G*A*A*G*C*C*A*A*G*A*G |
| 56 | CUR-1298 | C*T*G*A*C*T*G*C*C*A*T*C*G*A*G*A*A*G*T*G*G |
| 57 | CUR-1381 | G*C*C*C*A*T*C*T*G*C*T*T*G*C*T*T*G*A*T |
| 58 | CUR-1382 | A*T*C*C*T*C*A*C*C*A*C*A*G*T*C*T*T*G*T |
| 59 | CUR-1383 | G*C*T*T*A*C*T*T*C*T*C*C*T*C*C*C*T*T*T |
| 60 | CUR-1384 | C*C*A*G*G*T*G*A*T*A*G*G*A*G*C*A*G*A*A*C*T |
| 61 | CUR-0842 | A*C*C*C*T*C*C*T*T*C*C*T*C*C*C*T*C*T*C*T |
| 62 | CUR-0843 | C*C*A*C*T*C*T*C*C*C*T*T*C*T*T*G*T*C*C*T*C*T |
| 63 | CUR-0844 | C*C*T*C*C*T*T*T*C*C*T*C*C*C*T*C*T*C*T*C*T |
| 64 | CUR-0845 | G*T*C*T*G*T*C*C*C*A*T*C*A*T*G*C*C*A*G*G |

TABLE 1-continued

Shows Exemplary Antisense Oligonucleotides

| SEQ ID NO: | SEQ NAME | SEQUENCE |
|---|---|---|
| 65 | CUR-0846 | T*T*T*C*T*G*A*T*C*C*T*G*C*T*G*G*C*C*T*C*T |
| 66 | CUR-0948 | A*C*C*T*C*C*T*T*C*C*T*C*C*C |
| 67 | CUR-0949 | C*T*C*C*T*T*C*C*T*C*C*T*C |
| 68 | CUR-0950 | C*T*C*C*T*T*C*C*T*C*C |
| 69 | CUR-0951 | C*T*T*C*C*T*C*C*C*T*C*T*C |
| 70 | CUR-0952 | A*T*C*C*T*G*C*T*G*C*C*T*C*T |
| 71 | CUR-1098 | +C*+T*C*(C*T*T*C*T*C*C*+C*+T*+C |
| 72 | CUR-1099 | +A*+C*C*T*C*C*T*T*C*C*T*+C*+C*+C |
| 85 | CUR-0873 | T*C*C*T*T*C*T*C*C*T*C*T*T*G*T*C*T*C*T*C*C |
| 86 | CUR-0869 | G*C*C*C*T*G*T*G*T*T*T*C*T*C*T*C*T*C*C |
| 87 | CUR-0870 | A*C*T*C*C*C*G*T*G*G*T*C*T*C*T*G*T*G*T*C*T |
| 88 | CUR-0871 | T*C*C*A*G*C*A*A*C*C*T*C*A*C*T*C*T*C*C*C |
| 89 | CUR-0874 | G*C*G*T*G*G*G*T*G*T*G*G*T*C*A*G*T*G*T*A |
| 90 | CUR-0872 | A*C*C*A*C*T*C*T*C*C*T*G*C*T*C*C*A*G*A*C*T |
| 91 | CUR-0878 | C*C*T*C*T*C*C*C*T*C*T*C*T*C*T*G*T*C*T*C*T |
| 92 | CUR-0876 | A*T*C*T*T*C*C*C*T*C*T*C*A*C*C*C*T*T*C |
| 93 | CUR-0877 | C*C*C*T*T*C*T*G*T*C*T*G*A*T*C*T*T*C*C*C*T |
| 94 | CUR-0875 | T*C*T*G*T*G*T*C*C*A*C*C*T*G*T*C*T*C*C*C* |
| 73 | CUR-1551 | G*T*T*C*T*G*G*C*T*C*T*G*C*T*G*T*A*G*G*A |
| 74 | CUR-1552 | A*T*G*C*T*C*A*C*T*C*A*C*T*T*C*C*G*G*C*G |
| 75 | CUR-1555 | C*T*T*T*G*T*G*G*T*G*GT*C*A*G*C*C*T*T*T*G*T |
| 76 | CUR-1556 | A*G*T*G*T*G*A*G*C*G*C*A*G*G*G*T*A*C*A |
| 77 | CUR-1553 | C*T*C*G*G*T*T*A*C*A*G*C*G*T*C*T*C*T |
| 78 | CUR-1554 | A*A*C*T*C*T*C*C*G*G*C*G*T*T*T*G*C*A*G |
| 79 | CUR-1545 | T*G*T*T*G*T*C*C*C*A*G*T*T*A*C*T*C*C*T |
| 80 | CUR-1546 | G*C*C*A*G*G*A*G*T*T*A*A*G*A*G*C*A*G*C |
| 81 | CUR-1548 | C*C*T*T*G*T*T*G*G*C*A*C*C*T*C*A*C*T*G*T |
| 82 | CUR-1549 | G*T*T*G*T*G*C*G*G*T*T*A*A*T*A*C*T*C*C*C |
| 83 | CUR-1550 | G*T*G*A*G*T*C*T*G*C*A*A*G*T*G*G*T*A*G*C*T |
| 84 | CUR-1547 | G*A*C*T*C*T*T*A*T*C*T*A*C*C*T*G*T*G*G*G*A |

What is claimed is:

1. A method of upregulating a function of and/or the expression of a Sirtuin (SIRT) polynucleotide having SEQ ID NOS: 1, 3 or 4 in patient cells or tissues in vivo or in vitro comprising: contacting said cells or tissues with at least one single-stranded antisense oligonucleotide 14 to 24 nucleotides in length wherein said at least one oligonucleotide is 100% complementary and hybridizes to a complementary polynucleotide comprising 12 to 24 nucleotides within nucleotides 1 to 1028 of SEQ ID NO: 5 or nucleotides 1 to 352 and 373 to 429 of SEQ ID NO: 6, or nucleotides 1 to 156 of SEQ ID NO: 7 or nucleotides 269 to 593 of SEQ ID NO:8, 1 to 373 of SEQ ID NO: 9, 1 to 589 of SEQ ID NO: 12, and 1 to 4026 of SEQ ID NO: 14; thereby upregulating a function of and/or the expression of the Sirtuin (SIRT) polynucleotide in patient cells or tissues in vivo or in vitro.

2. The method of claim 1, wherein a function of and/or the expression of the Sirtuin (SIRT) is increased in vivo or in vitro with respect to a control wherein the control is selected from a mock transfected control.

3. The method of claim 1, wherein the at least one antisense oligonucleotide targets a natural antisense polynucleotide antisense to coding nucleic acid sequences of a Sirtuin (SIRT) polynucleotide.

4. The method of claim 1, wherein the at least one antisense oligonucleotide targets a natural antisense polynucleotide having overlapping sequences with a Sirtuin (SIRT) polynucleotide.

5. The method of claim 1, wherein the at least one antisense oligonucleotide comprises one or more modifications selected from: at least one modified sugar moiety, at least one modified internucleoside linkage, at least one modified nucleotide, and combinations thereof.

6. The method of claim 5, wherein the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

7. The method of claim 5, wherein the one or more modifications comprise at least one modified internucleoside linkage selected from: a phosphorothioate, alkylphosphonate, phosphorodithioate, alkylphosphonothioate, phosphoramidate, carbamate, carbonate, phosphate triester, acetamidate, carboxymethyl ester, and combinations thereof.

8. The method of claim 5, wherein the one or more modifications comprise at least one modified nucleotide selected from: a peptide nucleic acid (PNA), a locked nucleic acid (LNA), an arabino-nucleic acid (FANA) and combinations thereof.

9. A method of upregulating a function of and/or the expression of a Sirtuin (SIRT) polynucleotide having SEQ ID NOS: 1, 3 or 4 in mammalian cells or tissues in vivo or in vitro comprising: contacting said cells or tissues with at least one oligonucleotide wherein the at least one oligonucleotide consists of one oligonucleotide sequence selected from SEQ ID NOs: 15, 29-37, 41-51, 56-60, 73-78, 81, 82, 85-90 and 92-94.

10. A method of upregulating a function of and/or the expression of a Sirtuin (SIRT) polynucleotide having SEQ ID NO: 1, 3 or 4 in mammalian cells or tissues in vivo or in vitro comprising: contacting said cells or tissues with at least one single stranded antisense oligonucleotide of about 10 to 24 nucleotides in length having 100% complementarity to noncoding and/or coding sequences of a natural antisense strand of a Sirtuin (SIRT) polynucleotide selected from nucleotides 1 to 411 and 423 to 436 and 456 to 1028 of SEQ ID NO: 5 or nucleotides 1 to 429 of SEQ ID NO: 6, or nucleotides 1 to 156 of SEQ ID NO: 7 or nucleotides 1 to 593 of SEQ ID NO:8, 1 to 373 of SEQ ID NO: 9, 1 to 589 of SEQ ID NO: 12, 1 to 428 of SEQ ID NO: 13 and 1 to 4041 of SEQ ID NO: 14 wherein said at least one antisense oligonucleotide has sequence identity to at least one nucleic acid sequence of 10 to 24 nucleotides in length set forth within SEQ ID NOS: 1, 3 or 4; and, upregulating the function and/or expression of the Sirtuin (SIRT) in mammalian cells or tissues in vivo or in vitro.

11. A method of upregulating a function of and/or the expression of a Sirtuin (SIRT) polynucleotide having SEQ ID NOS: 1, 3 or 4 in patient cells or tissues in vivo or in vitro comprising: contacting said cells or tissues with at least one single-stranded antisense oligonucleotide 14 to 24 nucleotides in length wherein said at least one oligonucleotide is 100% complementary and hybridizes to a complementary polynucleotide comprising 12 to 24 nucleotides within nucleotides 296 to 660 of SEQ ID NO: 11; thereby upregulating a function of and/or the expression of the Sirtuin (SIRT) polynucleotide in patient cells or tissues in vivo or in vitro.

12. A method of upregulating a function of and/or the expression of a Sirtuin (SIRT) polynucleotide having SEQ ID NOS: 1, 3 or 4 in patient cells or tissues in vivo or in vitro comprising: contacting said cells or tissues with at least one single-stranded antisense oligonucleotide of 14 to 24 nucleotides in length or at least one siRNA oligonucleotide of 20-27 nucleotides in length having 100% complementarity with and that targets and hybridizes to a complementary target region of a natural antisense polynucleotide of the Sirtuin (SIRT) polynucleotide; thereby upregulating a function of and/or the expression of the Sirtuin (SIRT) polynucleotide in patient cells or tissues in vivo or in vitro wherein the SIRT natural antisense polynucleotides are selected from nucleotides 296 to 660 of SEQ ID NO: 11.

13. A method of upregulating a function of and/or the expression of a Sirtuin (SIRT) polynucleotide having SEQ ID NOS: 1, 3 or 4 in mammalian cells or tissues in vivo or in vitro comprising: contacting said cells or tissues with at least one short interfering RNA (siRNA) oligonucleotide of 20 to 27 nucleotides in length having 100% complementarity with a target region of a natural antisense polynucleotide of a Sirtuin (SIRT) polynucleotide selected from 1 to 35 and 55 to 660 of SEQ ID NO: 11, and, upregulating a function of and/or the expression of a Sirtuin (SIRT) in mammalian cells or tissues in vivo or in vitro.

* * * * *

UNITED STATES PATENT AND TRADEMARK OFFICE
CERTIFICATE OF CORRECTION

PATENT NO. : 10,563,202 B2  
APPLICATION NO. : 14/701998  
DATED : February 18, 2020  
INVENTOR(S) : Joseph Collard et al.

Page 1 of 1

It is certified that error appears in the above-identified patent and that said Letters Patent is hereby corrected as shown below:

On the Title Page

Item (73), please replace "GuRNA, Inc." with --CuRNA, Inc.--

Signed and Sealed this  
Fifth Day of April, 2022

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 103

<210> SEQ ID NO 1
<211> LENGTH: 4107
<212> TYPE: DNA
<213> ORGANISM: Homo sapiens
<300> PUBLICATION INFORMATION:
<308> DATABASE ACCESSION NUMBER: NM_012238.3

<309> DATABASE ENTRY DATE: 2008-11-30
<313> RELEVANT RESIDUES IN SEQ ID NO: (1)..(4107)

<400> SEQUENCE: 1

| | | | | | |
|---|---|---|---|---|---|
| gtcgagcggg | agcagaggag | gcgagggagg | agggccagag | aggcagttgg | aagatggcgg | 60 |
| acgaggcggc | cctcgccctt | cagcccggcg | gctcccccte | ggcggcgggg | gccgacaggg | 120 |
| aggccgcgtc | gtcccccgcc | ggggagccgc | tccgcaagag | gccgcggaga | gatggtcccg | 180 |
| gcctcgagcg | gagcccgggc | gagcccggtg | gggcggcccc | agagcgtgag | gtgccggcgg | 240 |
| cggccagggg | ctgcccgggt | gcggcggcgg | cggcgctgtg | gcgggaggcg | gaggcagagg | 300 |
| cggcggcggc | aggcggggag | caagaggccc | aggcgactgc | ggcggctggg | gaaggagaca | 360 |
| atgggccggg | cctgcagggc | ccatctcggg | agccaccgct | ggccgacaac | ttgtacgacg | 420 |
| aagacgacga | cgacgagggc | gaggaggagg | aagaggcggc | ggcggcggcg | attgggtacc | 480 |
| gagataacct | tctgttcggt | gatgaaatta | tcactaatgg | ttttcattcc | tgtgaaagtg | 540 |
| atgaggagga | tagagcctca | catgcaagct | ctagtgactg | gactccaagg | ccacggatag | 600 |
| gtccatatac | ttttgttcag | caacatctta | tgattggcac | agatcctcga | acaattctta | 660 |
| aagatttatt | gccggaaaca | atacctccac | ctgagttgga | tgatatgaca | ctgtggcaga | 720 |
| ttgttattaa | tatcctttca | gaaccaccaa | aaaggaaaaa | aagaaaagat | attaatacaa | 780 |
| ttgaagatgc | tgtgaaatta | ctgcaagagt | gcaaaaaaat | tatagttcta | actggagctg | 840 |
| gggtgtctgt | ttcatgtgga | atacctgact | tcaggtcaag | ggatggtatt | tatgctcgcc | 900 |
| ttgctgtaga | cttcccagat | cttccagatc | ctcaagcgat | gtttgatatt | gaatatttca | 960 |
| gaaaagatcc | aagaccattc | ttcaagtttg | caaaggaaat | atatcctgga | caattccagc | 1020 |
| catctctctg | tcacaaattc | atagccttgt | cagataagga | aggaaaacta | cttcgcaact | 1080 |
| atacccagaa | catagacacg | ctggaacagg | ttgcgggaat | ccaaaggata | attcagtgtc | 1140 |
| atggttcctt | tgcaacagca | tcttgcctga | tttgtaaata | caagttgac | tgtgaagctg | 1200 |
| tacgaggaga | tatttttaat | caggtagttc | ctcgatgtcc | taggtgccca | gctgatgaac | 1260 |
| cgcttgctat | catgaaacca | gagattgtgt | tttttggtga | aaatttacca | gaacagtttc | 1320 |
| atagagccat | gaagtatgac | aaagatgaag | ttgacctcct | cattgttatt | gggtcttccc | 1380 |
| tcaaagtaag | accagtagca | ctaattccaa | gttccatacc | ccatgaagtg | cctcagatat | 1440 |
| taattaatag | agaacctttg | cctcatctgc | attttgatgt | agagcttctt | ggagactgtg | 1500 |
| atgtcataat | taatgaattg | tgtcataggt | taggtggtga | atatgccaaa | ctttgctgta | 1560 |
| accctgtaaa | gctttcagaa | attactgaaa | aacctccacg | aacacaaaaa | gaattggctt | 1620 |
| atttgtcaga | gttgccaccc | acacctcttc | atgtttcaga | agactcaagt | tcaccagaaa | 1680 |
| gaacttcacc | accagattct | tcagtgattg | tcacactttt | agaccaagca | gctaagagta | 1740 |
| atgatgattt | agatgtgtct | gaatcaaaag | gttgtatgga | agaaaaacca | caggaagtac | 1800 |
| aaacttctag | gaatgttgaa | agtattgctg | aacagatgga | aaatccggat | ttgaagaatg | 1860 |
| ttggttctag | tactggggag | aaaaatgaaa | gaacttcagt | ggctggaaca | gtgagaaaat | 1920 |
| gctggcctaa | tagagtggca | aaggagcaga | ttagtaggcg | gcttgatggt | aatcagtatc | 1980 |
| tgttttttgcc | accaaatcgt | tacatttttcc | atggcgctga | ggtatattca | gactctgaag | 2040 |
| atgacgtctt | atcctctagt | tcttgtggca | gtaacagtga | tagtgggaca | tgccagagtc | 2100 |
| caagtttaga | agaacccatg | gaggatgaaa | gtgaaattga | agaattctac | aatggcttag | 2160 |
| aagatgagcc | tgatgttcca | gagagagctg | gaggagctgg | atttgggact | gatggagatg | 2220 |

| | |
|---|---|
| atcaagaggc aattaatgaa gctatatctg tgaaacagga agtaacagac atgaactatc | 2280 |
| catcaaacaa atcatagtgt aataattgtg caggtacagg aattgttcca ccagcattag | 2340 |
| gaactttagc atgtcaaaat gaatgtttac ttgtgaactc gatagagcaa ggaaaccaga | 2400 |
| aaggtgtaat atttataggt tggtaaaata gattgttttt catggataat ttttaacttc | 2460 |
| attatttctg tacttgtaca aactcaacac taactttttt ttttttaaaa aaaaaaaggt | 2520 |
| actaagtatc ttcaatcagc tgttggtcaa gactaacttt cttttaaagg ttcatttgta | 2580 |
| tgataaattc atatgtgtat atataatttt ttttgttttg tctagtgagt ttcaacattt | 2640 |
| ttaaagtttt caaaaagcca tcggaatgtt aaattaatgt aaagggacag ctaatctaga | 2700 |
| ccaaagaatg gtattttcac ttttctttgt aacattgaat ggtttgaagt actcaaaatc | 2760 |
| tgttacgcta aacttttgat tctttaacac aattattttt aaacactggc attttccaaa | 2820 |
| actgtggcag ctaactttt aaaatctcaa atgacatgca gtgtgagtag aaggaagtca | 2880 |
| acaatatgtg gggagagcac tcggttgtct ttacttttaa aagtaatact tggtgctaag | 2940 |
| aatttcagga ttattgtatt tacgttcaaa tgaagatggc ttttgtactt cctgtggaca | 3000 |
| tgtagtaatg tctatattgg ctcataaaac taacctgaaa acaaataaa tgctttggaa | 3060 |
| atgtttcagt tgctttagaa acattagtgc ctgcctggat ccccttagtt ttgaaatatt | 3120 |
| tgccattgtt gtttaaatac ctatcactgt ggtagagctt gcattgatct tttccacaag | 3180 |
| tattaaactg ccaaaatgtg aatatgcaaa gcctttctga atctataata atggtacttc | 3240 |
| tactggggag agtgtaatat tttggactgc tgttttccat taatgaggag agcaacaggc | 3300 |
| ccctgattat acagttccaa agtaataaga tgttaattgt aattcagcca gaaagtacat | 3360 |
| gtctcccatt gggaggattt ggtgttaaat accaaactgc tagccctagt attatggaga | 3420 |
| tgaacatgat gatgtaactt gtaatagcag aatagttaat gaatgaaact agttcttata | 3480 |
| atttatcttt atttaaaagc ttagcctgcc ttaaaactag agatcaactt tctcagctgc | 3540 |
| aaaagcttct agtctttcaa gaagttcata ctttatgaaa ttgcacagta agcatttatt | 3600 |
| tttcagacca tttttgaaca tcactcctaa attaataaag tattcctctg ttgctttagt | 3660 |
| atttattaca ataaaaaggg tttgaaatat agctgttctt tatgcataaa acacccagct | 3720 |
| aggaccatta ctgccagaga aaaaaatcgt attgaatggc catttcccta cttataagat | 3780 |
| gtctcaatct gaatttattt ggctacacta aagaatgcag tatatttagt tttccatttg | 3840 |
| catgatgttt gtgtgctata gatgatattt taaattgaaa agtttgtttt aaattatttt | 3900 |
| tacagtgaag actgttttca gctcttttta tattgtacat agtcttttat gtaatttact | 3960 |
| ggcatatgtt ttgtagactg tttaatgact ggatatcttc cttcaacttt tgaaatacaa | 4020 |
| aaccagtgtt ttttacttgt acactgtttt aaagtctatt aaaattgtca tttgactttt | 4080 |
| ttctgttaaa aaaaaaaaaa aaaaaaa | 4107 |

<210> SEQ ID NO 2
<211> LENGTH: 3806
<212> TYPE: DNA
<213> ORGANISM: Mus musculus
<300> PUBLICATION INFORMATION:
<308> DATABASE ACCESSION NUMBER: NM_001159589.1
<309> DATABASE ENTRY DATE: 2010-07-18
<313> RELEVANT RESIDUES IN SEQ ID NO: (1)..(3806)

<400> SEQUENCE: 2

| | |
|---|---|
| gccagtgccg cgcgtcgagc ggagcagagg aggcgagggc ggagggccag agaggcagtt | 60 |
| ggaagatggc ggacgaggtg gcgctcgccc ttcaggccgc cggctcccct tccgcggcgg | 120 |

```
ccgccatgga ggccgcgtcg cagccggcgg acgagccgct ccgcaagagg ccccgccgag    180
acgggcctgg cctcgggcgc agcccggcg agccgagcgc agcagtggcg ccggcggccg     240
cggggtgtga ggcggcgagc gccgcggccc cggcggcgct gtggcgggag gcggcagggg    300
cggcggcgag cgcggagcgg gaggccccgg cgacggccgt ggccggggac ggagacaatg    360
ggtccggcct gcggcgggag ccgagggcgg ctgacgactt cgacgacgac gagggcgagg    420
aggaggacga ggcggcggcg gcagcggcgg cggcagcgat cggctaccga ggtccatata    480
cttttgttca gcaacatctc atgattggca ccgatcctcg aacaattctt aaagatttat    540
taccagaaac aattcctcca cctgagctgg atgatatgac gctgtggcag attgttatta    600 atatccttc agaaccacca aagcggaaaa aagaaaaga tatcaataca attgaagatg      660
ctgtgaagtt actgcaggag tgtaaaaaga taatagttct gactggagct ggggtttctg    720
tctcctgtgg gattcctgac ttcagatcaa gagacggtat ctatgctcgc cttgcggtgg    780
acttcccaga cctcccagac cctcaagcca tgtttgatat tgagtatttt agaaaagacc    840
caagaccatt cttcaagttt gcaaaggaaa tatatcccgg acagttccag ccgtctctgt    900
gtcacaaatt catagctttg tcagataagg aaggaaaact acttcgaaat tatactcaaa    960
atatagatac cttggagcag gttgcaggaa tccaaggat ccttcagtgt catggttcct     1020
ttgcaacagc atcttgcctg atttgtaaat acaaagttga ttgtgaagct gttcgtggag    1080
acatttttaa tcaggtagtt cctcggtgcc ctaggtgccc agctgatgag ccacttgcca    1140
tcatgaagcc agagattgtc ttctttggtg aaaacttacc agaacagttt catagagcca    1200
tgaagtatga caaagatgaa gttgacctcc tcattgttat tggatcttct ctgaaagtga    1260
gaccagtagc actaattcca agttctatac cccatgaagt gcctcaaata ttaataaata    1320
gggaaccttt gcctcatcta cattttgatg tagagctcct tggagactgc gatgttataa    1380
ttaatgagtt gtgtcatagg ctaggtggtg aatatgccaa actttgttgt aaccctgtaa    1440
agctttcaga aattactgaa aaacctccac gcccacaaaa ggaattggtt catttatcag    1500
agttgccacc aacacctctt catatttcgg aagactcaag ttcacctgaa agaactgtac    1560
cacaagactc ttctgtgatt gctacacttg tagaccaagc aacaaacaac aatgttaatg    1620
atttagaagt atctgaatca agttgtgtgg aagaaaaacc acaagaagta cagactagta    1680
ggaatgttga gaacattaat gtggaaaatc cagattttaa ggctgttggt tccagtactg    1740
cagacaaaaa tgaaagaact tcagttgcag aaacagtgag aaaatgctgg cctaatagac    1800
ttgcaaagga gcagattagt aagcggcttg agggtaatca atacctgttt gtaccaccaa    1860
atcgttacat attccacggt gctgaggtat actcagactc tgaagatgac gtcttgtcct    1920
ctagttcctg tggcagtaac agtgacagtg gcacatgcca gagtccaagt ttagaagaac    1980
ccttggaaga tgaaagtgaa attgaagaat ctacaatgg cttggaagat gatacggaga    2040
ggcccgaatg tgctggagga tctggatttg gagctgatgg aggggatcaa gaggttgtta    2100
atgaagctat agctacaaga caggaattga cagatgtaaa ctatccatca gacaaatcat    2160
aacactattg aagctgtccg gattcaggaa ttgctccacc agcattggga actttagcat    2220
gtcaaaaaat gaatgtttac ttgtgaactt gaacaaggaa atctgaaaga tgtattattt    2280
atagactgga aaatagattg tcttcttgga taatttctaa agttccatca tttctgtttg    2340
tacttgtaca ttcaacactg ttggttgact tcatcttcct ttcaaggttc atttgtatga    2400
tacattcgta tgtatgtata attttgtttt ttgcctaatg agtttcaacc ttttaaagtt    2460
```

| | |
|---|---:|
| ttcaaaagcc attggaatgt taatgtaaag ggaacagctt atctagacca agaatggta | 2520 |
| tttcacactt ttttgtttgt aacattgaat agtttaaagc cctcaatttc tgttctgctg | 2580 |
| aactttatt tttaggacag ttaactttt aaacactggc attttccaaa acttgtggca | 2640 |
| gctaactttt taaaatcaca gatgacttgt aatgtgagga gtcagcaccg tgtctggagc | 2700 |
| actcaaaact tggtgctcag tgtgtgaagc gtacttactg catcgttttt gtacttgctg | 2760 |
| cagacgtggt aatgtccaaa caggcccctg agactaatct gataaatgat ttggaaatgt | 2820 |
| gtttcagttg ttctagaaac aatagtgcct gtctatatag gtccccttag tttgaatatt | 2880 |
| tgccattgtt taattaaata cctatcactg tggtagagcc tgcatagatc ttcaccacaa | 2940 |
| atactgccaa gatgtgaata tgcaaagcct ttctgaatct aataatggta cttctactgg | 3000 |
| ggagagtgta atattttgga ctgctgtttt tccattaatg aggaaagcaa taggcctctt | 3060 |
| aattaaagtc ccaaagtcat aagataaatt gtagctcaac cagaaagtac actgttgcct | 3120 |
| gttgaggatt tggtgtaatg tatcccaagg tgttagcctt gtattatgga gatgaataca | 3180 |
| gatccaatag tcaaatgaaa ctagttctta gttatttaaa agcttagctt gccttaaaac | 3240 |
| tagggatcaa ttttctcaac tgcagaaact tttagccttt caaacagttc acacctcaga | 3300 |
| aagtcagtat ttattttaca gacttctttg gaacattgcc cccaaattta aatattcatg | 3360 |
| tgggtttagt atttattaca aaaaaatgat ttgaaatata gctgttcttt atgcataaaa | 3420 |
| tacccagtta ggaccattac tgccagagga gaaaagtatt aagtagctca tttccctacc | 3480 |
| taaaagataa ctgaatttat ttggctacac taaagaatgc agtatattta gttttccatt | 3540 |
| tgcatgatgt gtttgtgcta tagacaatat tttaaattga aaaatttgtt ttaaattatt | 3600 |
| tttacagtga agactgtttt cagctctttt tatattgtac atagacttt atgtaatctg | 3660 |
| gcatatgttt tgtagaccgt ttaatgactg gattatcttc ctccaacttt tgaaatacaa | 3720 |
| aaacagtgtt ttatacttgt atcttgtttt aaagtcttat attaaaattg tcatttgact | 3780 |
| tttttcccgt taaaaaaaaa aaaaaa | 3806 |

<210> SEQ ID NO 3
<211> LENGTH: 2919
<212> TYPE: DNA
<213> ORGANISM: Homo sapiens
<300> PUBLICATION INFORMATION:
<308> DATABASE ACCESSION NUMBER: NM_012239
<309> DATABASE ENTRY DATE: 2010-07-04
<313> RELEVANT RESIDUES IN SEQ ID NO: (1)..(2919)

<400> SEQUENCE: 3

| | |
|---|---:|
| gcgagtccgg aggactcctt ggactgcgcg gaacatggcg ttctggggtt ggcgcgccgc | 60 |
| ggcagccctc cggctgtggg gccgggtagt tgaacgggtc gaggccgggg gaggcgtggg | 120 |
| gccgtttcag gcctgcggct gtcggctggt gcttggcggc agggacgatg tgagtgcggg | 180 |
| gctgagaggc agccatgggg cccgcggtga gcccttggac ccggcgcgcc ccttgcagag | 240 |
| gcctcccaga cccgaggtgc ccagggcatt ccggaggcag ccgagggcag cagctcccag | 300 |
| tttcttcttt tcgagtatta aaggtggaag aaggtccata tcttttctg tgggtgcttc | 360 |
| aagtgttgtt ggaagtggag gcagcagtga caaggggaag cttcccctgc aggatgtagc | 420 |
| tgagctgatt cgggccagag cctgccagag ggtggtggtc atggtggggg ccggcatcag | 480 |
| cacacccagt ggcattccag acttcagatc gccggggagt ggcctgtaca gcaacctcca | 540 |
| gcagtacgat ctcccgtacc ccgaggccat ttttgaactc ccattcttct ttcacaaccc | 600 |
| caagcccttt ttcactttgg ccaaggagct gtaccctgga aactacaagc ccaacgtcac | 660 |

```
tcactacttt ctccggctgc ttcatgacaa ggggctgctt ctgcggctct acacgcagaa      720
catcgatggg cttgagagag tgtcgggcat ccctgcctca aagctggttg aagctcatgg      780
aacctttgcc tctgccacct gcacagtctg ccaaagaccc ttcccagggg aggacattcg      840
ggctgacgtg atggcagaca gggttccccg ctgcccggtc tgcaccggcg ttgtgaagcc      900
cgacattgtg ttctttgggg agccgctgcc ccagaggttc ttgctgcatg tggttgattt      960
ccccatggca gatctgctgc tcatccttgg gacctccctg gaggtggagc cttttgccag     1020
cttgaccgag gccgtgcgga gctcagttcc ccgactgctc atcaaccggg acttggtggg     1080
gcccttggct tggcatcctc gcagcaggga cgtggcccag ctgggggacg tggttcacgg     1140
cgtggaaagc ctagtggagc ttctgggctg gacagaagag atgcgggacc ttgtgcagcg     1200
ggaaactggg aagcttgatg gaccagacaa ataggatgat ggctgccccc acacaataaa     1260
tggtaacata ggagacatcc acatcccaat tctgacaaga cctcatgcct gaagacagct     1320
tgggcaggtg aaaccagaat atgtgaactg agtggacacc cgaggctgcc actggaatgt     1380
cttctcaggc catgagctgc agtgactggt agggctgtgt ttacagtcag ggccaccccg     1440
tcacatatac aaaggagctg cctgcctgtt tgctgtgttg aactcttcac tctgctgaag     1500
ctcctaatgg aaaaagcttt cttctgactg tgaccctctt gaactgaatc agaccaactg     1560
gaatcccaga ccgagtctgc tttctgtgcc tagttgaacg gcaagctcgg catctgttgg     1620
ttacaagatc cagacttggg ccgagcggtc cccagccctc ttcatgttcc gaagtgtagt     1680
cttgaggccc tggtgccgca cttctagcat gttggtctcc tttagtgggg ctattttaa     1740 tgagagaaaa tctgttcttt ccagcatgaa atacatttag tctcctcaaa gggactgcag     1800
gtgttgacat gagttggaaa gggaaccctg ggatacgtgg cgtcccctct attggaacag     1860
tctgaggact gaaggcattt gtccctggat ttattggaga cggcccagct cctccctctg     1920
aaggtggtca cattctgttg actctccata ctcagcctct cctccagaaa cagatctgtt     1980
ccagaacatt ccagcacttt ctatctggcc tccttgtccc cacactacgc cccccaccc     2040 tcgccagggc ttcctctagt gacactgtta gagctaatct ctgagacagg gaaggcatta     2100
ctcacttaaa acccaggctg agtcctggcc acctgctgga ttgtgacata ggaggtggaa     2160
tccactgaac tgctacttct gcacaggctc cttctcctgg ggctgtaccc aggcccagcc     2220
ctgatggctc accctgtcag gcaccagctg ctccctcctg ggctctcacc cacctgcaca     2280
tcctccttcc tagcatcaca ttacctgcgt gtttccccag acaaaagcac ttcccattct     2340
tgaaccttgc ctaccctggg ctgagctgac ggcaatagat ttaatgacag tgactcccag     2400 gaaggggggtc ctgtgacttt gcgccttaat aagaacaaaa ggtggaattg gtgacctagg     2460
aaaactgttg aattctaaaa agaatgaagt tagtttctaa ccctagttaa tgttcctttt     2520
ttattttttg agtcttgccc tgtcactcag ggtggagtgc ggtgttatga tctcagctca     2580
ctgcaacttc cgcctcccgg gtttaagcga ttctcctggg tagctgggat tacaggtgtg     2640
tcccaccaca cctagcacat ggcatatttt gtaatagaga caaggttttg ctatgttggc     2700
caggctggtc tcgaactcct ggcttcaagt gatccaccca cctcggcctc ccaaagtgct     2760
gggattacag gcatgagcca ctgtgcctgg ccccttttatt tgataaattta cacatacatt     2820 tttgtccaaa actcttcttt atttcaagat gatgtttctg tggctatgtg tggtatgtgg     2880
tataaatctc aatctatggt caaaaaaaaa aaaaaaaa                             2919
```

<210> SEQ ID NO 4

<211> LENGTH: 1657
<212> TYPE: DNA
<213> ORGANISM: Homo sapiens
<300> PUBLICATION INFORMATION:
<308> DATABASE ACCESSION NUMBER: NM_016539
<309> DATABASE ENTRY DATE: 2010-07-17
<313> RELEVANT RESIDUES IN SEQ ID NO: (1)..(1657)

<400> SEQUENCE: 4

```
gcttccggcg gaagcggcct caacaaggga aactttattg ttcccgtggg gcagtcgagg      60
atgtcggtga attacgcggc ggggctgtcg ccgtacgcgg acaagggcaa gtgcggcctc     120
ccggagatct tcgaccccccc ggaggagctg gagcggaagg tgtgggaact ggcgaggctg    180
gtctggcagt cttccagtgt ggtgttccac acgggtgccg gcatcagcac tgcctctggc    240
atccccgact tcaggggtcc ccacggagtc tggaccatgg aggagcgagg tctggccccc    300
aagttcgaca ccacctttga gagcgcgcgg cccacgcaga cccacatggc gctggtgcag    360
ctggagcgcg tgggcctcct ccgcttcctg gtcagccaga acgtggacgg gctccatgtg    420
cgctcaggct tccccaggga caaactggca gagctccacg ggaacatgtt tgtggaagaa    480
tgtgccaagt gtaagacgca gtacgtccga gacacagtcg tgggcaccat gggcctgaag    540
gccacgggcc ggctctgcac cgtggctaag gcaagggggc tgcgagcctg caggggagag    600
ctgagggaca ccatcctaga ctgggaggac tccctgcccg accgggacct ggcactcgcc    660
gatgaggcca gcaggaacgc cgacctgtcc atcacgctgg gtacatcgct gcagatccgg    720
cccagcggga acctgccgct ggctaccaag cgccggggag gccgcctggt catcgtcaac    780
ctgcagccca ccaagcacga ccgccatgct gacctccgca tccatggcta cgttgacgag    840
gtcatgaccc ggctcatgaa gcacctgggg ctggagatcc ccgcctggga cggccccgt    900
gtgctggaga gggcgctgcc acccctgccc gcccgccca ccccaagct ggagcccaag    960
gaggaatctc ccacccggat caacggctct atccccgccg gccccaagca ggagccctgc   1020
gcccagcaca acggctcaga gccgccagc cccaaacggg agcggcccac cagccctgcc   1080
ccccacagac cccccaaaag ggtgaaggcc aaggcggtcc ccagctgacc agggtgcttg   1140
gggagggtgg ggcttttgt agaaactgtg gattcttttt ctctcgtggt ctcactttgt    1200
tacttgtttc tgtccccggg agcctcaggg ctctgagagc tgtgctccag gccaggggtt   1260
acacctgccc tccgtggtcc ctccctgggc tccaggggcc tctggtgcgg ttccgggaag   1320
aagccacacc ccagaggtga caggtgagcc cctgccacac cccagcctct gacttgctgt   1380
gttgtccaga ggtgaggctg ggccctcccct ggtctccagc ttaaacagga gtgaactccc   1440
tctgtcccca gggcctccct tctgggcccc ctacagccca ccctacccct cctccatggg   1500
ccctgcagga ggggagaccc accttgaagt ggggggatcag tagaggcttg cactgccttt   1560
ggggctggag ggagacgtgg gtccaccagg cttctggaaa agtcctcaat gcaataaaaa   1620
caatttcttt cttgcaaaaa aaaaaaaaa aaaaaaa                              1657
```

<210> SEQ ID NO 5
<211> LENGTH: 1028
<212> TYPE: DNA
<213> ORGANISM: Homo sapiens

<400> SEQUENCE: 5

```
cttttcactt gtgaatacca attaggtttc cagtttctca taaagatcta acaaataccc      60
aatttctcca tcagactgac atcccttaac aaaagcagag tttcaattcc ctgcatctcc    120
tttaggagct atgatataat gtaggtagaa atcttgcctt aactccattt acccactgtg    180
```

```
ctataaataa gcagaagcaa atatttttt aaggctggag aggttttaaa aatctgaact      240
aatttagcaa ctgctgctgc actcagtttt tggcagttcc caaacatcca ttatcatgta      300
aggataaatc cttctaaacc agaaaaatgt ttcctacttg gaaaaggcat aagaaaatac      360
atatacgacc tccccatgta ctagtcttac atacccagc tccagttaga actataattt       420
ttttgcactc ttgcagtaat ttcacagcat cttcaattgt attaatatct tttcttttt       480 tcctttttgg tggttctgaa aggatattaa taacaatctg ccacagtgtc atatcatcca      540
actcaggtgg aggtattgtt tccggcaata aatctttaag aattgttcga ggatctgtgc      600
caatcataag atgttgctga acaaaagtat atggacctac aataagggg aaaaggctta      660 aagtcaactt atcaagtaat tcaaaatctc atttattttc tgaagtaatg agttagcatt      720
ctgtgagggt ttttgcaaa gtaagaaaat gcaatttaat ggtatttcat tctcggtaca      780
ctcagaatta atgctatatc ccaatgagat taggaagatc taatgaagag ttgggaagac      840 cccttcagc tgtaagtata tatttcaaga gtctaattaa ttaacaacca gaattaagtt       900
cttatggtta atatctagaa acacacacca taataccaaa agtatttaca aaagggttct      960
acgacataga aaatcgtac cagtcctaaa agcctgtact acttatcatt aaaaccacac      1020
aggaaaaa                                                              1028

<210> SEQ ID NO 6
<211> LENGTH: 429
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t

<400> SEQUENCE: 6
cgacganaac ataagcactt ttaatttcct ctctattatg ctacagacaa ggccgaagac       60
tgggtttttt aggttgttta aggctgtaaa gaaaacaaag aacatatgac agagacccta      120
tgcagtctgc aaagcatact acatatttac taccaggccc taccttacta cagaaagttt      180
gctgatccag ctgtgaacat atacccgat gcagatgaaa acaaatacaa aacaaaccta      240
acttgccatt ttggtcacaa gagcaagtaa gtagcagagc cctgttttga tatgaaaatc      300
cagcactgga ctgggcaaca tggcgagacc ccatctctac caaaaatact aaaaaaatag      360
ccgggcatgg tgnggcacat ctgtagtact agctacttgn gaggctgaga caggagaatc      420
atttgagcc                                                              429

<210> SEQ ID NO 7
<211> LENGTH: 156
<212> TYPE: DNA
<213> ORGANISM: Homo sapiens

<400> SEQUENCE: 7
cctgtatata cacacactat gcaatagtct taggtaacta attagctgca accctaaggt       60
agatcaaata gaaaatgtca agtcgccaca atcacatcat cttaattaat atggagggaa      120
```
ggtaggaatc tgttactctt cccaacacta agcttt                              156

<210> SEQ ID NO 8
<211> LENGTH: 593
<212> TYPE: DNA
<213> ORGANISM: Homo sapiens
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t

<400> SEQUENCE: 8
tctcactgtc tcccaggctg gagcgcaatg gtgcaatctt ggctcgctgc aacctccaac      60
tcccaggttc aagtgattct cgtgcctcag cctcctgagt agctgggatt acaggcgcct     120
gccaccatgc ccggctaatt ttagtatttc tagtagagtt gggatttcac catgttggcc    180
aagctgttct cgaactcttg gcttcatggg atctgcccgc ctcggcttcc caaagtgcta    240
ggattacagg cgtgagccac tgcactcagc cagaaaagat tatttaaaat aattgaatgc    300
atgcaactgc agcatctttt gaaatcaaaa gcaaattaat atctgaggtt ttctataatt    360
aactgtcaag gccaatactt ctggttttat tattttggt ttctacttt ctgaggttat     420 cgataaatgg agaaacatga ttaaataaat gctttatctn cacttctcga tggcagtcag    480
ctttaatgga aaatattttc ctataaacct aaattaattt ccggaaaccc cttttgaggt    540
taactaccat tgcactggaa taatctttgg natcccggaa ccctgttcaa ggg           593

<210> SEQ ID NO 9
<211> LENGTH: 373
<212> TYPE: DNA
<213> ORGANISM: Homo sapiens

<400> SEQUENCE: 9
ggcacttcat ggggtatgga acctaaaata gggtgaaaaa taagagttag aaaaagggag      60
gaggaagtaa gctaataaaa ccacaacaga tacattatgc aaaaatccaa caagggcttg    120
agctccaaat tcccaaaaaa gacccatgca ctaaatactt aaccaagcca ttacatttca    180
tcaagcaagc agatgggcag ttaagtgtct tttataaaac gctcaagttc tgctcctatc    240
acctggttac ccctgagcaa tcttcccaga ctttcccact ctgaacctca aatttccttg    300
tctgcagaat ggggatgata atagtacttc tccacaagac tgtggtgagg attaaatgag    360
ttagtcaagt gca                                                       373

<210> SEQ ID NO 10
<211> LENGTH: 1713
<212> TYPE: DNA
<213> ORGANISM: Mus musculus

<400> SEQUENCE: 10
gggctcccct cagcggcctc tggcgcctcc cgcccgcccg accgttcgc tcgctcgctc       60 gctcgctcgc ttgctcgtcc gggatcgccg cggtggttca agtttgcgat ggcgccgcca    120
cttcccacct gggcctcacg cgtgcacctt gcctgcctgc gcctcttcgc ctcaagtcgg    180
cttttacctc aggggctctg gagagcccaa cctggccgac gccggccttc ctgaggagaa    240
ctcctccacc tgccttgccc ttgctctgtg acagctcttc ctcaggttac ccctgtggtc    300
tctcctcagg aagtttgcgc tctctcccaa tctcccttct caagtgcaat ggaatgccca    360

```
agccagccct cggggcctgt tgccctcctg gaaagatctg gcgattgagg acccgcccta    420
tctgctctct ggacccacca ggtcctctgt acctcgcttt agtctttggt aaaattcatc    480
tcttggggca gcaagagaga ggacagaagg gagagtggtt ggttctccac aaacttctgt    540
gttaagagtc agattgggcc tgggctcttg tgacttgggc gattgactga accttttcta    600
agcccagttt ttaatcatct ctaaaatgac agggccagga ccgaaagaga ctgtagctca    660
gttgtaaagt cacgcttgcc agacaacccc gaagccctag agagagggag gaaggagggt    720
aagttgaagg taatctccaa ctacttagga agttcaaaaa aggcctggaa tacataagac    780
ctcgtctcaa aaacgaaatt taaaacgata gaccatgaga aatcagctag tcaggtttaa    840
agtaaatgac attagtttta aaatcctagg cagttgatgg tggcacaggc ctttaatccc    900
agcaagctgg aggagacagg aggaggttca ctaggacagc caaggctaca caaagaaacc    960
ctgtctcgaa aaataatct tacttctaga attgtagaaa tggctctgta gttaacagca   1020
cttgttgctc ctgcagaggc cctaggtttg actcccatca tccacatgac agctcatacc   1080
ttcagatctg acacctgctt ttggtaaaca cagacatgta tggagccaaa gacccaaac   1140 acataaaaat cctctttgtt gttgttttat gagttagggt ttctctgtgt agccctggct   1200
gtccaggaac tctgtagatc aggctgtcct tgaactcaga ggccacctgc ctctgcttct   1260
tgaactgctg ggattaaaga tgtacaccag caagcccagc ataaaaatac atatttaaat   1320 aatttttaa ataatcctta gttccttcac aactctaagc cccttcactt tctagttacc   1380
atgaaattct gagcacctgt atccatttgg atcattaggg ctcaattgca catggttcaa   1440
ttacagtggg gtttccccag attttagagt tagaggcagc aggatcagaa aattaaatcc   1500
atttgcacta ggtaataaat ttgatcccac cctatctcaa aaacaaaaca ctagccacac   1560
gtggcagcac acacctttta caacaggact caggagcctg gcatgatggg acagacctt   1620 actccctgca cttgaggcag atgcaggcaa atctaggcat cctggtgtac atatgaagtt   1680
caggcaagcc agggccacgt aggctcaaag acg                                1713
```

<210> SEQ ID NO 11
<211> LENGTH: 660
<212> TYPE: DNA
<213> ORGANISM: Homo sapiens
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t

<400> SEQUENCE: 11

```
tttttttttt tttttttccc acaggtagat aagagtcttg ctctgtcacc caggctggag     60
tgcagtggct caatcatagc tcactgcagc cttgaactcc tggactcaag ggatcctctt    120
gccttagtct caggagtaac tgggacaaca ggcttgcgcc accatgcccg gctaattttt    180
aaattttggg tagagatggg gtctcgtta tgttgcccag gctgctcttg aactcctggc    240
ctcgagcgat cccgtctca gcctccgaaa gtgctggtat tacaagtgtg agctaccact    300
tcgagactca cttttcacca acattttcag cagttgtgtc agacagcaag tcaatgtgcc    360
attatttact taaatattca tccattatag ggcatctgat acctaacaac catggacctt    420 aagattttt cctatgtagc ctcagttctt agatgcaatt actatggaga cgggtacgat    480
```

| cacatgccag tgggagtatt aaccgcacaa catttatgag ggatcattaa agcgttaaat | 540 |
| gcatatactt ttggacctag caatcccagt actaggaatt tatgcanaca gtgaggtgcc | 600 |
| aacaaggtta ttcaccacag catgatgnca caatactaaa ggttagaacg tatttcaatg | 660 |

<210> SEQ ID NO 12
<211> LENGTH: 589
<212> TYPE: DNA
<213> ORGANISM: Homo sapiens

<400> SEQUENCE: 12

| agtctggtgt ctcatctctc gccccggagg tcaaacctgg agccagcatt tctgtaccct | 60 |
| gcgctcacac cttttcaac ccggatggcg gtgatagtta atactttctg agcgctttta | 120 |
| ctatggtcag gcattatatt tacacctaat cctcgcaaaa cactactggg aagatcctca | 180 |
| tttgacagga gcaattccgg gtcacaaagg ctgacaccac aaagctagtc cgtagcgggt | 240 |
| tcgaccacag gcgcccacac tctttgacgc ctcaatggca cagccaagtg cgcgggaagt | 300 |
| gggctgcaaa cgccggagag ttttgtccgg agcgcagaga cgcgctgtaa ccgagcaacc | 360 |
| agcggggccc gccccggcc tgctacggcg ctcccagcct gccccgcgcc gctcggcgcc | 420 |
| ggaagtgagt gagcatttcc ggcagccatc cccgcggtgc tgacatcccg gttgttcttc | 480 |
| tgtgccgggg gtcttcctgc tgtcatgaag gacgtaccgg gcttcctaca gcagagccag | 540 |
| aactccgggc ccgggcagcc cgctgtgtgg caccgtctgg aggagctct | 589 |

<210> SEQ ID NO 13
<211> LENGTH: 428
<212> TYPE: DNA
<213> ORGANISM: Homo sapiens

<400> SEQUENCE: 13

| agggtgagtt gcaagacagg aagaggggga tagaacaaga cacagacaga gagataaaga | 60 |
| gttaaagaca aagcaagtca gagacagaat tggagagaga cagagagagg gagaggcaga | 120 |
| gagagagaga tgaattcaca cgaaggcaaa aatgacttat tctattcaac caacactgct | 180 |
| gctgcaatga gcccgacgat gctcacatgg gcccaagccc tgccctccag aagcccttga | 240 |
| tcttggggga gacaggtgga cacagatcct ctggccccaa gagtcaagcc tggatcagag | 300 |
| gaggtacctg ggcctgggga agcccgtgg aggtgggggc cctggggcac gtggaagggc | 360 |
| ttcctggagg aggctaagca gtttcttgaa gggtgagagg gaagatcaga cagaagggat | 420 |
| cctctaga | 428 |

<210> SEQ ID NO 14
<211> LENGTH: 4041
<212> TYPE: DNA
<213> ORGANISM: Homo sapiens

<400> SEQUENCE: 14

| gtggcctgga ggactcattt aagaatcatg tgttgagtac ctactttgta ctgggcacac | 60 |
| tggagagcaa aggtggtacc atctatgccc tggtggctgc gggtggacac aaacatgtga | 120 |
| ccaggggcca ggactggtca ggaaggagga agcggtcctt ttgaggaggg cgaggcaacg | 180 |
| gaccctgccg cccaccagga ctggtgtccc tcaccttacc cccacccttg ccctcctcag | 240 |
| gtggcctgtg gagaggagaa acacagggca ccaactatga agactctcag ggcgcgattt | 300 |
| aagaagacag agctgcggct cagccccact gaccttggct cctgcccgcc ctgcggcccc | 360 |
| tgccccatcc cgaagccggc agccagaggc aggcgccaga gtcaagactg ggcaagagt | 420 |

```
gacgagaggc tgctacaagc cgtggaaaac aacgatgcac ctcgggtggc cgccctcatc      480
gcccgcaagg ggctggtgcc cacgaagcta gaccccgagg gcaagtccgc gttccacctg      540
gcggccatgc ggggtgcggc cagctgtctg gaggtgatga tagctcatgg cagcaatgtc      600
atgagcgcgg acggggcagg ttacaatgcc ctccacctgg ccgccaaata cgggcaccca      660
cagtgcttga agcaactact gcaggcttcc tgcgtggtgg acgtcgtgga cagcagcggg      720
tggactgccc tacaccatgc agcggctggt ggctgtctct cctgctcaga ggtgctctgc      780
tcctttaagg cacatctaaa cccccaagat cggtcaggcg caacaccccct cattatagca      840 gctcagatgt gtcacacaga cctgtgccgt ctcctactgc agcaagggc tgccgcgaac       900 gatcaggacc tgcaaggcag gacggccctg atgctggcct gtgaggggc cagccccgaa       960 acagtggagg tcctgctgca gggcggagcc cagccgggca tcaccgatgc gctggggcag     1020
gacgcggctc actatggcgc cctggcgggg gacaaactca tcctgcacct tctgcaagag     1080
gcggcccagc gcccctcccc acccagcgcc ctcacagagg atgattcagg cgaggcgtca     1140
tctcagaact ctatgtccag ccatggaaag caggggcccc caagaagcg gaaggcgcct     1200 ccacctcccg ccagcattcc catgccggat gatcgagatg cctatgagga gatcgtgagg     1260
ctgcggcagg agaggggccg cctcctgcag aagatccggg gcctggaaca gcacaaggaa     1320
cggaggcagc aggagtcccc ggaggccagc tccctgcaca tcctggagag acaggtgcaa     1380
gagctacagc agttgctggt ggagagacaa gaggagaagg agagcctggg acgggaggtg     1440
gagagtttgc agagccggct gtccctgctg gagaacgagc gggagaatac tagctatgac     1500
gtaaccaccc tgcaggatga ggagggtgag ctgcctgacc ttccaggggc cgaggtgctg     1560
ctgtccagac aactcagtcc gtcggcccag gaacacctgg cctcgctgca ggaacaggtg     1620
gctgtgctca ccagacagaa ccaggaactg atggagaagg tccagatcct ggagaacttt     1680
gagaaggacg agacacagat ggaagtggaa gctttggcag aggtcatccc tcttgccctc     1740
tatgactctc tccgggccga gtttgaccag ctacgcaggc agcacgctga ggccctgcag     1800
gccctgaggc agcaggagac acgagaggtc cccagagaag aggggcagc ctgtggggag      1860 agtgaggttg ctggagccac ggccaccaaa aacgggccaa cccacatgga gctaaatggc     1920
tcagtggctc cagaaaccaa agttaacgga gccgagacca tagatgagga ggctgcagga     1980
gatgaaacca tggaagccag gactatgaag ctgaggcca cggagccga ggccacggga       2040 gctgaggcca caggagccaa ggtcacagaa acaaaaccca caggggctga ggtcagagaa     2100
atggagacca caagaagaga agcaaacatg gaaactaagc ccacaggagc tcaggccaca     2160
gacacagaga ccacgggagt ggaggccatg ggggtggagg ccacaaaaac aaaagcagag     2220
gaagcagaaa tgcaggccta cggagtgggt gctgggcaag cagagccccc agtcacaggg     2280
accacaaaca tggaggccac gggctctagg gccacaggga tggaatccac aggagtcagt     2340
gccacaggtg tggagaaccc aggggtagag gccacggtcc cggggatctc tgctggcccc     2400
atcctacatc ctggtgccgc agaggcctcg gaaaagcttc aagtagagct ggagaccagg     2460
atccgtggct tggaggaggc tctccggcag cgggagcggg aggcagctgc ggagctggag     2520
gcggccctgg ggaagtgcga ggccgcggag gccgaggcag gccggctgcg agagcgtgtc     2580
cgcgaggccg agggcagcgg ggccagcggg ggcggtggcg gtgacaccac acagctgcgg     2640
gcggccctgg agcaggcccg ggaggacctc gagaccgggg actccgcct gcggagctg       2700 gaggcggcct cggcctgcct ggatgaggct cgggccagcc ggctgctggc ggaggaggag     2760
```

| | |
|---|---:|
| gcgcggggcc tgcgggccga gctggcccag cgggaggagg cgcggctgga gcagagccgg | 2820 |
| gagctggagg ttctgcggga gcagctggcc acggccaggg ccacggggga gcagcagcgc | 2880 |
| acggcggccg cggaactggg ccgggcacgg gacgccgctg aggcccgagt ggctgagctg | 2940 |
| cctgcggcct gcgaggaggc gcggcagggc ctggccgagc tgcgggaggc ctccgaggcc | 3000 |
| ctccgccagt ccgtggtgcc ggcctctgag caccgccggc tgcaggagga ggccctggag | 3060 |
| ctgcggggcc gggcagccag tctggagcag gaggtggtgg ccacgggcaa ggaggccgcc | 3120 |
| cggctgcgcg cggagctgga gcgggagcgt gtgtgcagcg tggcgctctc ggagcacgaa | 3180 |
| cgcatcgtgg gcaccctgca ggccaacgtg gcccagctgg aggggcagct ggaggagctg | 3240 |
| ggacggcggc atgagaagac cagcgcagag gtcttccagg tgcagcgtga ggccctgttc | 3300 |
| atgaagagtg agcgacacgc agccgaggca cagctggcca cagcagagca gcagctacgg | 3360 |
| gggctacgga ccgaggcgga aagggctcgc caggcccaga gccgggccca ggaggctctg | 3420 |
| gacaaggcca aggagaagga caagaagatc acagaactct ccaaagaagt cttcaatctt | 3480 |
| aaggaagcct tgaaggagca gccggccgcc ctcgccaccc ctgaggtgga ggctctccgt | 3540 |
| gaccaggtga aggatttaca gcagcagctg caggaagctg ccaggaccac ctccagcgtg | 3600 |
| gtggctttgt acagaagcca cctcctatat gccattcagg gccagatgga tgaagatgtg | 3660 |
| cagcggattc tcagccagat tctgcagatg cagagactcc aggctcaggg ccgctgagaa | 3720 |
| aggccaggcc cagtggctac actgaccaca cccacgcagg gacctcaccc cctgcaggc | 3780 |
| cccttgcaga ccggcttcac ttggcttcac ttggccctat ccaggcccat gcacttggag | 3840 |
| accagcctgg ttccctgccc gaccaccccc agctggctcc atcacccac ctggtctctg | 3900 |
| cacgcacaca ctggtcagtc tggacccggg ccgtgactgc ccctccccca ccaccggaga | 3960 |
| ctgtgattcc ctgtgtcctc cacatccaga cgccagccca ggaataaagg cattctgtgc | 4020 |
| acagggaaaa aaaaaaaaa a | 4041 |

<210> SEQ ID NO 15
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 15
ttggtattca caag                                              14

<210> SEQ ID NO 16
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 16
aaactggaaa ccta                                              14

<210> SEQ ID NO 17
<211> LENGTH: 14
<212> TYPE: DNA
<213> ORGANISM: Artificial Sequence
<220> FEATURE:
<223> OTHER INFORMATION: Antisense Oligonucleotide

<400> SEQUENCE: 17
gatctttatg agaa                                              14

```
<210> SEQ ID NO 18
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 18
gatggagaaa ttgg                                                       14

<210> SEQ ID NO 19
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 19
agtctgatgg agaa                                                       14

<210> SEQ ID NO 20
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 20
tgttaaggga tgtc                                                       14

<210> SEQ ID NO 21
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 21
aatctgcttt tgtt                                                       14

<210> SEQ ID NO 22
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 22
agggaattga aatc                                                       14

<210> SEQ ID NO 23
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 23
taaggcaaga tttc                                                       14

<210> SEQ ID NO 24
<211> LENGTH: 14
<212> TYPE: DNA
<213> ORGANISM: Artificial Sequence
<220> FEATURE:
```

<223> OTHER INFORMATION: Antisense oligonucleotide

<400> SEQUENCE: 24
taaatggagt taag                                                            14

<210> SEQ ID NO 25
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 25
ttatttatag caca                                                            14

<210> SEQ ID NO 26
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 26
ttgcttctgc ttat                                                            14

<210> SEQ ID NO 27
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 27
aaaaaaatat ttgc                                                            14

<210> SEQ ID NO 28
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 28
cagccttaaa aaaa                                                            14

<210> SEQ ID NO 29
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 29
ttttaaaacc tctc                                                            14

<210> SEQ ID NO 30
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 30
tagttcagat tttt                                                            14

<210> SEQ ID NO 31
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 31
agcagttgct aaat                                                        14

<210> SEQ ID NO 32
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 32
ctgagtgcag cagc                                                        14

<210> SEQ ID NO 33
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 33
gtctgatgga ga                                                          12

<210> SEQ ID NO 34
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 34
gtctgatgga ga                                                          12

<210> SEQ ID NO 35
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 35
gtctgatgga ga                                                          12

<210> SEQ ID NO 36
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 36
guctgatgga ga                                                          12

<210> SEQ ID NO 37
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 37
gucugaugga ga                                                              12

<210> SEQ ID NO 38
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 38
actgacacct aattgtattc acatgaa                                              27

<210> SEQ ID NO 39
<211> LENGTH: 26
<212> TYPE: DNA
<213> ORGANISM: Artificial Sequence
<220> FEATURE:
<223> OTHER INFORMATION: Antisense oligonucleotide

<400> SEQUENCE: 39
tgagcagcag ttgctaaatt agttca                                               26

<210> SEQ ID NO 40
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 40
tctacctaca ttatatcata gctccta                                              27

<210> SEQ ID NO 41
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 41
ttggtattca caagtgaaa                                                       19

<210> SEQ ID NO 42
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 42
ttgctaaatt agttcagat                                                       19

<210> SEQ ID NO 43
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 43
gcagcagcag ttgctaaat                                                       19

<210> SEQ ID NO 44
<211> LENGTH: 19

```
<212> TYPE: DNA
<213> ORGANISM: Artificial Sequence
<220> FEATURE:
<223> OTHER INFORMATION: Antisense oligonucleotide

<400> SEQUENCE: 44
gcagttgcta aattagttc                                                 19

<210> SEQ ID NO 45
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 45
gccatgttgc ccagtccagt                                                20

<210> SEQ ID NO 46
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 46
gggctctgct acttacttgc                                                20

<210> SEQ ID NO 47
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 47
cccagtcttc agccttgtct                                                20

<210> SEQ ID NO 48
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 48
gggtctctgt catatgttct t                                              21

<210> SEQ ID NO 49
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 49
ttcctacctt ccctccata                                                 19

<210> SEQ ID NO 50
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 50
```

```
attcctacct tccctccat                                                19

<210> SEQ ID NO 51
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 51
ccttagggtt gcagctaatt                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 52
atcccagcta ctcaggaggc                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 53
tctggctgag tgcagtggct                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 54
cctgggagtt ggaggttgca                                               20

<210> SEQ ID NO 55
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 55
cagatcccat gaagccaaga g                                             21

<210> SEQ ID NO 56
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 56
ctgactgcca tcgagaagtg g                                             21

<210> SEQ ID NO 57
<211> LENGTH: 19
<212> TYPE: DNA
<213> ORGANISM: Artificial Sequence
```

```
<220> FEATURE:
<223> OTHER INFORMATION: Antisense oligonucleotide

<400> SEQUENCE: 57
gcccatctgc ttgcttgat                                                    19

<210> SEQ ID NO 58
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 58
atcctcacca cagtcttgt                                                    19

<210> SEQ ID NO 59
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 59
gcttacttcc tcctcccttt                                                   20

<210> SEQ ID NO 60
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 60
ccaggtgata ggagcagaac t                                                 21

<210> SEQ ID NO 61
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 61
accctccttc ctccctctct                                                   20

<210> SEQ ID NO 62
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 62
ccactctccc ttctgtcctc t                                                 21

<210> SEQ ID NO 63
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 63
cctccttcct ccctctctct                                                   20
```

<210> SEQ ID NO 64
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 64
gtctgtccca tcatgccagg                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 65
tttctgatcc tgctgcctct                                              20

<210> SEQ ID NO 66
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 66
accctccttc ctccc                                                   15

<210> SEQ ID NO 67
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 67
ctccttcctc cctc                                                    14

<210> SEQ ID NO 68
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 68
ctccttcctc c                                                       11

<210> SEQ ID NO 69
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 69
cttcctccct ctctc                                                   15

<210> SEQ ID NO 70
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 70
atcctgctgc ctct                                                14

<210> SEQ ID NO 71
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 71
ctccttcctc cctc                                                14

<210> SEQ ID NO 72
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 72
accctccttc ctccc                                               15

<210> SEQ ID NO 73
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 73
gttctggctc tgctgtagga                                          20

<210> SEQ ID NO 74
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 74
atgctcactc acttccggcg                                          20

<210> SEQ ID NO 75
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 75
ctttgtggtg tcagcctttg t                                        21

<210> SEQ ID NO 76
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 76
aggtgtgagc gcagggtaca                                          20

<210> SEQ ID NO 77

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 77
ctcggttaca gcgcgtctct                                              20

<210> SEQ ID NO 78
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 78
aactctccgg cgtttgcag                                               19

<210> SEQ ID NO 79
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 79
tgttgtccca gttactcct                                               19

<210> SEQ ID NO 80
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 80
gccaggagtt caagagcagc                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 81
ccttgttggc acctcactgt                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 82
gttgtgcggt taatactccc                                              20

<210> SEQ ID NO 83
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 83
```
gtgagtctcg aagtggtagc t                                                  21

<210> SEQ ID NO 84
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 84
gactcttatc tacctgtggg a                                                  21

<210> SEQ ID NO 85
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 85
tccttctcct cttgtctctc c                                                  21

<210> SEQ ID NO 86
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 86
gccctgtgtt tctcctctcc                                                    20

<210> SEQ ID NO 87
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 87
actcccgtgg tctctgtgtc t                                                  21

<210> SEQ ID NO 88
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 88
tccagcaacc tcactctccc                                                    20

<210> SEQ ID NO 89
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 89
gcgtgggtgt ggtcagtgta                                                    20

<210> SEQ ID NO 90
<211> LENGTH: 20
<212> TYPE: DNA

```
<213> ORGANISM: Artificial Sequence
<220> FEATURE:
<223> OTHER INFORMATION: Antisense oligonucleotide

<400> SEQUENCE: 90
accacctcct gctccagact                                              20

<210> SEQ ID NO 91
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 91
cctctccctc tctctgtctc t                                            21

<210> SEQ ID NO 92
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 92
atcttccctc tcacccttc                                               19

<210> SEQ ID NO 93
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 93
cccttctgtc tgatcttccc t                                            21

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
tctgtgtcca cctgtctccc                                              20

<210> SEQ ID NO 95
<211> LENGTH: 25
<212> TYPE: DNA
<213> ORGANISM: Homo sapiens

<400> SEQUENCE: 95
aactggagct ggggtgtctg tttca                                        25

<210> SEQ ID NO 96
<211> LENGTH: 25
<212> TYPE: DNA
<213> ORGANISM: Artificial Sequence
<220> FEATURE:
<223> OTHER INFORMATION: Forward Primer Sequence

<400> SEQUENCE: 96
ccatcagacg acatcccta acaaa                                         25
```

```
<210> SEQ ID NO 97
<211> LENGTH: 31
<212> TYPE: DNA
<213> ORGANISM: Artificial Sequence
<220> FEATURE:
<223> OTHER INFORMATION: Reverse Primer Sequence

<400> SEQUENCE: 97
acattatatc atagctccta aaggagatgc a                              31

<210> SEQ ID NO 98
<211> LENGTH: 16
<212> TYPE: DNA
<213> ORGANISM: Artificial Sequence
<220> FEATURE:
<223> OTHER INFORMATION: Reporter Sequence

<400> SEQUENCE: 98
cagagtttca attccc                                               16

<210> SEQ ID NO 99
<211> LENGTH: 12
<212> TYPE: DNA
<213> ORGANISM: Artificial Sequence
<220> FEATURE:
<223> OTHER INFORMATION: Antisense Oligonucleotide

<400> SEQUENCE: 99
gctagtctgt tg                                                   12

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
caccatgccc ggctaatttt                                           20

<210> SEQ ID NO 101
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 101
gaguucagau uuuaacac                                             19

<210> SEQ ID NO 102
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 102
auucuccugc cucagccuc                                            19

<210> SEQ ID NO 103
<211> LENGTH: 19
<212> TYPE: DNA
<213> ORGANISM: Artificial Sequence
<220> FEATURE:
<223> OTHER INFORMATION: Antisense Oligonucleotide
```

<400> SEQUENCE: 103
ugaagaugcu gugaaauua                                                                        19